United States Patent
Moorman et al.

(10) Patent No.: US 6,906,078 B2
(45) Date of Patent: Jun. 14, 2005

(54) METHOD OF USING ($H^+/K^+$) ATPASE INHIBITORS AS ANTIVIRAL AGENTS

(75) Inventors: Alan E Moorman, Skokie, IL (US); Daniel P Becker, Glenview, IL (US); Daniel L Flynn, Mundelein, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/885,221

(22) Filed: Jun. 20, 2001

(65) Prior Publication Data

US 2001/0047038 A1 Nov. 29, 2001

Related U.S. Application Data

(63) Continuation of application No. 09/605,560, filed on Jun. 27, 2000, now abandoned, which is a continuation of application No. 09/377,888, filed on Aug. 19, 1999, now abandoned, which is a continuation of application No. 08/659,098, filed on Jun. 4, 1996, now abandoned, which is a continuation of application No. 08/235,619, filed on Apr. 24, 1994, now abandoned.

(51) Int. Cl.$^7$ ............................................. A61K 31/505
(52) U.S. Cl. ..................... 514/269; 514/307; 514/322
(58) Field of Search ................................ 514/269, 307, 514/322

(56) References Cited

U.S. PATENT DOCUMENTS

| | | | |
|---|---|---|---|
| 4,045,563 A | | 8/1977 | Berntsson et al. |
| 4,045,564 A | | 8/1977 | Berntsson et al. |
| 4,182,766 A | | 1/1980 | Krassóet al. |
| 4,248,880 A | | 2/1981 | Krasso et al. |
| 4,255,431 A | | 3/1981 | Junggren et al. |
| 4,327,102 A | | 4/1982 | Crossley |
| 4,337,257 A | | 6/1982 | Junggren et al. |
| 4,359,465 A | * | 11/1982 | Ruwart ........................ 424/263 |
| 4,371,537 A | | 2/1983 | Markley et al. |
| 4,394,509 A | | 7/1983 | Crossley |
| 4,472,409 A | * | 9/1984 | Senn-Bilfinger ............ 424/263 |
| 4,772,619 A | | 9/1988 | Adelstein et al. |
| 5,198,552 A | | 3/1993 | Trofimov et al. |
| 5,605,919 A | | 2/1997 | Matsumori |
| 5,679,695 A | | 10/1997 | Wassmundt |
| 5,945,425 A | * | 8/1999 | Moormann et al. ......... 514/269 |

FOREIGN PATENT DOCUMENTS

| | | |
|---|---|---|
| DE | 3415971 A1 | 11/1984 |
| EP | 130 729 A2 | 1/1985 |
| EP | 127 763 B1 | 12/1985 |
| EP | 167 943 A2 | 1/1986 |
| EP | 178 438 A1 | 4/1986 |
| EP | 194 458 B1 | 9/1986 |
| EP | 234 690 B1 | 9/1986 |
| EP | 335 646 A1 | 10/1989 |
| EP | 354 788 B1 | 2/1990 |
| EP | 407 217 A1 | 1/1991 |
| EP | 514 830 B1 | 11/1992 |
| GB | 2134523 A | 8/1984 |
| GB | 2161160 A | 1/1986 |
| JP | 1230560 | 9/1989 |
| WO | WO 92/07867 A1 | 5/1992 |

OTHER PUBLICATIONS

Lindberg et al, TIPS, vol. 8, Oct. 1987, pp 399–402.*
Lindberg et al., "Structure–activity relationships of omeprazole analogues and their mechanism of action." Trends in Pharmaceutical Sciences, 1987, pp. 399–402, vol. 8, No. 10.
Hayashi et al., "In Vitro and in Vivo Antiviral Activity of Scopadulcic Acid B from *Scoparia dulcis*, Scrophulariaceae, Against Herpes Simplex Virus type1." Antiviral Research, 1988, pp. 345–354, vol. 9.
Holsey et al., "Evidence for Poliovirus–Induced Cytoplasmic Alkalinization iN HeLa Cells." J. of Cellular Physiology, 1990, pp. 586–591, vol. 142.
Hayashi et al., "Scopadulcic Acid B, a NEw Tetracyclic Diterpenoid from *Scoparia dulcis* L. Its Structure, H+, K+–Adenosine Triphosphatase Inhibitory Activity and Pharmacokinetic Behaviour in Rats." Chem, Pharm, Bull., 1990, pp. 2740–2745, vol. 38, No. 1.
Hayshi et al., "Antiviral Agents of Plant Origin. II. Antiviral Activity of Scopadulcic Acid B Derivatives." Chem, Pharm, Bull., 1990, pp. 239–242, vol. 38, No. 1.
Naruse et al., "Pumilacidin, A Complex of New Antiviral Antibiotics Production, Isolation, Chemical Properties. Structure and Biological Activity." J. Antibodies, 1990, pp. 267–280, vol. 43, No. 3.

(Continued)

*Primary Examiner*—Shailendra Kumar

(57) ABSTRACT

A class of compounds which are ($H^+/K^+$)ATPase inhibitors can be used for the treatment of viral infections. Compounds of particular interest are defined by Formula III:

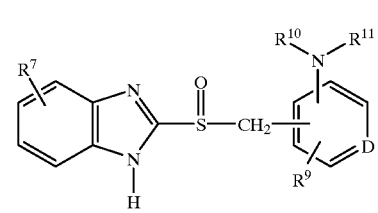

wherein D is N or CH; wherein $R^7$ is one or more radicals selected from hydrido, alkoxy, amino, cyano, nitro, hydroxyl, alkyl, halo, haloalkyl, carboxyl, alkanoyl, nitro, amino, alkylamino, amide, alkylamide, alkoxycarbonyl, alkylthio, alkylsulfinyl and alkylsulfonyl; wherein $R^9$ is one or more radicals selected from hydrido, alkoxy, amino, alkyl, halo, cyano, nitro, hydroxyl, haloalkyl, carboxyl, alkanoyl, nitro, amine, alkylamine, dialkylamine, amide, alkylamine, alkoxycarbonyl, alkylthio, alkylsulfinyl and alkylsulfonyl; and wherein $R^{10}$ and $R^{11}$ are independently selected from hydrido and alkyl; or a pharmaceutically acceptable salt thereof.

10 Claims, No Drawings

OTHER PUBLICATIONS

Ljungman et al., "Acyclovir–Resistant Herps Simplex Virus Causing Pneumonia after Marrow Transplantation." J. Infec. Dis., 1990, pp. 244–248, vol. 162, No. 1.

Gately et al., "Herpes Simplex Virus Type 2 Meningoencephalitis Resistant to Acyclovir in a Patient with Aids." J. Infect. Dis., 1990, pp. 711–715, vol. 161, No. 4.

Lui et al., "The Herpes Simplex Virus 1 Gene Encoding a Protease Also Contains within Its Coding Domain the Gene Encoding the More Abundant Substrate." J. Virol., 1991, pp. 5149–5156, vol. 65, No. 10.

Welch et al., "A Herpesvirus Matirational Proteinase, assembling: Identification of its Gene, Putative active site domain, and cleavage site." Proc. Natl. Acad. sci. USA, 1991, pp. 10792–10796, vol. 88, No. 23.

Altamirano et al., "Human Cytomegalovirus Infection Increases the Number of Ouabain–Binding Sites in Human Fibroblasts." Virology, 1994, pp. 151–159, vol. 199.

* cited by examiner

METHOD OF USING (H+/K+) ATPASE INHIBITORS AS ANTIVIRAL AGENTS

REFERENCE TO RELATED APPLICATIONS

This application is a continuation of Ser. No. 09/605,560, filed Jun. 27, 2000, now abandoned, which is a continuation application of Ser. No. 09/377,888, filed Aug. 19, 1999, now abandoned, which is a continuation application of Ser. No. 08/659,098, filed Jun. 4, 1996, now abandoned, which is a continuation of application Ser. No. 08/235,619, filed Apr. 24, 1994, now abandoned.

FIELD OF THE INVENTION

This invention relates to methods of treating subjects having viral infections. More particularly, this invention relates to the use of (H+/K+)ATPase inhibitors for treating viral infections.

BACKGROUND OF THE INVENTION

Inhibition of the (H+/K+)ATPase proton pump, located in the gastric secretory membranes, has been a target for controlling gastric acid secretion in the treatment of ulcers.

Several families of compounds have been described as gastric acid secretion inhibitors, including heterocyclylalkylsulfinylbenzimidazoles (see U.S. Pat. Nos. 4,472,409, 4,394,509, 4,337,257, 4,327,102, 4,255,431, 4,045,564, 4,045,563 and 4,772,619; British Patent No. 2,134,523; and German Offenlegungsschrift No. 3,415,971) and heterocyclylalkylsulfinylnaphth[2,3-d]imidazoles (see U.S. Pat. Nos. 4,248,880 and 4,182,766). Similarly, other substituted benzimidazoles having a ring fused to the benzimidazole group have been described as gastric acid secretion inhibitors and cytoprotective agents. See EP Nos. 130,729 and 127,763.

Some heterocyclylalkylsulfinylbenzimidazoles have also been described as cytoprotective agents. See U.S. Pat. No. 4,359,465 and Great Britain Application 2,161,160, published Jan. 8, 1986. Omeprazole is an example of a class of benzimidazoles which inhibit the proton pump [Lindberg et al, *Trends in Pharmaceutical Sciences*, 399 (1987)].

It has been described that inhibitors of sodium transport reduce virus yields [A. A. Altamirano et al, *Virology*, 199, 151 (1994)]. There have been reports of isolated natural products which have been independently described as having (H+/K+) ATPase inhibitors and antiviral activity. T. Hayashi et al describe the isolation of scopadulcic acid B and its activity against (H+/K+)ATPase [*Chem. Pharm. Bull.*, 38, 2740 (1990)] and HSV-1 [*Chem. Pharm. Bull.*, 38, 239 (1990) and *Antiviral Res.*, 9, 345 (1988)]. Pumilacidins are a class of heptapeptide antibiotics that have been isolated and described as being inhibitory to HSV-1 as well as (H+/K+)ATPase [N. Naruse et al, *J. Antibiotics*, 43, 267 (1990)].

There is a great need for new therapies active in the treatment of viral diseases. Whereas there has been great progress in developing a variety of therapies for the treatment of bacterial infections, there are few viable therapies for the treatment of viruses. Zidovudine is the primary approved treatment for human immunodeficiency virus. Ganciclovir, acyclovir and foscarnet are currently utilized for the treatment of herpesvirus infections. However, these therapies can have substantial side effects based on their deleterious effects on host cell DNA replication or effect of a limited number of viral infections. In addition, viruses are known to develop resistance to therapies which causes a progressive decline in efficacy [Ljungman et al., *J. Infect. Dis.*, 162, 244 (1990) and Gately et al, *J. Infect. Dis.*, 161, 711 (1990)].

Herpesviridae is a family of DNA viruses which include herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV6), human herpesvirus-7 (HHV7), pseudorabies and rhinotracheitis, among others.

It is known that herpesviruses express their genetic content by directing the synthesis of a number of proteins encoded by the herpesvirus DNA in the host cell. One of the important virus encoded proteins is made as a precursor consisting of an amino terminal-located protease and carboxyl terminal-located assembly protein. This precursor is proteolytically processed in an autocatalytic manner at a specific amino acid sequence known as the "release" site yielding separate protease and assembly protein. The assembly protein is cleaved further by the protease at another specific amino acid sequence known as the "maturation" cleavage site. Recently, EP No. 514,830, published Nov. 25, 1992, describes a virus-specific serine protease which has a role in herpesvirus replication. Additionally, Lui and Roizman (*J. Virol*, 65, 5149 (1991)) describe the sequence and activity of a protease and the associated assembly protein encoded by $U_L26$ of HSV-1. A. R. Welch et al (*Proc. Natl. Acad. Sci. USA*, 88, 10792 (1991)) describe the related protease (also known as assemblin) and assembly protein encoded by $U_L80$ of CMV. An approach currently being investigated for potential use in the treatment of herpesvirus infections is the development of inhibitors of herpesvirus proteases.

U.S. Pat. No. 4,371,537 describes sulfur substituted phenoxypyridines as having activity against RNA viruses, and specifically describes 2,5-bis(benzylthio)pyridine.

Benzimidazoles have been investigated for antiviral activity [R. W. Sidwell and J. T. Witkowski, Antiviral Agents, in BURGER'S MEDICINAL CHEMISTRY, PART II (M. Wolff, 4th ed. 1979)]. Specifically, 2-(α-hydroxybenzyl benzimidazole is described as a selective inhibitor of RNA enteroviruses.

EP No. 335,646, published Oct. 4, 1989, describes sulfur-containing compounds as having activity against rhinoviruses and coxsaki virus. Specifically, 5-[7-(benzimidazol-2-yl)sulfoxyheptyl]-3-methylisoxazole is described.

EP 407,217, published Jan., 9, 1991, describes compounds as having activity against RNA viruses. 2-[6-(2-chloro-4-methoxyphenoxy)-1-hexylthio]-benzimidazole is specifically described.

DE 3891468, published Feb. 24, 1994, describes prophylactic anti-herpesvirus activity of 6-bromo-5-hydroxy-4-dimethylaminomethyl-1-methyl-2-phenylthiomethylindol-3-carboxylic acid ethyl ester.

Polysubstituted benzimidazoles with activity against viruses of the herpes family are described in WO 92/07867. 2-Benzylthio-5,6-dichloro-1-(β-D-ribofuranosyl) benzimidazole is specifically described.

DESCRIPTION OF THE INVENTION

The invention involves a method of treating a subject having a viral infection with an (H+/K+)ATPase inhibitor. Preferably, the (H+/K+)ATPase inhibitor contains a sulfur radical, such as an alkylthio radical, a sulfoxide radical, a sulfone, or the like. More preferably, the (H+/K+)ATPase inhibitor contains a sulfoxide radical.

Viruses are classified into broad categories based on whether they incorporate RNA or DNA. Important virus families classified of RNA type include orthomyxoviridae, paramyxoviridae, picornaviridae, rhabdoviridae, coronaviridae, togaviridae, bunyaviridae, arenaviridae and retroviridae. Important virus families classified of DNA type include adenoviridae, poxviridae, papovaviridae and herpesviridae.

The compounds of this invention have been shown to be particularly effective against herpetoviridae. Thus they are particularly useful for the treatment of herpes simplex viruses (HSV-1, HSV-2), cytomegalovirus (CMV), herpes varicella-zoster, Epstein-Barr, HHV6, HHV7, pseudorabies and rhinotracheitis, among others.

The invention further involves a method of treating a subject having a viral infection with a effective amount of a compound which can inhibit both a ($H^+/K^+$)ATPase and a virus-specific serine protease.

In addition, the invention involves a method of treating viral infection in a subject, the method comprising treating the subject with an effective amount of a compound of Formula I

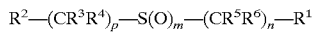

$$R^2-(CR^3R^4)_p-S(O)_m-(CR^5R^6)_n-R^1 \qquad I$$

wherein $R^1$ is selected from alkoxy, alkoxycarbonyl, dialkylamino, aryl and heteroaryl, wherein $R^1$ is optionally substituted at a substitutable position with one or more radicals selected from alkoxy, aminoalkoxy optionally substituted on the nitrogen atom with alkyl, cycloalkyl, and aralkyl, hydroxyl, cyano, nitro, alkyl, halo, haloalkyl, haloalkoxy, alkanoyl, cycloalkylalkoxy, carboxyl, acyl, amide, alkylamide, aralkoxy, alkenyloxy, alkynyloxy, sulfonamidyl, dialkylsulfonamidyl, heterocyclic, aralkyl, heteroaralkyl, alkoxycarbonyl, heteroaryl, alkylthio, alkylsulfinyl, alkylsulfonyl, alkenylthio, arylthio, aralkylthio, cycloalkylthio, alkylimino and amino optionally substituted with a radical selected from alkyl, aralkyl, aryl, alkenyl, alkynyl, cycloalkyl, acyl, cycloalkenyl, hydroxyalkyl, alkoxycarbonyl and alkoxyalkyl;

wherein $R^2$ is heteroaryl, wherein $R^2$ is optionally substituted at a substitutable position with one or more radicals selected from alkoxy, amino, cyano, nitro, hydroxyl, alkyl, cycloalkyl, halo, haloalkyl, haloalkoxy, carboxyl, alkanoyl, acyl, alkylamino, arylamino, alkylarylamino, alkanoylamino, alkylaminoalkyl, amide, alkylamide, alkoxycarbonyl, aryloxycarbonyl, aralkoxycarbonyl, alkylcarbonyl, cycloalkylcarbonyl, alkylcarbonylalkyl, alkoxycarbonylalkyl, dialkylcarbamoyl, carbamoyloxy, aryloxy, aralkoxy, alkenyloxy, alkynyloxy, acyloxy, cycloalkylalkoxy, aralkyl, aryl, aroyl, alkoxyalkyl, hydroxyalkyl, heterocyclic, heteroaralkyl, alkylthio, alkylsulfinyl, alkylsulfonyl, arylthio, arylsulfinyl, alkylsulfonyl, sulfonamidyl and alkylsulfonamidyl;

wherein each of $R^3$, $R^4$, $R^5$ and $R^6$ is independently selected from hydrido, alkyl, aryl and aralkyl; and wherein each of m, n and p is a number independently selected from 0, 1 and 2;

provided that when $R^1$ is phenyl, $R^2$ is not selected from pyridyl, 1-methylindol and 1-(β-D-ribofuranosyl) benzimidazole when m is 0 or 2;

or a pharmaceutically acceptable salt thereof.

A preferred class of compounds consists of those compounds of Formula I wherein $R^1$ is selected from lower alkoxy, lower alkoxycarbonyl, lower dialkylamino, phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, wherein $R^1$ is optionally substituted at a substitutable position with one or more radicals selected from lower alkoxy, lower aminoalkoxy optionally substituted on the nitrogen atom with lower alkyl, lower cycloalkyl and lower aralkyl, cyano, nitro, hydroxyl, lower alkyl, halo, lower haloalkyl, lower haloalkoxy, lower cycloalkylalkoxy, carboxyl, acyl, lower alkanoyl, amide, lower alkylamide, lower aralkoxy, lower alkenyloxy, lower alkynyloxy, sulfonamidyl, lower dialkylsulfonamidyl, 5 to 20 membered heterocyclic, lower aralkyl, lower heteroaralkyl, lower alkoxycarbonyl, 5 to 8 membered heteroaryl, lower alkylthio, lower alkylsulfinyl, lower alkylsulfonyl, lower alkenylthio, lower arylthio, lower aralkylthio, lower cycloalkylthio, lower alkylimino and amino optionally substituted with a radical selected from lower alkyl, lower aralkyl, phenyl, lower alkenyl, lower alkynyl, lower cycloalkyl, acyl, lower cycloalkenyl, lower hydroxyalkyl, lower alkoxycarbonyl and lower alkoxyalkyl; wherein $R^2$ is selected from nitrogen-containing heteroaryl, wherein $R^2$ is optionally substituted at a substitutable position with one or more radicals selected from lower alkoxy, amino, cyano, nitro, hydroxyl, lower alkyl, lower cycloalkyl, halo, lower haloalkyl, lower haloalkoxy, carboxyl, lower alkanoyl, acyl, lower alkylamino, lower arylamino, lower alkylarylamino, lower alkanoylamino, lower alkylaminoalkyl, amide, lower alkylamide, lower alkoxycarbonyl, lower aryloxycarbonyl, lower aralkoxycarbonyl, lower alkylcarbonyl, lower cycloalkylcarbonyl, lower alkylcarbonylalkyl, lower alkoxycarbonylalkyl, lower dialkylcarbamoyl, carbamoyloxy, lower aryloxy, lower aralkoxy, lower alkenyloxy, lower alkynyloxy, acyloxy, lower cycloalkylalkoxy, lower aralkyl, optionally substituted lower aryl, lower aroyl, lower alkoxyalkyl, lower hydroxyalkyl, 5 to 20 membered heterocyclic, lower heteroaralkyl, lower alkylthio, lower alkylsulfinyl, lower alkylsulfonyl, lower arylthio, lower arylsulfinyl, lower arylsulfonyl, sulfonamidyl and lower alkylsulfonamidyl; and wherein each of $R^3$, $R^4$, $R^5$ and $R^6$ is independently selected from hydrido, lower alkyl, phenyl, naphthyl and lower aralkyl.

A class of compounds of particular interest consists of those compounds of Formula I wherein $R^1$ is selected from phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidinyl, thienopyridinyl, dihydrothienopyridinyl, carbostyryl, pyrimidyl and pyrazinyl, wherein $R^1$ is optionally substituted at a substitutable position with one or more radicals selected from methoxy, ethoxy, propoxy, butoxy, isopropoxy, tert-butoxy, aminomethoxy optionally substituted on the nitrogen atom with methyl, ethyl, propyl, butyl, pentyl, isopropyl, isobutyl, tert-butyl, cyclohexyl, cyclopropyl and benzyl, hydroxyl, amino optionally substituted with a radical selected from methyl, ethyl, propyl, butyl, pentyl, isopropyl, isobutyl, tert-butyl, benzyl, phenethyl, phenyl, butene, pentene, isopropylene, isobutylene, propargyl, cyclopropyl, cyclobutyl, cyclopentyl, cyclohexyl, formyl, acetyl, cyclobutenyl, cyclopentenyl, cyclohexenyl, hydroxymethyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, and methoxymethyl, cyano, nitro, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, cyclohexylmethoxy, carboxyl, formyl, acetyl, propionyl, amide, methylamide, dimethylamide, benzyloxy, sulfonamidyl, dimethylsulfonamidyl, morpholinyl, pyrrolidinyl, piperazinyl, piperidyl, benzyl, methoxycarbonyl, ethoxycarbonyl, pyridyl, methylthio, methylsulfinyl, methylsulfonyl, phenylthio, benzylthio, cyclohexylthio and methylimino; wherein $R^2$ is selected from pyridyl, indolyl, imidazolyl, benzimidazolyl, napthoimidazolyl, 1,3-dioxolobenximidazolyl, imidazopyridyl, imidazoquinolinyl, dihydroimidazoquinolinyl, cycloheptoimidazolyl, cyclooxaundecanobenzimidazolyl, benzoxazolyl, benzothiazolyl, indolyl, thienoimidazolyl, pyridopyrazinyl, quinolinyl, quinoxalinyl, quinazolinyl, quinazolinonyl, triazolyl, tetrazolyl, oxazolyl, purinyl, indenoimidazolyl, thiadiazolyl, thiazolylpyridyl, pyridyl, pyrimidinyl, pyranobenzimidazolyl, thiopyranbenzimidazolyl, indolbenzimidazole, tetrahydroimidazoquinolinyl, wherein $R^2$ is optionally substituted at a substitutable position with one or more radicals selected from methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, cyclohexyl, cyclopropyl, cyclobutyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, trifluoroethoxy, carboxyl, formyl, acetyl, propionyl, butyryl, N-methylamino, methylamino, N-propylamino, N-butylamino, N-tert-butylamino, N-pentylamino, N-hexylamino, N,N-dimethylamino, phenylamino, N-methyl-N-phenylamino, methylaminomethyl, amide, N-methylamide, N,N-dimethylamide, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, phenoxycarbonyl, benzyloxycarbonyl, methylcarbonyl, cyclohexylcarbonyl, methylcarbonylmethyl, methoxycarbonylmethyl, N,N-dimethylcarbamoyl, carbamoyloxy, phenoxy, benzoxy, benzyl, phenethyl, phenyl, benzoyl, methoxymethyl, hydroxymethyl, morpholinyl, pyrrolidinyl, piperazinyl, piperidyl, methylthio, ethylthio, methylsulfinyl, ethylsulfinyl, methylsulfonyl, phenylthio, phenylsulfinyl, phenylsulfonyl, sulfonamidyl, methylsulfonamidyl and N,N-dimethylsulfonamidyl; and wherein each of $R^3$, $R^4$, $R^5$ and $R^6$ is independently selected from hydrido, methyl, ethyl, propyl, butyl, pentyl, isopropyl, isobutyl, tert-butyl, phenyl and benzyl.

A family of specific compounds of particular interest within Formula I consists of compounds, and their pharmaceutically acceptable salts, of the group selected from:

[2-[(2-N-isobutyl-N-methylamino)-benzyl]sulfinyl]-1H-benzimidazole;

2-[[3-methylpyridin-2-ylmethyl]sulfinyl]-1H-benzimidazole;

2-[(imidazo[1,2-a]pyridin-3-ylmethyl)sulfinyl]-1H-benzimidazole;

2-[(imidazo[1,2-a]pyridin-3-ylmethyl)sulfinyl]-1H-benzimidazole;

2-[(imidazo[1,2-a]pyridin-3-ylmethyl)sulfinyl]-5-methyl-1-H-benzimidazole;

2-[(imidazo[1,2-a]pyridin-3-ylmethyl)sulfinyl]-5-methoxy-1H-benzimidazole;

5-chloro-2-[(imidazo[1,2-a]pyridin-3-yl-methyl)sulfinyl]-1H-benzimidazole;

2-[(imidazo[1,2-a]pyridin-3-ylmethyl)sulfinyl]-5-trifluoromethyl-1H-benzimidazole;

2-[(imidazo[1,2-a]pyridin-8-ylmethyl)sulfinyl]-1H-benzimidazole;

2-[(imidazo[1,2-a]pyridin-8-ylmethyl)sulfinyl]-1H-benzimidazole;

2-[(imidazo[1,2-a]pyridin-8-ylmethyl)sulfinyl]-5-methoxy-1H-benzimidazole;

5-ethoxy-2-[(imidazo[1,2-a]pyridin-8-yl-methyl)sulfinyl]-1H-benzimidazole;

2-[(imidazo[1,2-a]pyridin-8-ylmethyl)sulfinyl]-4-methyl-1H-benzimidazole;

2-[(imidazo[1,2-a]pyridin-8-ylmethyl)sulfinyl]-5-methyl-1H-benzimidazole;

2-[(imidazo[1,2-a]pyridin-8-ylmethyl)sulfinyl]-5,6-dimethyl-1H-benzimidazole;

2-[(imidazo[1,2-a]pyridin-8-ylmethyl)sulfinyl]-5,6-dimethoxy-1H-benzimidazole;

5-chloro-2-[(imidazo[1,2-a]pyridin-8-yl-methyl)sulfinyl]-1H-benzimidazole;

2-[(imidazo[1,2-a]pyridin-8-ylmethyl)sulfinyl]-5-trifluoromethyl-1H-benzimidazole;

2-[[(2,3-dimethylimidazo[1,2-a]pyridin-8-yl)methyl]sulfinyl]-1H-benzimidazole;

2-[[(3-methylimidazo[1,2-a]pyridin-8-yl)methyl]sulfinyl]-1H-benzimidazole;

2-[[(2-phenylimidazo[1,2-a]pyridin-8-yl)methyl]sulfinyl]-1H-benzimidazole;

2-[[(3-phenylimidazo[1,2-a]pyridin-8-yl)methyl]sulfinyl]-1H-benzimidazole;

2-[[(3-(4-nitrophenyl)imidazo[1,2-a]pyridin-8-yl)methyl]sulfinyl]-1H-benzimidazole;

2-[[[3-[3-(trifluoromethyl)phenyl]imidazo[1,2-a]pyridin-8-yl]methyl]sulfinyl]-1H-benzimidazole;

5-methyl-2-[[[3-[3-(trifluoromethyl)phenyl]imidazo[1,2-a]pyridin-8-yl]methyl]sulfinyl]-1H-benzimidazole;

5-chloro-2-[[[3-[3-(trifluoromethyl)phenyl]imidazo[1,2-a]pyridin-8-yl]methyl]sulfinyl]-1H-benzimidazole;

2-[[[3-[4-(trifluoromethyl)phenyl]imidazo[1,2-a]pyridin-8-yl]methyl]sulfinyl]-1H-benzimidazole;

5-chloro-2-[[[3-[4-(trifluoromethyl)phenyl]imidazo[1,2-a]pyridin-8-yl]methyl]sulfinyl]-1H-benzimidazole;

4-[8-[(1H-benzimidazol-2-yl)sulfinyl)methyl]imidazo[1,2-a]pyridin-3-yl]benzoate;

2-[[[3-(4-chlorophenyl) imidazo[1,2-a]pyridin-8-yl]methyl]sulfinyl]-1H-benzimidazole;

2-[[[3-(4-methylphenyl)imidazo[1,2-a]pyridin-8-yl]methyl]sulfinyl]-1H-benzimidazole;
2-[(imidazo[1,2-a]pyridin-5-ylmethyl)sulfinyl]-1H-benzimidazole;
2-((n-butoxycarbonylmethyl)sulfinyl) thiazolo(5,4-b)pyridine;
5-chloro-2-((2-ethoxyethyl)sulfinyl)benzothiazole;
4,6-dimethyl-2-(((imidazo(1,2-a)pyridin-2-yl)methyl)thio)-1H-benzimidazole;
2-[3-methyl-4-(2-(N-benzyl-N-cyclohexylamino)-ethoxy)pyridyl]methylthio-1H-benzimidazole;
ethyl 2-[(1H-benzimidazol-2-yl)thiomethyl]-4-methyl-amino-5-pyrimidine carboxylate;
9-(benzimidazol-2-yl)sulfinyl-4-methoxy-2,3-cycloheptenopyridine;
2-(5-fluoro-2-(4-methoxy-2-pyridyl)-phenylsulfinyl)-1H-benzimidazole;
5-difluoromethoxy-2-(((3,4-dimethoxy-2-pyridinyl)-methyl)sulfinyl)-1H-benzimidazole;
2-(((4-difluoromethoxy-3-methyl-2-pyridyl)methylsulfinyl)benzimidazole;
2-[4(3-methoxypropoxy)-3-methylpyridine-2-yl]methylsulfinyl-1H-imidazole;
2-((6-azachroman-5-ylmethyl)sulfinyl)-benzimidazole;
5-carbomethoxy-6-methyl-2-(((3,4-dimethoxy-2-pyridinyl)-methyl)sulfinyl-1H-benzimidazole;
5-carbomethoxy-6-methyl-2-(((3,4-dimethoxy-2-pyridinyl)-methyl)sulfinyl)-1H-benzimidazol-1-yl-methyl ethylcarbonate;
2-((3-methyl-4-(2,2,2-trifluoroethoxy)-2-pyridyl)methylsulfinyl)benzimidazole;
4-fluoro-2-(((4-methoxy-2-pyridinyl)methyl)sulfinyl-1H-benzimidazol-1-yl-methyl-ethylcarbonate;
2-[3-methyl-4-(1-benzyl-4-piperidyl)oxy-2-pyridyl]methylthio-1H-benzimidazole;
2-(3-methyl-4-(2-(N-methyl-N-(4-methyl-benzyl)amino) ethoxy)-2-pyridyl)methylsulfonyl-1H-benzimidazole;
2-(4-methoxy-6-methyl-2-pyrimidinyl)methylthio-1H-benzimidazole;
2-[2-[N-4-(3-fluorophenyl)-butyl-N-methyl]aminoethyl]thio-(1H)-benzimidazole;
5-chloro-2-(3,4-dimethoxy-2-pyridylmethylsulfinyl)-1H-benzimidazole;
5-fluoro-2-(4-cyclopropylmethoxy-2-pyridylmethylsulfinyl)-1H-benzimidazole;
4-fluoro-2-(4-methoxy-2-pyridylmethylsulfinyl)-1H-benzimidazole;
2-(((4-methoxy-3,5-dimethyl-2-pyridinyl)-methyl)-sulfinyl)-5-methoxy-1H-benzimidazole;
5-hydroxymethyl-2-((3,5-dimethyl-4-methoxy-2-pyridyl-)methylthio-1H-benzimidazole;
2-(4-ethylthio-3-methylpyridin-2-yl-methyl)sulfinyl-benzimidazole;
2-(((4-(2-benzyloxyethoxy)-3-methyl-2-pyridyl)methylthio)benzimidazole;
2-[[2-[N-(2-hydroxyethyl)-N-methylamino]-5-methoxy]benzylsulfinyl]benzimidazole;
2-[2-(3,5-dimethyl-4-ethoxy) pyridylmethylsulfinyl]-5-methoxy-imidazo(4,5-b)pyridine;
2-(5-benzyl-4-chloro-6-methyl-2-pyrimidinyl)methylthio-1H-benzimidazole;
2,2-difluoro-6-((5-benzyloxy-4-methoxy-2-pyridyl)methylthio)-5H-(1,3)-dioxolo(4,5-f)benzimidazole;
5-carboethoxy-6-methyl-2-(((3-methyl-2-pyridyl)methyl)sulfinyl)-1H-benzimidazole;
5-(2-benzimidazolylsulfinylmethyl)-3,4-dihydro-4-methyl-2H-1,4-benzoxazine;
2-(3-methyl-4-(2-(N-benzyl-N-methylamino) ethoxy-2-pyridyl)methylsulfinyl-1H-benzimidazole;
2-(3-methyl-4-(2-(1,2,3,4-tetrahydroisoquinolin-2-yl)-ethoxy)-2-pyridyl)methylsulfinyl-1H-benzimidazole;
2-[1-(3,5-dimethylpyrazolyl)]methylthiobenzimidazole;
2-(3-chloro-4-methoxy-2-picolylthio)-5-methoxy-1H-benzimidazole;
2-(4-(2-ethoxyethoxy)-3-methyl-2-pyridyl)methylsulfinyl-1H-benzimidazole;
2-(3-methylthieno(2,3-c)pyridin-7-yl)methylsulfinyl)-benzimidazole;
2-(2-dimethylamino-5-methoxybenzylsulfinyl)-5-methoxy-benzimidazole;
2-(2-dimethylamino-5-methylbenzylsulfinyl)-5-methoxybenzimidazole;
2-[4-(2,3,5-trimethyl)pyridylthio]-5-methoxybenzimidazole;
2[(2-(4-chlorophenyl)-5-methylimidazol-4-yl)methylthio]-benzimidazole;
2-(5-hydroxy-1H-benzimidazol-2-ylsulfinylmethyl)-N,N-dimethylbenzenamine;
2-((6-methoxyisoquinolin-1-yl)methylsulfinyl)benzimidazole;
3-(5-methoxy-1H-benzimidazol-2-yl)thiomethylcarbostyril;
5-methoxy-2-(4-dimethylamino-5-fluoro-2-pyridylmethylsulfinyl)-1H-benzimidazole;
2-(2-dimethylaminobenzyl-sulfinyl)-5-cyclopropylmethoxy)benzimidazole;
2-(3,5-dimethyl-2-pyridylmethylsulfinyl)-5-cyclopropylmethoxy-benzimidazole;
2-[2-(N-cyclohexyl-N-methylamino)benzylsulfonyl]benzimidazole;
8-(5-fluoro-6-methoxy-2-benzimidazolyl)sulfinylmethyl-1-ethyl-4-(N-methyl-N-allyl)amino-1,2,3,4-tetrahydroquinoline;
2-(2-benzyloxycarbonylaminobenzylthio)benzimidazole;
2-(2-benzimidazolylmethylthio)pyrimidine;
2-(2-dimethylaminobenzylsulfinyl) imidazo[4,5-b]pyridine;
2-(2-pyridylmethylsulfinyl)quinoxaline;
2-methyl-3-(2-pyridylmethylsulfinyl)pyrido[2,3-b]pyrazine;
5-acetyl-2-((2-dimethylaminobenzyl)sulfinyl)benzimidazole;
2-((3,5-dimethyl-4-methoxy-2-pyridyl)methylsulfinyl)-5-fluoro-1H-benzimidazole;
2-(3-pyridylmethylthio)-5-methoxybenzimidazole;
2-(2-methylaminobenzylsulfinyl)benzimidazole;
5-methoxy-2-(2-dimethylaminobenzylsulfinyl)-1H-benzimidazole;
2-(3,4-dimethoxypyrid-2-ylmethylsulfinyl)-5-trifluoromethyl-benzimidazole;
5-methoxy-2-(4-piperidino-2-pyrimidinylmethylsulfinyl)-(1H)-benzimidazole;

2-[2-(4-benzyloxy)-pyridylmethylsulfinyl]
  benzimidazole;
4-allyloxy-8-(2-benzimidazolyl)thio-3-methyl-5,6,7,8-
  tetrahydroquinoline;
2-[2-(4-methoxy-5-n-pentyl)-pyridylmethylthio]
  benzimidazole;
2-(5-bromo-4-piperidino-2-pyridylmethylsulfinyl)-5-
  methoxy-(1H)-benzimidazole;
2-((3,5-dimethyl-4-morpholinopyrid-2-yl)
  methylsulfinyl)benzimidazole;
2-((2-pyridinylmethyl)sulfinyl)-1H-benzimidazole-1-
  methanol;
2-((3,4-dihydro-2H-thieno(3,2-c)pyridinylmethyl)thio)-
  1H-benzimidazole-1-methanol;
2-(4-isopropoxy-2-pyridyl)methylsulfinylbenzimidazole;
2-((4-fluorobenzyloxy-3-methyl-2-pyridyl)
  methylsulfinyl)benzimidazole;
2-(2-aminobenzylsulfinyl)-benzimidazole;
N,N-dimethyl-2-(1H-benzimidazol-2-yl-sulfinylmethyl)
  benzenamine;
2-[(4,5-dimethoxy-2-pyridyl)methylsulfinyl]-5-
  trifluoromethoxy-1H-benzimidazole;
2,2-difluoro-6-[(4,5-dimethoxy-2-pyridyl)methylthio]-
  5H-1,3-dioxolo-(4,5-f)benzimidazole;
2-((4-morpholinyl-3-ethylpyridin-2-ylmethyl)sulfinyl)-5-
  trifluoromethylbenzimidazole;
2-((4-methoxy-2-pyridyl)methylsulfinyl)-5-
  trifluoromethoxy-1H-benzimidazole;
5-cyclopropylcarbonyl-2-((4-methoxy-2-pyridyl)methyl-
  sulfinyl)-1H-benzimidazole;
2-[2-(3,5-dimethyl-4-methoxy)-pyridylmethylsulfinyl]-
  (5-chloro)-benzimidazole;
2-[2-(4,5-dimethyl)-pyridylmethylsulfinyl]-(5-acetyl-6-
  methyl)-benzimidazole;
1-(p-chlorobenzoyl)-2-(β-morpholinylmethyl-sulfinyl)
  benzimidazole;
2,3-dihydro-2-(2-pyridyl)thiazolo[3,2-a]benzimidazole-
  1-oxide;
2-[(2-pyridylmethyl)thio]-1H-naphth[2,3-d]imidazole;
1,5,6,7-tetrahydro-2-(5-methyl-2-pyridyl-methyl)-thio)
  indeno(5,6-d)imidazole;
4-methyl-2-(5-methyl-2-pyridyl-methylthio)-1H-naphtho
  (2,3-d)imidazole
2,2-difluoro-6-(4-methoxy-2-pyridylmethylsulfinyl)-5H-
  1,3-dioxolo[4,5-f]benzimidazole;
2-benzylthio-(4H)-imidazo(4,5,1-ij)quinoline;
2-(2-chlorophenylmethylthio)-5,6-dihydro-(4H)-imidazo
  (4,5,1-ij)quinoline;
5,6-dihydro-2-(2-pyridylmethylthio)-4H-imidazo(4,5,1-
  ij)quinoline;
5,6-dihydro-2-(2-(3,5-dimethylpyridyl)methylsulfinyl)-
  4H-imidazo;
5,7-dihydro-2-(((4-methoxy-3-methyl-2-pyridyl)methyl)
  sulfinyl)-5,5,7,7-tetramethylindeno(5,6-d)imidazol-6
  (1H)-one;
2-(2-pyridylmethylthio)-6-isopropyl-
  cycloheptoimidazole;
2-[2-(3,5-dimethyl)pyridylmethylsulfinyl-]5-fluoro-
  benzoxazole;
3-[(4-dimethylamino-2-pyridyl)methylthio]indole;
5-methyl-2-(2-pyridylmethylthio-3H-thieno(2,3-d)
  imidazole;
2-(2-(3,5-dimethyl-4-methoxy)pyridylmethylsulfinyl)-7-
  imidazo(4,5-b)pyridine;
2-(2-pyridylmethylsulfinyl)quinoxaline;
2-[(2-pyridyl)methylsulfinyl]thieno[3,4-d]-imidazole;
2-(((3,5-dimethyl-4-methoxy-2-pyridyl)methyl)thio)-4,5-
  diphenyloxazole;
3,5-dimethyl-4-methoxy-6-(((5-phenyl-1,2,4-triazol-3-
  yl)-thio)methyl)pyridine;
2-(((3,5-dimethyl-4-methoxy-2-pyridyl)methyl)sulfinyl)-
  4,5-diphenylimidazole;
5-(((4,5-diphenyl-2-oxazolyl)sulfinyl)methyl)-2,2-
  dimethyl-8-methyl-4H-1,3-dioxino(4,5-c) pyridine;
5-(((3,5-dimethyl-4-methoxy-2-pyridyl)methyl)sulfinyl)-
  1-methyltetrazole;
6-benzoylamino-7-chloro-2-(((3,5-dimethyl-4-methoxy-
  2-pyridyl)-methyl)thio)benzothiazole;
2-[[(3,5-dimethyl-4-methoxy-2-pyridyl)-methyl]thio]
  quinoline;
2-[2-(3,5-dimethyl)pyridylmethylsulfinyl]-5-methoxy-
  imidazo[4,5-b]pyridine;
5-(4,5-dihydro-2-oxazolyl)-2-((3,5-dimethyl-4-methoxy-
  2-pyridyl)methylthio)-1H-benzimidazole;
2-(2-dimethylaminobenzylsulfinyl)-5-methoxyimidazo
  [4,5-b]-pyridine;
3-phenyl-2-(2-pyridylmethylsulfinyl)-4(3H)-
  quinazolinone;
4-amino-2-(2-pyridylmethylthio)quinazoline;
2-(4-morpholinyl-2-pyrimidinylmethylthio)thieno(3,4-d)
  imidazole;
8-[2'-(N,N-dimethylanily)methylthio]purine;
2-[2'-(N,N-dimethylanily)methylthio]thieno-(3,4-d)-
  imidazole;
2-(4-methoxy-2-picolinylthio)-1H-thieno[3,4-d]
  imidazole;
2-(2-pyridylmethyl)thio-8H-indeno(1,2-d)imidazole;
2-(4-methoxy-5-chloro-2-picolythio)-1H-thieno(3,4-d)
  imidazole;
2-[2-(1-pyrrolidinyl)benzylthio]cycloheptoimidazole;
2-(2-acetylaminophenyl)methylthiocycloheptoimidazole;
2-amino-5-(2-(2-pyridyl)ethylthio)-1,3,4-thiadiazole;
2-gernaylthio-benzimidazole;
2-(2-chlorobenzylthio)-8,8-dimethyl-6-oxo-5,6,7,8-
  tetrahydro-3H-imidazo[4,5-g]quinoline;
8-(2-pyrimidinyl-sulfinyl)quinoline;
2-((3-methyl-2-pyridyl)methylsulfinyl)pyrano(2,3-f)
  benzimidazole;
2-[(2-isobutylamino)benzylsufinyl]imidazole; ethyl
  2-((1H-benzimidazol-2-yl)-sulfinylmethyl)-
  4dimethylamino-5-pyrimidinecarboxylate;
2-((2-ethoxyethyl)sulfinyl)-4-(3-pyridyl)thiazole;
2-[2-(2-propynylamino)benzylsulfinyl]imidazole;
2-(2-(2-methoxyethylamino)benzylsulfinyl)imidazole;
1-(2-pyridyl)-2-(3-dimethylamino)benzylsulfinyl)
  imidazole;
2-(2-methylaminobenzylthio)-4,5,6,7-tetrahydro-1H-
  benzimidazole;
4,5-diphenyl-2-(2-pyridylmethyl)-thioimidazole;
4-phenyl-2-(2-pyridylmethyl)thioimidazole;
4,5-bis(4-methoxyphenyl)-2-(2-thienylthio)imidazole;
2-(3-chloro-2-pyridinylthiomethyl)-4,5-dihydro-1H-
  imidazole;

1-methyl-2-(2-pyrimidinylthiomethyl)-5-nitro-imidazole;
1-methyl-2-(2-pyridylsulfonylmethyl)-5-nitroimidazole;
1-methyl-2-(5-bromo-2-pyridylthiomethyl)-5-nitro-imidazole;
2-[(1H-benzimidazol-2-ylsulfinyl)methyl]benzenamine;
2-[(1H-benzimidazol-2-ylsulfinyl)methyl]N,N-dimethylbenzenamine;
N-[2-[(1H-benzimidazol-2-ylsulfinyl)methyl]phenyl]acetamide;
2-[[(4-methyl-1H-benzimidazol-2-yl)sulfinyl]methyl]benzenamine;
2-[[(5,6-dimethyl-1H-benzimidazol-2-yl)sulfinyl]methyl]benzenamine;
2-[[(5-methoxy-1H-benzimidazol-2-yl)sulfinyl]methyl]benzenamine;
methyl 2-[[(2-aminophenyl)methyl]sulfinyl]-5-methoxy-1H-benzimidazole-6-carboxylate;
2-[(1H-benzimidazol-2-ylsulfinyl)methyl]-4-chlorobenzenamine;
2-[(1H-benzimidazol-2-ylsulfinyl)methyl]-5chlorobenzenamine;
2-[(1H-benzimidazol-2-ylsulfinyl)methyl]-4-methoxybenzenamine;
2-[(1H-benzimidazol-2-ylsulfinyl)methyl]-6-methoxybenzenamine;
2-[(1H-benzimidazol-2-ylsulfinyl)methyl]-3-methylbenzenamine;
2-[(1H-benzimidazol-2-ylsulfinyl)methyl]-4-methylbenzenamine;
2-[(1H-benzimidazol-2-ylsulfinyl)methyl]-6-methylbenzenamine;
2-[(1H-benzimidazol-2-ylsulfinyl)methyl]-4,6-dimethylbenzenamine;
2-[(1H-benzimidazol-2-ylsulfinyl)methyl]-N-methylbenzenamine;
2-[[(5-methoxy-1H-benzimidazol-2-yl)sulfinyl]methyl]-4-methylbenzenamine;
2-[[(5-methoxy-1H-benzimidazol-2-yl)sulfinyl]methyl]-6-methylbenzenamine;
2-[(1H-benzimidazol-2-ylsulfinyl)methyl]-4-ethylbenzenamine;
2-[(1H-benzimidazol-2-ylsulfinyl)methyl]-6-ethylbenzenamine;
2-[(1H-benzimidazol-2-ylsulfinyl)methyl]-4-methoxy-3,5-dimethylbenzenamine;
2-[[(5-methyl-1H-benzimidazol-2-yl)sulfinyl]-methyl]benzenamine;
2-[[(5-chloro-1H-benzimidazol-2-yl)sulfinyl]-methyl]benzenamine;
2-[[(5-ethoxy-1H-benzimidazol-2-yl)sulfinyl]-methyl]benzenamine;
2-[[[(5-(trifluoromethyl)-1H-benzimidazol-2-yl]sulfinyl]methyl]benzenamine;
2-[(1H-benzimidazol-2-ylsulfinyl)methyl]-4-(trifluoromethyl)benzenamine;
2-[(1H-benzimidazol-2-ylsulfinyl)methyl]-4-butylbenzenamine;
2-[(1H-benzimidazol-2-ylsulfinyl)methyl]-5,6-dimethylbenzenamine;
2-[(1H-benzimidazol-2-ylsulfinyl)methyl]-3,6-dimethylbenzenamine;
2-[(1H-benzimidazol-2-ylsulfinyl)methyl]-4-chloro-6-methylbenzenamine;
2-[(1H-benzimidazol-2-ylsulfiny)methyl]-4-chloro-6-methoxy-3-methylbenzenamine;
2-[[(5-ethoxy-1H-benzimidazol-2-yl)sulfinyl]-methyl]-4-methylbenzenamine;
2-[[(5-methyl-1H-benzimidazol-2-yl)sulfinyl]-methyl]-5,6-dimethylbenzenamine;
2-[[[(5-(trifluoromethy)1-1H-benzimidazol-2-yl]sulfinyl]-3,6-dimethylbenzenamine;
2-[[[(5-(trifluoromethyl)1-1H-benzimidazol-2-yl]sulfinyl]methyl]-6-methoxybenzenamine;
methyl 2-amino-3-[(1H-benzimidazol-2-yl)sulfinyl)methyl]benzoate;
ethyl 4-amino-3-[(1H-benzimidazol-2-yl)sulfinyl)methyl]benzoate;
ethyl 4-amino-3-([(5-methoxy-1H-benzimidazol-2-yl)sulfinyl]methyl]benzoate;
2-[[5,6-dimethoxy-1H-benzimidazol-2-yl)sulfinyl]methyl]-4-methylbenzenamine;
2-[(1H-benzimidazol-2-ylsulfinyl)methyl]-4-fluorobenzenamine;
2-[(1H-benzimidazol-2-ylsulfinyl)methyl]-3,4,5-trimethylbenzenamine;
2-[[(5-methoxy-1H-benzimidazol-2-yl)sulfinyl]methyl]-4-methoxy-3,5-dimethylbenzenamine;
3-[(1H-benzimidazol-2-ylsulfinyl)methyl]benzenamine;
3-[(1H-benzimidazol-2-ylsulfinyl)methyl]-2-pyridinamine;
3-[(1H-benzimidazol-2-ylsulfinyl)methyl]-N,N-dimethyl-2-pyridinamine;
6-[(1H-benzimidazol-2-ylsulfinyl)methyl]-2-pyridinamine;
6-[[(4-methyl-1H-benzimidazol-2-yl)-sulfinyl]methyl]-2-pyridinamine;
6-[[(5-methyl-1H-benzimidazol-2-yl)-sulfinyl]methyl]-2-pyridinamine;
6-[[(5-methoxy-1H-benzimidazol-2-yl)sulfinyl]-methyl]-2-pyridinamine;
6-[[(5-chloro-1H-benzimidazol-2-yl)-sulfinyl]methyl]-2-pyridinamine;
6-[[[5-(trifluoromethyl)-1H-benzimidazol-2-yl]sulfinyl]methyl]-2-pyridinamine;
6-[[(5-ethoxy-1H-benzimidazol-2-yl)-sulfinyl]methyl]-2-pyridinamine;
6-[[(5,6-dimethoxy-1H-benzimidazol-2-yl)-sulfinyl]methyl]-2-pyridinamine;
6-[[(5,6-dimethyl-1H-benzimidazol-2-yl)-sulfinyl]methyl]-2-pyridinamine;
6-[[(4,6-dimethyl-1H-benzimidazol-2-yl)-sulfinyl]methyl]-2-pyridinamine;
6-[[([5-(hydroxymethyl)-1H-benzimidazol-2-yl]sulfinyl]methyl]-2-pyridinamine;
6-[(1H-benzimidazol-2-ylsulfinyl)methyl]-N-(2,2-dimethylpropyl)-2-pyridinamine;
6-[(1H-benzimidazol-2-ylsulfinyl)methyl]-N-ethyl-2-pyridinamine; and
5-[(1H-benzimidazol-2-ylsulfinyl)methyl]-2-pyridinamine.

Within Formula I there is a subclass of compounds of high interest which can be used to treat a subject with a viral infection, represented by Formula II:

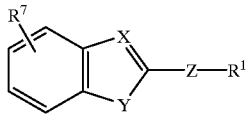

wherein X is selected from CH or N; wherein Y is selected from $CH_2$, $NR^8$, O and S; wherein Z is selected from $—S(O)_m—$, $—(CR^3R^4)_pS(O)_m—$ and $—S(O)_m(CR^5R^6)_n—$; wherein each of m, n and p is a number independently selected from 0, 1 and 2; wherein $R^1$ is selected from aryl and heteroaryl, wherein $R^1$ is optionally substituted at a substitutable position with one or more radicals selected from alkoxy, aminoalkoxy optionally substituted on the nitrogen atom with alkyl, cycloalkyl and aralkyl, cyano, nitro, hydroxyl, alkyl, halo, haloalkyl, haloalkoxy, cycloalkylalkoxy, carboxyl, acyl, alkanoyl, amide, alkylamide, aralkoxy, alkenyloxy, alkynyloxy, sulfonamidyl, dialkylsulfonamidyl, heterocyclic, aralkyl, heteroaralkyl, alkoxycarbonyl, heteroaryl, alkylthio, alkylsulfinyl, alkylsulfonyl, alkenylthio, arylthio, aralkylthio, cycloalkylthio, alkylimino and amino optionally substituted with a radical selected from alkyl, aralkyl, aryl, alkenyl, alkynyl, cycloalkyl, acyl, cycloalkenyl, hydroxyalkyl, alkoxycarbonyl and alkoxyalkyl; wherein each of $R^3$, $R^4$, $R^5$ and $R^6$ is independently selected from hydrido, alkyl, aryl and aralkyl; wherein $R^7$ is one or more radicals selected from alkoxy, amino, cyano, nitro, hydroxyl, alkyl, cycloalkyl, halo, haloalkyl, haloalkoxy, carboxyl, acyl, alkanoyl, acyl, alkylamino, arylamino, alkylarylamino, alkanoylamino, alkylaminoalkyl, amide, alkylamide, alkoxycarbonyl, aryloxycarbonyl, aralkoxycarbonyl, alkylcarbonyl, cycloalkylcarbonyl, alkylcarbonylalkyl, alkoxycarbonylalkyl, dialkylcarbamoyl, carbamoyloxy, aryloxy, aralkoxy, alkenyloxy, alkynyloxy, acyloxy, cycloalkylalkoxy, aralkyl, aryl, aroyl, alkoxyalkyl, hydroxyalkyl, heterocyclic, heteroaralkyl, alkylthio, alkylsulfinyl, alkylsulfonyl, arylthio, arylsulfinyl, alkylsulfonyl, sulfonamidyl and alkylsulfonamidyl; or wherein $R^5$ and $R^8$ taken together form a ring; and wherein $R^8$ is selected from hydrido, alkyl, alkenyl, hydroxyalkyl, acyl, alkoxyalkyl, aryl, aryloxyalkyl, alkylthioalkyl, aralkyl, alkoxycarbonyl, amide, alkanoyl, alkylcarbamoyl and alkylsulfonyl; provided that when m is 0, $R^8$ is not 1-(β-D-ribofuranosyl)benzimidazole; or a pharmaceutically acceptable salt thereof.

A preferred class of compounds consists of those compounds of Formula II wherein $R^1$ is selected from phenyl, naphthyl, thiazolyl, thiazolinyl, thiadiazolyl, oxazolyl, isoxazolyl, pyrazolyl, imidazolyl, imidazolinyl, pyridyl, quinolyl, dihydroquinolyl, tetrahydroquinolyl, isoquinolyl, azaquinolyl, azaisoquinolyl, tetrahydroisoquinolyl, thiatetrahydroisoquinolyl, imidazopyridyl, azachromanyl, cycloheptenopyridine, benzimidazolyl, benzothiazolyl, benzoxazinyl, pyridazinyl, purinyl, thienyl, furyl, azaimidazopyridyl, piperidyl, thienopyridinyl, dihydrothienopyridinyl, carbostyryl, pyrimidyl and pyrazinyl, wherein $R^1$ is optionally substituted at a substitutable position with one or more radicals selected from lower alkoxy, lower aminoalkoxy optionally substituted on the nitrogen atom with lower alkyl, lower cycloalkyl and lower aralkyl, cyano, nitro, hydroxyl, lower alkyl, halo, lower haloalkyl, lower haloalkoxy, lower cycloalkylalkoxy, carboxyl, acyl, lower alkanoyl, amide, lower alkylamide, lower aralkoxy, lower alkenyloxy, lower alkynyloxy, sulfonamidyl, lower dialkylsulfonamidyl, 5 to 20 membered heterocyclic, lower aralkyl, lower heteroaralkyl, lower alkoxycarbonyl, 5 to 8 membered heteroaryl, lower alkylthio, lower alkylsulfinyl, lower alkylsulfonyl, lower alkenylthio, lower arylthio, lower aralkylthio, lower cycloalkylthio, lower alkylimino and amino optionally substituted with a radical selected from lower alkyl, lower aralkyl, phenyl, lower alkenyl, lower alkynyl, lower cycloalkyl, acyl, lower cycloalkenyl, lower hydroxyalkyl, lower alkoxycarbonyl and lower alkoxyalkyl; wherein each of $R^3$, $R^4$, $R^5$ and $R^6$ is independently selected from hydrido, lower alkyl, phenyl, naphthyl and lower aralkyl; wherein $R^7$ is one or more radicals selected from lower alkoxy, amino, cyano, nitro, hydroxyl, lower alkyl, lower cycloalkyl, halo, lower haloalkyl, lower haloalkoxy, carboxyl, lower alkanoyl, acyl, lower alkylamino, lower arylamino, lower alkylarylamino, lower alkanoylamino, lower alkylaminoalkyl, amide, lower alkylamide, lower alkoxycarbonyl, lower aryloxycarbonyl, lower aralkoxycarbonyl, lower alkylcarbonyl, lower cycloalkylcarbonyl, lower alkylcarbonylalkyl, lower alkoxycarbonylalkyl, lower dialkylcarbamoyl, carbamoyloxy, lower aryloxy, lower aralkoxy, lower alkenyloxy, lower alkynyloxy, acyloxy, lower cycloalkylalkoxy, lower aralkyl, optionally substituted lower aryl, lower aroyl, lower alkoxyalkyl, lower hydroxyalkyl, 5 to 20 membered heterocyclic, lower heteroaralkyl, lower alkylthio, lower alkylsulfinyl, lower alkylsulfonyl, lower arylthio, lower arylsulfinyl, lower arylsulfonyl, sulfonamidyl and lower alkylsulfonamidyl; or wherein $R^5$ and $R^8$ taken together form a ring; and wherein $R^8$ is selected from hydrido, lower alkyl, lower alkenyl, lower hydroxyalkyl, acyl, lower alkoxyalkyl, phenyl, naphthyl, lower aryloxyalkyl, lower alkylthioalkyl, aralkyl, lower alkoxycarbonyl, amide, lower alkanoyl, lower alkylcarbamoyl and lower alkylsulfonyl.

A class of compounds of particular interest consists of those compounds of Formula II wherein $R^1$ is optionally substituted at a substitutable position with one or more radicals selected from methoxy, ethoxy, propoxy, butoxy, isopropoxy, tert-butoxy, aminomethoxy optionally substituted on the nitrogen atom with methyl, ethyl, propyl, butyl, pentyl, isopropyl, isobutyl, tert-butyl, cyclohexyl, cyclopropyl and benzyl, amino optionally substituted with a radical selected from methyl, ethyl, propyl, butyl, pentyl, isopropyl, isobutyl, tert-butyl, benzyl, phenethyl, phenyl, butene, pentene, isopropylene, isobutylene, propargyl, cyclopropyl, cyclobutyl, cyclopentyl, cyclohexyl, formyl, acetyl, cyclobutenyl, cyclopentenyl, cyclohexenyl, hydroxymethyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, and methoxymethyl, cyano, nitro, hydroxyl, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, cyclohexylmethoxy, carboxyl, formyl, acetyl, propionyl, amide, methylamide, dimethylamide, benzyloxy, sulfonamidyl, dimethylsulfonamidyl, morpholinyl, pyrrolidinyl, piperazinyl, piperidyl, benzyl, methoxycarbonyl, ethoxycarbonyl, pyridyl, methylthio, methylsulfinyl, methylsulfonyl, phenylthio, benzylthio, cyclohexylthio and methylimino; wherein each of $R^3$, $R^4$, $R^5$ and R⁶ is independently selected from hydrido, methyl, ethyl, propyl, butyl, pentyl, isopropyl, isobutyl, tert-butyl, phenyl and benzyl; wherein R⁷ is one or more radicals selected from methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, cyclohexyl, cyclopropyl, cyclobutyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, trifluoromethoxy, trifluoroethoxy, carboxyl, formyl, acetyl, propionyl, butyryl, N-methylamino, N-ethylamino, N-propylamino, N-butylamino, N-tert-butylamino, N-pentylamino, N-hexylamino, N,N-dimethylamino, phenylamino, N-methyl-N-phenylamino, methylaminomethyl, amide, N-methylamide, N,N-dimethylamide, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, phenoxycarbonyl, benzyloxycarbonyl, methylcarbonyl, cyclohexylcarbonyl, methylcarbonylmethyl, methoxycarbonylmethyl, N,N-dimethylcarbamoyl, carbamoyloxy, phenoxy, benzoxy, benzyl, phenethyl, phenyl, benzoyl, methoxymethyl, hydroxymethyl, morpholinyl, pyrrolidinyl, piperazinyl, piperidyl, methylthio, ethylthio, methylsulfinyl, ethylsulfinyl, methylsulfonyl, phenylthio, phenylsulfinyl, phenylsulfonyl, sulfonamidyl, methylsulfonamidyl and N,N-dimethylsulfonamidyl; or wherein R⁵ and R⁸ taken together form a ring; and wherein R⁸ is selected from hydrido, methyl, ethyl, propyl, butyl, pentyl, isopropyl, isobutyl, tert-butyl, butene, pentene, isopropylene, isobutylene, hydroxymethyl, phenyl, naphthyl, phenoxymethyl, methylthiomethyl, benzyl, phenethyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, methoxymethyl, amide, formyl, acetyl, propionyl, butyryl, methylcarbamoyl and methylsulfonyl; or a pharmaceutically acceptable salt thereof.

A family of specific compounds of particular interest within Formula II consists of compounds, and their pharmaceutically acceptable salts, of the group selected from:

2-[[3-methylpyridin-2-ylmethyl]sulfinyl]-1H-phenyl benzimidazole;
2-[(imidazo[1,2-a]pyridin-3-ylmethyl)sulfinyl]-1H-benzimidazole;
2-[(imidazo[1,2-a]pyridin-3-ylmethyl)sulfinyl]-1H-benzimidazole;
2-[(imidazo[1,2-a]pyridin-3-ylmethyl)sulfinyl]-5-methyl-1H-benzimidazole;
2-[(imidazo[1,2-a]pyridin-3-ylmethyl)sulfinyl]-5-methoxy-1H-benzimidazole;
5-chloro-2-[(imidazo[1,2-a]pyridin-3-ylmethyl)sulfinyl]-1H-benzimidazole;
2-[(imidazo 1,2-a]pyridin-3-ylmethyl)sulfinyl]-5-trifluoromethyl-1H-benzimidazole;
2-[(imidazo[1,2-a]pyridin-8-ylmethyl)sulfinyl]-1H-benzimidazole;
2-[(imidazo[1,2-a]pyridin-8-ylmethyl)sulfinyl]-1H-benzimidazole;
2-[(imidazo[1,2-a]pyridin-8-ylmethyl)sulfinyl]-5-methoxy-1H-benzimidazole;
5-ethoxy-2-[(imidazo[1,2-a]pyridin-8-ylmethyl)sulfinyl]-1H-benzimidazole;
2-[(imidazo[1,2-a]pyridin-8-ylmethyl)sulfinyl]-4-methyl-1H-benzimidazole;
2-[(imidazo[1,2-a]pyridin-8-ylmethyl)sulfinyl]-5-methyl-1H-benzimidazole;
2-[(imidazo[1,2-a]pyridin-8-ylmethyl)sulfinyl]-5,6-dimethyl-1H-benzimidazole;
2-[(imidazo[1,2-a]pyridin-8-ylmethyl)sulfinyl]-5,6-dimethoxy-1H-benzimidazole;
5-chloro-2-[(imidazo[1,2-a]pyridin-8-ylmethyl)sulfinyl]-1H-benzimidazole;
2-[(imidazo[1,2-a]pyridin-8-ylmethyl)sulfinyl]-5-trifluoromethyl-1H-benzimidazole;
2-[(2,3-dimethylimidazo[1,2-a]pyridin-8-yl)methyl]sulfinyl]-1H-benzimidazole;
2-[[(3-methylimidazo[1,2-a]pyridin-8-yl)methyl]sulfinyl]-1H-benzimidazole;
2-[[(2-phenylimidazo[1,2-a]pyridin-8-yl)methyl]sulfinyl]-1H-benzimidazole;
2-[[(3-phenylimidazo[1,2-a]pyridin-8-yl)methyl]sulfinyl]-1H-benzimidazole;
2-[[(3-(4-nitrophenyl)imidazo[1,2-a]pyridin-8-yl)methyl]sulfinyl]-1H-benzimidazole;
2-[[[3-[3-(trifluoromethyl)phenyl]imidazo[1,2-a]pyridin-8-yl]methyl]sulfinyl]-1H-benzimidazole;
5-methyl-2-[[[3-[3-(trifluoromethyl)phenyl]imidazo[1,2-a]pyridin-8-yl]methyl]sulfinyl]-1H-benzimidazole;
5-chloro-2-[[[3-[3-(trifluoromethyl)phenyl]imidazo[1,2-a]pyridin-8-yl]methyl]sulfinyl]-1H-benzimidazole;
2-[[[3-[4-(trifluoromethyl)phenyl]imidazo 1,2-a]pyridin-8-yl]methyl]sulfinyl]-1H-benzimidazole;
5-chloro-2-[[[3-[4-(trifluoromethyl)phenyl]imidazo[1,2-a]pyridin-8-y1]methyl]sulfinyl]-1H-benzimidazole;
4-[8-[(1H-benzimidazol-2-ylsulfinyl)methyl]imidazo[1,2-a]pyridin-3-yl]benzoate;
2-[[[3-(4-chlorophenyl)imidazo[1,2-a]pyridin-8-yl]methyl]sulfinyl]-1H-benzimidazole;
2-[[[3-(4-methylphenyl)imidazo[1,2-a]pyridin-8-yl]methyl]sulfinyl]-1H-benzimidazole;
2-[(imidazo[1,2-a]pyridin-5-ylmethyl)sulfinyl]-1H-benzimidazole;
4,6-dimethyl-2-(((imidazo(1,2-a)pyridin-2-yl)methyl)thio)-1H-benzimidazole;
2-[3-methyl-4-(2-(N-benzyl-N-cyclohexylamino)-ethoxy)pyridyl]methylthio-1H-benzimidazole;
ethyl 2-[(1H-benzimidazol-2-yl)thiomethyl]-4-methyl-amino-5-pyrimidine carboxylate;
2-(5-fluoro-2-(4-methoxy-2-pyridyl)-phenylsulfinyl)-1H-benzimidazole;
5-difluoromethoxy-2-(((3,4-dimethoxy-2-pyridinyl)methyl)sulfinyl)-1H-benzimidazole;
2-(((4-difluoromethoxy-3-methyl-2-pyridyl)methylsulfinyl)benzimidazole;
2-((6-azachroman-5-ylmethyl)sulfinyl)-benzimidazole;
5-carbomethoxy-6-methyl-2-(((3,4-dimethoxy-2-pyridinyl)methyl)sulfinyl-1H-benzimidazole;
5-carbomethoxy-6-methyl-2-(((3,4-dimethoxy-2-pyridinyl)methyl)sulfinyl)-1H-benzimidazol-1-yl-methyl ethyl carbonate;
2-((3-methyl-4-(2,2,2-trifluoroethoxy)-2-pyridyl)methylsulfinyl)benzimidazole;
4-fluoro-2-(((4-methoxy-2-pyridinyl)methyl)sulfinyl-1H-benzimidazol-1-yl-methyl-ethylcarbonate;

2-[3-methyl-4-(1-benzyl-4-piperidyl) oxy-2-pyridyl]
methylthio-1H-benzimidazole;
2-(3-methyl-4-(2-(N-methyl-N-(4-methyl-benzyl)amino)
ethoxy)-2-pyridyl)methylsulfonyl-1H-benzimidazole;
2-(4-methoxy-6-methyl-2-pyrimidinyl)methylthio-1H-
benzimidazole;
5-chloro-2-(3,4-dimethoxy-2-pyridylmethylsulfinyl)-1H-
benzimidazole;
5-fluoro-2-(4-cyclopropylmethoxy-2-pyridylmethyl-
sulfinyl)-1H-benzimidazole;
4-fluoro-2-(4-methoxy-2-pyridylmethylsulfinyl)-1H-
benzimidazole;
2-(((4-methoxy-3,5-dimethyl-2-pyridyl)-methyl)-
sulfinyl)-5-methoxy-1H-benzimidazole;
5-hydroxymethyl-2-((3,5-dimethyl-4-methoxy-2-pyridyl)
methylthio-1H-benzimidazole;
2-(4-ethylthio-3-methylpyrid-2-yl-methyl)sulfinyl-
benzimidazole;
2-(((4-(2-benzyloxyethoxy)-3-methyl-2-pyridyl)
methylthio)benzimidazole;
2-[[2-[N-(2-hydroxyethyl)-N-methylamino]-5-methoxy]
benzylsulfinyl]benzimidazole;
2-(5-benzyl-4-chloro-6-methyl-2-pyrimidinyl)
methylthio-1H-benzimidazole;
5-carboethoxy-6-methyl-2-(((3-methyl-2-pyridyl)methyl)
sulfinyl)-1H-benzimidazole;
5-(2-benzimidazolylsulfinylmethyl)-3,4-dihydro-4-
methyl-2H-1,4-benzoxazine;
2-(3-methyl-4-(2-(N-benzyl-N-methylamino)ethoxy-2-
pyridyl)methylsulfinyl-1H-benzimidazole;
2-(3-methyl-4-(2-(1,2,3,4-tetrahydroisoquinolin-2-yl)-
ethoxy)-2-pyridyl)methylsulfinyl-1H-benzimidazole;
2-[1-(3,5-dimethylpyrazolyl)]methylthiobenzimidazole;
2-(3-chloro-4-methoxy-2-picolylthio)-5-methoxy-1H-
benzimidazole;
2-(4-(2-ethoxyethoxy)-3-methyl-2-pyridyl)
methylsulfinyl-1H-benzimidazole;
2-(3-methylthieno(2,3-c)pyridin-7-yl)methylsulfinyl)-
benzimidazole;
2-(2-dimethylamino-5-methoxybenzylsulfinyl)-5-
methoxy-benzimidazole;
2-(2-dimethylamino-5-methylbenzylsulfinyl)-5-
methoxybenzimidazole;
2-[4-(2,3,5-trimethyl)pyridylthio]-5-
methoxybenzimidazole;
2-[(2-(4-chlorophenyl)-5-methylimidazol-4-yl)
methylthio]benzimidazole;
2-(5-hydroxy-1H-benzimidazol-2-ylsulfinylmethyl)-N,
N-dimethylbenzenamine;
2-((6-methoxyisoquinolin-1-yl)methylsulfinyl)
benzimidazole;
3-(5-methoxy-1H-benzimidazol-2-yl)
thiomethylcarbostyril;
5-methoxy-2-(4-dimethylamino-5-fluoro-2-
pyridylmethylsulfinyl)-1H-benzimidazole;
2-(2-dimethylaminobenzylsulfinyl)-5-
cyclopropylmethoxybenzimidazole;
2-(3,5-dimethyl-2-pyridylmethylsulfinyl)-5-
cyclopropylmethoxy-benzimidazole;
2-[(2-(N-cyclohexyl-N-methylamino)benzylsulfonyl]
benzimidazole;
8-(5-fluoro-6-methoxy-2-benzimidazolyl)sulfinylmethyl-
1-ethyl-4-(N-methyl-N-allyl)amino-1,2,3,4-
tetrahydroquinoline;
2-(2-benzyloxycarbonylaminobenzylthio)benzimidazole;
2-(2-benzimidazolylmethylthio)pyrimidine;
5-acetyl-2-((2-dimethylaminobenzyl)sulfinyl)
benzimidazole;
2-((3,5-dimethyl-4-methoxy-2-pyridyl)methylsulfinyl)-
5-fluoro-1H-benzimidazole;
2-(3-pyridylmethylthio)-5-methoxybenzimidazole;
2-(2-methylaminobenzylsulfinyl)benzimidazole;
5-methoxy-2-(2-dimethylaminobenzylsulfinyl)-1H-
benzimidazole;
2-(3,4-dimethoxypyrid-2-ylmethylsulfinyl)-5-
trifluoromethyl-benzimidazole;
5-methoxy-2-(4-piperidino-2-
pyrimidinylmethylsulfinyl)-(1H)-benzimidazole;
2-[(2-(4-benzyloxy)-pyridylmethylsulfinyl]
benzimidazole;
4-allyloxy-8-(2-benzimidazolyl)thio-3-methyl-5,6,7,8-
tetrahydroquinoline;
2-[2-(4-methoxy-5-n-pentyl)-pyridylmethylthio]
benzimidazole;
2-(5-bromo-4-piperidino-2-pyridylmethylsulfinyl)-5-
methoxy-(1H)-benzimidazole;
2-((3,5-dimethyl-4-morpholinopyrid-2-yl)
methylsulfinyl)benzimidazole;
2-((2-pyridinylmethyl)sulfinyl)-1H-benzimidazole-1-
methanol;
2-((3,4-dihydro-2H-thieno(3,2-c)pyridinylmethyl)thio)-
1H-benzimidazole-1-methanol;
2-(4-isopropoxy-2-pyridyl)methylsulfinylbenzimidazole;
2-((4-fluorobenzyloxy-3-methyl-2-pyridyl)
methylsulfinyl)benzimidazole;
2-(2-aminobenzylsulfinyl)-benzimidazole;
N,N-dimethyl-2-(1H-benzimidazol-2-yl-sulfinylmethyl)
benzenamine;
2-[(4,5-dimethoxy-2-pyridyl)methylsulfinyl]-5-
trifluoromethoxy-1H-benzimidazole;
2-((4-morpholinyl-3-ethylpyridin-2-ylmethyl)sulfinyl)-5-
trifluoromethylbenzimidazole;
2-((4-methoxy-2-pyridyl)methylsulfinyl)-5-
trifluoromethoxy-1H-benzimidazole;
5-cyclopropylcarbonyl-2-((4-methoxy-2-pyridyl)methyl-
sulfinyl)-1H-benzimidazole;
2-[2-(3,5-dimethyl-4-methoxy)-pyridylmethylsulfinyl]-
(5-chloro)-benzimidazole;
2-[2-(4,5-dimethyl)-pyridylmethylsulfinyl]-(5-acetyl-6-
methyl)-benzimidazole;
2-[2-(3,5-dimethyl)pyridylmethylsulfinyl-]5-fluoro-
benzoxazole;
3-[(4-dimethylamino-2-pyridyl)methylthio]indole;
6-benzoylamino-7-chloro-2-(((3,5-dimethyl-4-
methoxy-2-pyridyl)-methyl)thio)benzothiazole;
5-(4,5-dihydro-2-oxazolyl)-2-((3,5-dimethyl-4-methoxy-
2-pyridyl)methylthio)-1H-benzimidazole;
2-gernaylthio-benzimidazole;
ethyl 2-((1H-benzimidazol-2-yl)-sulfinylmethyl)-4-
dimethylamino-5-pyrimidinecarboxylate;
2-[(1H-benzimidazol-2-ylsulfinyl)methyl]benzenamine;
2-[(1H-benzimidazol-2-ylsulfinyl)methyl]N,N-
dimethylbenzenamine;

N-[2-[(1H-benzimidazol-2-ylsulfinyl)methyl]phenyl] acetamide;

2-[[(4-methyl-1H-benzimidazol-2-yl)sulfinyl]methyl] benzenamine;

2-[[(5,6-dimethyl-1H-benzimidazol-2-yl)sulfinyl] methyl]benzenamine;

2-[[(5-methoxy-1H-benzimidazol-2-yl)sulfinyl]methyl] benzenamine;

methyl 2-[[(2-aminophenyl)methyl]sulfinyl]-5-methoxy-1H-benzimidazole-6-carboxylate;

2-[(1H-benzimidazol-2-ylsulfinyl)methyl]-4-chlorobenzenamine;

2-[(1H-benzimidazol-2-ylsulfinyl) methyl]-5-chlorobenzenamine;

2-[(1H-benzimidazol-2-ylsulfinyl)methyl]-4-methoxybenzenamine;

2-[(1H-benzimidazol-2-ylsulfinyl)methyl]-6-methoxybenzenamine;

2-[(1H-benzimidazol-2-ylsulfinyl)methyl]-3methylbenzenamine;

2-[(1H-benzimidazol-2-ylsulfinyl)methyl]-4-methylbenzenamine;

2-[(1H-benzimidazol-2-ylsulfinyl)methyl]-6-methylbenzenamine;

2-[(1H-benzimidazol-2-ylsulfinyl)methyl]-4,6-dimethylbenzenamine;

2-[(1H-benzimidazol-2-ylsulfinyl)methyl]-N-methylbenzenamine;

2-[[(5-methoxy-1H-benzimidazol-2-yl)sulfinyl]methyl]-4-methylbenzenamine;

2-[[(5-methoxy-1H-benzimidazol-2-yl)sulfinyl]methyl]-6-methylbenzenamine;

2-[(1H-benzimidazol-2-ylsulfinyl)methyl]-4-ethylbenzenamine;

2-[(1H-benzimidazol-2-ylsulfinyl)methyl]-6-ethylbenzenamine;

2-[(1H-benzimidazol-2-ylsulfinyl)methyl]-4-methoxy-3,5-dimethylbenzenamine;

2-[[(5-methyl-1H-benzimidazol-2-yl)sulfinyl]-methyl] benzenamine;

2-[[(5-chloro-1H-benzimidazol-2-yl)sulfinyl]-methyl] benzenamine;

2-[[(5-ethoxy-1H-benzimidazol-2-yl)sulfinyl]-methyl] benzenamine;

2-[[[(5-(trifluoromethyl)-1H-benzimidazol-2-yl] sulfinyl-]methyl]benzenamine;

2-[(1H-benzimidazol-2-ylsulfinyl)methyl]-4-(trifluoromethyl)benzenamine;

2-[(1H-benzimidazol-2-ylsulfinyl)methyl]-4-butylbenzenamine;

2-[(1H-benzimidazol-2-ylsulfinyl)methyl]-5,6-dimethylbenzenamine;

2-[(1H-benzimidazol-2-ylsulfinyl)methyl]-3,6-dimethylbenzenamine;

2-[(1H-benzimidazol-2-ylsulfinyl)methyl]-4-chloro-6-methylbenzenamine;

2-((1H-benzimidazol-2-ylsulfiny)methyl]-4-chloro-6-methoxy-3-methylbenzenamine;

2-[[(5-ethoxy-1H-benzimidazol-2-yl)sulfinyl]-methyl]-4-methylbenzenamine;

2-[[(5-methyl-1H-benzimidazol-2-yl)sulfinyl]-methyl]-5,6-dimethylbenzenamine;

2-[[[(5-(trifluoromethy)1-1H-benzimidazol-2-yl] sulfinyl]-3,6-dimethylbenzenamine;

2-[[[(5-(trifluoromethyl)1-1H-benzimidazol-2-yl] sulfinyl]methyl]-6-methoxybenzenamine;

methyl 2-amino-3-[(1H-benzimidazol-2-ylsulfinyl) methyl]benzoate;

ethyl 4-amino-3-[(1H-benzimidazol-2-ylsulfinyl)methyl] benzoate;

ethyl 4-amino-3-[[(5-methoxy-1H-benzimidazol-2-yl) sulfinyl]methyl]benzoate;

2-([5,6-dimethoxy-1H-benzimidazol-2-yl)sulfinyl] methyl]-4-methylbenzenamine;

2-[(1H-benzimidazol-2-ylsulfinyl)methyl]-4-fluorobenzenamine;

2-((1H-benzimidazol-2-ylsulfinyl)methyl]-3,4,5-trimethylbenzenamine;

2-[[(5-methoxy-1H-benzimidazol-2-yl)sulfinyl]methyl]-4-methoxy-3,5-dimethylbenzenamine;

3-[(1H-benzimidazol-2-ylsulfinyl)methyl]benzenamine;

3-[(1H-benzimidazol-2-ylsulfinyl)methyl]-2-pyridinamine;

3-[(1H-benzimidazol-2-ylsulfinyl)methyl]-N,N-dimethyl-2-pyridinamine;

6-[(1H-benzimidazol-2-ylsulfinyl)methyl]-2-pyridinamine;

6-[[(4-methyl-1H-benzimidazol-2-yl)-sulfinyl]methyl]-2-pyridinamine;

6-[[(5-methyl-1H-benzimidazol-2-yl)-sulfinyl]methyl]-2-pyridinamine;

6-[[(5-methoxy-1H-benzimidazol-2-yl)sulfinyl]methyl]-2-pyridinamine;

6-[[(5-chloro-1H-benzimidazol-2-yl)-sulfinyl]methyl]-2-pyridinamine;

6-[[[5-(trifluoromethyl)-1H-benzimidazol-2-yl]sulfinyl] methyl]-2-pyridinamine;

6-[[(5-ethoxy-1H-benzimidazol-2-yl)-sulfinyl]methyl]-2-pyridinamine;

6-[[(5,6-dimethoxy-1H-benzimidazol-2-yl)-sulfinyl] methyl]-2-pyridinamine;

6-[[(5,6-dimethyl-1H-benzimidazol-2-yl)-sulfinyl] methyl]-2-pyridinamine;

6-[[(4,6-dimethyl-1H-benzimidazol-2-yl)-sulfinyl] methyl]-2-pyridinamine;

6-[[[5-(hydroxymethyl)-1H-benzimidazol-2-yl]sulfinyl] methyl]-2-pyridinamine;

6-[(1H-benzimidazol-2-ylsulfinyl)methyl]-N-(2,2-dimethylpropyl)-2-pyridinamine;

6-[(1H-benzimidazol-2-ylsulfinyl)methyl]-N-ethyl-2-pyridinamine; and

5-[(1H-benzimidazol-2-ylsulfinyl)methyl]-2-pyridinamine.

Within Formula I there is a second subclass of compounds of high interest which can be used to treat viral infection by inhibiting viral proteases, represented by Formula III:

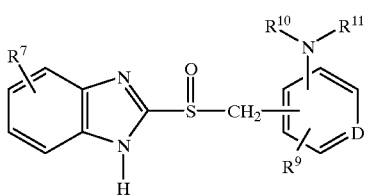

III wherein D is N or CH; wherein $R^7$ is one or more radicals selected from hydrido, alkoxy, amino, cyano, nitro, hydroxyl, alkyl, halo, haloalkyl, carboxyl, alkanoyl, nitro, amino, alkylamino, amide, alkylamide, alkoxycarbonyl, alkylthio, alkylsulfinyl and alkylsulfonyl; wherein $R^9$ is one or more radicals selected from hydrido, alkoxy, amino, alkyl, halo, cyano, nitro, hydroxyl, haloalkyl, carboxyl, alkanoyl, nitro, amino, alkylamino, amide, alkylamide, alkoxycarbonyl, alkylthio, alkylsulfinyl and alkylsulfonyl; and wherein $R^{10}$ and $R^{11}$ are independently selected from hydrido and alkyl; or a pharmaceutically acceptable salt thereof.

A preferred class of compounds consists of those compounds of Formula III wherein $R^7$ is one or more radicals selected from hydrido, lower alkoxy, amino, cyano, nitro, hydroxyl, lower alkyl, halo, lower haloalkyl, carboxyl, lower alkanoyl, lower alkylamino, amide, lower alkylamide, lower alkoxycarbonyl, lower alkylthio, lower alkylsulfinyl and lower alkylsulfonyl; wherein $R^9$ is one or more radicals selected from hydrido, lower alkoxy, amino, lower alkyl, halo, cyano, nitro, hydroxyl, lower haloalkyl, carboxyl, lower alkanoyl, lower alkylamino, amide, lower alkylamide, lower alkoxycarbonyl, lower alkylthio, lower alkylsulfinyl and lower alkylsulfonyl; and wherein $R^{10}$ and $R^{11}$ are independently selected from hydrido and lower alkyl; or a pharmaceutically acceptable salt thereof.

A class of compounds of particular interest consists of those compounds of Formula III wherein $R^7$ is one or more radicals selected from hydrido, methoxy, ethoxy, propoxy, butoxy, isopropoxy, tert-butoxy, amino, cyano, nitro, hydroxyl, methyl, ethyl, propyl, butyl, pentyl, isopropyl, isobutyl, tert-butyl, fluoro, chloro, bromo, iodo, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxyl, formyl, acetyl, propionyl, N-methylamino, N-ethylamino, N-propylamino, N-butylamino, N-tert-butylamino, N-pentylamino, N-hexylamino, N,N-dimethylamino, amide, N-methylamide, N,N-dimethylamide, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, methylthio, methylsulfinyl and methylsulfonyl; wherein $R^9$ is one or more radicals selected from hydrido, methoxy, ethoxy, propoxy, butoxy, isopropoxy, tert-butoxy, amino, methyl, ethyl, propyl, butyl, pentyl, isopropyl, isobutyl, tert-butyl, fluoro, chloro, bromo, iodo, cyano, nitro, hydroxyl, fluoromethyl, difluoromethyl, trifluoromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, carboxyl, formyl, acetyl, propionyl, N-methylamino, N-ethylamino, N-propylamino, N-butylamino, N-tert-butylamino, N-pentylamino, N-hexylamino, N,N-dimethylamino, amide, N-methylamide, N,N-dimethylamide, methoxycarbonyl, ethoxycarbonyl, isopropoxycarbonyl, tert-butoxycarbonyl, propoxycarbonyl, n-butoxycarbonyl, isobutoxycarbonyl, pentoxycarbonyl, methylthio, methylsulfinyl and methylsulfonyl; and wherein $R^{10}$ and $R^{11}$ are independently selected from hydrido, methyl, ethyl, propyl, butyl, pentyl, isopropyl, isobutyl and tert-butyl; or a pharmaceutically acceptable salt thereof.

A family of specific compounds of particular interest within Formula III consists of compounds, and their pharmaceutically acceptable salts, of the group selected from:

2-[(1H-benzimidazol-2-ylsulfinyl)methyl]benzenamine;

2-[(1H-benzimidazol-2-ylsulfinyl)methyl]N,N-dimethylbenzenamine;

N-[2-[(1H-benzimidazol-2-ylsulfinyl)methyl]phenyl]acetamide;

2-[[(4-methyl-1H-benzimidazol-2-yl)sulfinyl]methyl]benzenamine;

2-[[(5,6-dimethyl-1H-benzimidazol-2-yl)sulfinyl]methyl]benzenamine;

2-[[(5-methoxy-1H-benzimidazol-2-yl)sulfinyl]methyl]benzenamine;

methyl 2-[[(2-aminophenyl)methyl]sulfinyl]-5-methoxy-1H-benzimidazole-6-carboxylate;

2-[(1H-benzimidazol-2-ylsulfinyl)methyl]-4-chlorobenzenamine;

2-[(1H-benzimidazol-2-ylsulfinyl)methyl]-5-chlorobenzenamine;

2-[(1H-benzimidazol-2-ylsulfinyl)methyl]-4-methoxybenzenamine;

2-[(1H-benzimidazol-2-ylsulfinyl)methyl]-6-methoxybenzenamine;

2-[(1H-benzimidazol-2-ylsulfinyl)methyl]-3-methylbenzenamine;

2-[(1H-benzimidazol-2-ylsulfinyl)methyl]-4-methylbenzenamine;

2-[(1H-benzimidazol-2-ylsulfinyl)methyl]-6-methylbenzenamine;

2-[(1H-benzimidazol-2-ylsulfinyl)methyl]-4,6-dimethylbenzenamine;

2-[(1H-benzimidazol-2-ylsulfinyl)methyl]-N-methylbenzenamine;

2-[[(5-methoxy-1H-benzimidazol-2-yl)sulfinyl]methyl]-4-methylbenzenamine;

2-[[(5-methoxy-1H-benzimidazol-2-yl)sulfinyl]methyl]-6-methylbenzenamine;

2-[(1H-benzimidazol-2-ylsulfinyl)methyl]-4-ethylbenzenamine;

2-[(1H-benzimidazol-2-ylsulfinyl)methyl]-6-ethylbenzenamine;

2-[(1H-benzimidazol-2-ylsulfinyl)methyl]-4-methoxy-3,5-dimethylbenzenamine;

2-[[(5-methyl-1H-benzimidazol-2-yl)sulfinyl]-methyl]benzenamine;

2-[[(5-chloro-1H-benzimidazol-2-yl)sulfinyl]-methyl]benzenamine;

2-[[(5-ethoxy-1H-benzimidazol-2-yl)sulfinyl]-methyl]benzenamine;

2-[[[(5-(trifluoromethyl)-1H-benzimidazol-2-yl]sulfinyl]methyl]benzenamine;

2-[(1H-benzimidazol-2-ylsulfinyl)methyl]-4-(trifluoromethyl)benzenamine;

2-[(1H-benzimidazol-2-ylsulfinyl)methyl]-4-butylbenzenamine;

2-[(1H-benzimidazol-2-ylsulfinyl)methyl]-5,6-dimethylbenzenamine;

2-[(1H-benzimidazol-2-ylsulfinyl)methyl]-3,6-dimethylbenzenamine;

2-[(1H-benzimidazol-2-ylsulfinyl)methyl]-4-chloro-6-methylbenzenamine;

2-[(1H-benzimidazol-2-ylsulfiny)methyl]-4-chloro-6-methoxy-3-methylbenzenamine;

2-[[(5-ethoxy-1H-benzimidazol-2-yl)sulfinyl]-methyl]-4-methylbenzenamine;

2-[[(5-methyl-1H-benzimidazol-2-yl)sulfinyl]-methyl]-5,6-dimethylbenzenamine;

2-[[[(5-(trifluoromethy)1-1H-benzimidazol-2-yl]sulfinyl]-3,6-dimethylbenzenamine;

2-[[[(5-(trifluoromethy)1-1H-benzimidazol-2-yl]sulfinyl]methyl]-6-methoxybenzenamine;

methyl 2-amino-3-[(1H-benzimidazol-2-yl)sulfinyl)methyl]benzoate;

ethyl 4-amino-3-[(1H-benzimidazol-2-yl)sulfinyl)methyl]benzoate;

ethyl 4-amino-3-[[(5-methoxy-1H-benzimidazol-2-yl)sulfinyl]methyl]benzoate;

2-[[5,6-dimethoxy-1H-benzimidazol-2-yl)sulfinyl]methyl]-4-methylbenzenamine;

2-[(1H-benzimidazol-2-ylsulfinyl)methyl]-4-fluorobenzenamine;

2-[(1H-benzimidazol-2-ylsulfinyl)methyl]-3,4,5-trimethylbenzenamine;

2-[[(5-methoxy-1H-benzimidazol-2-yl)sulfinyl]methyl]-4-methoxy-3,5-dimethylbenzenamine;

3-[(1H-benzimidazol-2-ylsulfinyl)methyl]benzenamine;

3-[(1H-benzimidazol-2-ylsulfinyl)methyl]-2-pyridinamine;

3-[(1H-benzimidazol-2-ylsulfinyl)methyl]-N,N-dimethyl-2-pyridinamine;

6-[(1H-benzimidazol-2-ylsulfinyl)methyl]-2-pyridinamine;

6-[[(4-methyl-1H-benzimidazol-2-yl)-sulfinyl]methyl]-2-pyridinamine;

6-[[(5-methyl-1H-benzimidazol-2-yl)-sulfinyl]methyl]-2-pyridinamine;

6-[[(5-methoxy-1H-benzimidazol-2-yl)sulfinyl]methyl]-2-pyridinamine;

6-[[(5-chloro-1H-benzimidazol-2-yl)-sulfinyl]methyl]-2-pyridinamine;

6-[[[5-(trifluoromethyl)-1H-benzimidazol-2-yl]sulfinyl]methyl]-2-pyridinamine;

6-[[(5-ethoxy-1H-benzimidazol-2-yl)-sulfinyl]methyl]-2-pyridinamine;

6-[[(5,6-dimethoxy-1H-benzimidazol-2-yl)-sulfinyl]methyl]-2-pyridinamine;

6-[[(5,6-dimethyl-1H-benzimidazol-2-yl)-sulfinyl]methyl]-2-pyridinamine;

6-[[(4,6-dimethyl-1H-benzimidazol-2-yl)-sulfinyl]methyl]-2-pyridinamine;

6-[[[5-(hydroxymethyl)-1H-benzimidazol-2-yl]sulfinyl]methyl]-2-pyridinamine;

6-[(1H-benzimidazol-2-ylsulfinyl)methyl]-N-(2,2-dimethylpropyl)-2-pyridinamine;

6-[(1H-benzimidazol-2-ylsulfinyl)methyl]-N-ethyl-2-pyridinamine; and

5-[(1H-benzimidazol-2-ylsulfinyl)methyl]-2-pyridinamine.

The invention also involves a method of treating viral infection in a subject with an effective amount of a protease inhibitor. Preferably, the subject is treated with a herpesvirus protease inhibitor. More preferred is a method wherein the viral protease inhibitor is a CMV protease inhibitor. Even more preferred is a method wherein the subject is treated with an inhibitor of CMV protease, encoded by $U_L 80$.

The invention further involves a method of treating a subject having a viral infection with a effective amount of a composition containing an $(H^+/K^+)$ATPase inhibitor and another anti-viral compound. preferably, the composition contains an $(H^+/K^+)$ATPase inhibitor and a virus-specific protease inhibitor. More preferably, the inhibitor is a serine protease inhibitor. An adjunct therapy utilizing compounds of this invention is one having a combination of an $(H^+/K^+)$ATPase inhibitor and an antibiotic.

Where the term "alkyl" is used, either alone or within other terms such as "haloalkyl", "alkylsulfonyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" denotes linear or branched radicals having two to about twenty carbon atoms or, preferably, two to about twelve carbon atoms. More preferred alkenyl radicals are "lower alkenyl" radicals having two to about ten carbon atoms. Most preferred are lower alkenyl radicals having two to about six carbon atoms. Examples of such radicals include ethylene, n-propylene, isopropylene, n-butylene, isobutylene, , pentene, hexene and the like. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having one to about six carbon atoms. Examples of such radicals include propargyl, butynyl, and the like. The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. The term "cycloalkylalkoxy" embrace cyclic oxy-containing radicals each having cycloalkyl portions of three to about ten carbon atoms. More preferred cycloalkylalkoxy radicals are "lower cycloalkylalkoxy" radicals having three to six carbon atoms. Examples of such radicals include cyclopropoxy, cyclobutoxy and cyclohexyloxy. The term "alkenyloxy" and embrace linear or branched oxy-containing radicals each having alkenyl portions of two to about ten carbon atoms. More preferred alkenyloxy radicals are "lower alkenyloxy" radicals having two to six carbon atoms. Examples of such radicals include propenoxy and butenoxy. The term "alkynyloxy" embrace linear or branched oxy-containing radicals each having alkynyl portions of two to about ten carbon atoms. More preferred alkynyloxy radicals are "lower alkynyloxy" radicals having two to six carbon atoms. Examples of such radicals include propargyloxy and pentynyloxy. The term "alkylthio" embraces radicals containing a linear or branched alkyl radical, of one to about ten carbon atoms attached to a divalent sulfur atom, such as a methythio radical, ($CH_3$—S—). The term "alkenylthio" embraces radicals containing a linear or branched alkenyl radical, of one to about ten carbon atoms attached to a divalent sulfur atom, such as a propenethio radical. The term "arylthio" embraces radicals containing a linear or branched aryl radical, of six to about ten carbon atoms attached to a divalent sulfur atom, such as a phenylthio radical. The term "aralkylthio" embraces radicals containing a linear or branched aralkyl radical attached to a divalent sulfur atom, such as a benzylthio radical. The term "cycloalkylthio" embraces radicals containing a linear or branched cycloalkyl radical, of three to about ten carbon atoms attached to a divalent sulfur atom, such as a cyclohexylthio radical. The term "alkylsulfinyl" embraces radicals containing a linear or branched alkyl radical, of one to ten carbon atoms, attached to a divalent —S(=O)— radical. "Arylsulfinyl" embraces aryl radicals attached to a sulfinyl radical, where aryl is defined below. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl" or "sulfonamidyl" denotes a sulfonyl radical substituted with an amine radical, forming a sulfonamide (—$SO_2NH_2$). The terms "alkylsulfonamidyl" and "dialkylsulfonamidyl" embrace radicals having one or two alkyl radicals, respectively, attached to a sulfonamidyl radical, where alkyl is defined as above. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronapthyl, indane and biphenyl. The "aryl" radicals may be further substituted with one or more halo, alkyl, nitro, cyano, haloalkoxy, alkoxy or amine radicals. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, thiazolinyl, dihydropyran, dihydrofuran, dihydroquinolyl, tetrahydroisoquinolyl, thiatetrahydroisoquinolyl, cycloheptenopyridine, benzoxazinyl, dihydrothienopyridinyl, tetrahydroquinolyl and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, purinyl, azaimidazopyridyl, benzimidazolyl, quinolyl, isoquinolyl, azaquinolyl, azaisoquinolyl, carbostyryl, imadazopyridyl, azachromanyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, thienopyridinyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. The term "heteraralkyl" or "heteroaralkyl" embraces heteroaryl-substituted alkyl radicals such as pyridylmethyl and thienylmethyl. The term "acyl" denotes a radical provided by the residue after removal of hydroxyl from an organic acid. Examples of such acyl radicals include alkanoyl and aroyl radicals. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(C=O)—. The term "alkylcarbonyl" means a radical containing an alkyl radical, as defined above, attached via an oxygen atom to a carbonyl radical. Examples of such "alkylcarbonyl" radicals include substituted or unsubstituted methylcarbonyl, ethylcarbonyl, propylcarbonyl, butylcarbonyl and hexylcarbonyl. The term "alkylcarbonylalkyl" denotes an alkyl radical substituted with an alkylcarbonyl radical as defined above. The term "cycloalkylcarbonyl" means a radical containing an cycloalkyl radical, as defined above, attached via an oxygen atom to a carbonyl radical. Examples of such "cycloalkylcarbonyl" radicals include substituted or unsubstituted cyclopropylcarbonyl, cyclobutylcarbonyl, cyclopentylcarbonyl and cyclohexylcarbonyl. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" embraces radicals having "alkoxycarbonyl", as defined above substituted to an alkyl radical. Examples of similar radicals include substituted or unsubstituted "aryloxycarbonyl" [e.g. phenoxycarbonyl, 4-nitrophenoxycarbonyl, 2-naphthyloxycarbonyl, etc.], substituted or unsubstituted "aralkoxycarbonyl" [e.g. benzyloxycarbonyl, phenethyloxycarbonyl, benzhydryloxycarbonyl, 4-nitrobenzyloxycarbonyl, etc.] and the like. The "alkanoyl" radicals may be a substituted or unsubstituted one such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The "aroyl" radicals may be benzoyl, naphthoyl, toluoyl, di(tert-butyl)benzoyl and the like and the aryl in said aroyl may be additionally substituted. The term "acyloxyl" denotes an acyl substituted oxygen atom, such as $CH_3CO_2$—. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl and cycloheptyl. The term "cycloalkenyl" embraces unsaturated radicals having three to ten carbon atoms, such as cylopropenyl, cyclobutenyl, cyclopentenyl, cyclohexenyl and cycloheptenyl. The term "aryloxy" embrace oxy-containing aryl radicals attached through an oxygen atom to other radicals. More preferred aryloxy radicals are "lower aryloxy" radicals having a phenyl radical. An example of such radicals is phenoxy. The term "aryloxyalkyl" embraces alkyl radicals having one or more aryloxy radicals attached to the alkyl radical, that is, to form monoaryloxyalkyl and diaryloxyalkyl radicals. The "aryloxy" or "aryloxyalkyl" radicals may be further substituted to provide haloaryloxyalkyl radicals alkylaryloxy radicals, and the like. Examples of such radicals include chlorophenoxy and methylphenoxy. The term "aralkyloxy" embrace oxy-containing aralkyl radicals attached through an oxygen atom to other radicals. The "aralkyloxy" radicals may be further substituted on the aryl ring portion of the radical. The term "aminoalkoxy" embraces alkoxy radicals substituted with amino radicals. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkylaminoalkyl" denotes an alkyl radical substituted with an alkylamino radical, as the terms are defined above. The term "alkanoylamino" denotes an amino radical substituted with an alkanoyl radical, as the terms are defined above. The term "arylamino" denotes amino groups which have been substituted with one or two aryl radicals, such as N-phenylamino. The term "aralkylamino" denotes amino groups which have been substituted with one or two aralkyl radicals, such as N-benzylamino, N-phenethylamino and phenpropylamino. The "aralkylamino" or "arylamino" radicals may be further substituted on the aryl ring portion of the radical. The term "N-alkyl-N-arylamino" denote amino radicals substituted with one alkyl and one aryl radical. The terms "amide" and "carbamoyl", whether used by themselves or with other terms such as "N-monoalkylamide", "N-monoarylamide", "N,N-dialkylamide", "N-alkyl-N-arylamide", "alkylcarbamoyl", "dialkylcarbamoyl" and "carbamoyloxy", denote a radical formed by an amino substituted carbonyl, or —C(=O)$NH_2$. The terms "alkylcarbamoyl" or "N-alkylamide" and "N,N-dialkylamide" or "dialkylcarbamoyl", denote amido groups which have been substituted with one alkyl radical and with two alkyl radicals, respectively. The N-alkylamide may be substituted with halo or an unsubstituted one such as N-methylamide, N-ethylamide, N-propylamide, N,N-dimethylamide, 2,2,2-trifluoroethylamide or the like. The terms "N-monoarylamide" and "N-alkyl-N-arylamide" denote amido radicals substituted, respectively, with one aryl radical, and one alkyl and one aryl radical. The N-arylamide may be phenylamide, naphthylamide, tolylamide, xylylamide, mesitylamide, cumenylamide, and the like, in which the preferable one is phenylamide. The term "carbamoyloxy" denote a radical formed by an oxy substituted carbamoyl , or —OC(=O)$NH_2$. The term "alkylimino" denotes imino groups (=NH) which have been substituted with an alkyl radical. Suitable "alkylimino" may be methylimino, ethylimino or the like.

Also included in the family of compounds of Formula I are isomeric forms including diastereomers, regioisomers, prodrugs and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

The invention is applicable to viral infections and is preferably for use in subjects infected with a DNA virus. More preferably, the method can be used for subjects infected with a herpesvirus, such as HSV-1, HSV-2, CMV, and the like.

GENERAL SYNTHETIC PROCEDURES

The compounds of this invention may be prepared by the methods illustrated in the following Schemes. Unless otherwise specified, the various substituents are defined as for Formula I–III, above.

Scheme I illustrates the preparation of sulfur-containing compounds of Formula I.

SCHEME I

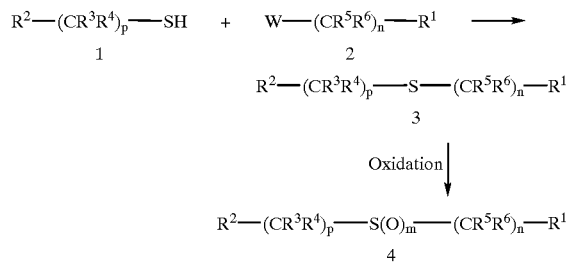

Thio compounds 3 are prepared by at least two routes, each of which uses a mercaptoheterocycle 1. In the preferred route, the mercaptoheterocycle 1 reacts with starting material 2, such as 2-aminobenzylhalide in which w is a halogen, and preferably chlorine or bromine. Typical conditions include reaction at room temperature in an organic solvent, such as absolute ethanol or dimethylformamide (DMF). For those compounds which form hydrohalide salts, the corresponding neutral compounds of 3 are readily obtained by methods known to those skilled in the art. For example, treating such a salt with base (such as aqueous potassium carbonate or preferably sodium hydroxide), followed by extraction into a non-protic organic solvent (such as dichloromethane or chloroform), gives the free base form of-3.

2-Aminobenzyl halides starting material 2, in which W is halogen, are obtained commercially or are prepared from corresponding 2-aminobenzyl alcohols 2, in which W is OH, or 2-methylsulfinylmethylanilines 2, in which W is CH$_3$SO, by synthetic methods well known in the art. For example, reaction of the alcohol with a halogenating reagent, such as thionyl chloride, phosphorus oxychloride, oxalyl chloride, and the like, in an inert organic solvent, such as dichloromethane or chloroform, will give corresponding 2-aminobenzyl chlorides as the hydrochloride salts. A preferred method involves treating the alcohol with hydrochloric or hydrobromic acid at temperatures between about room temperature and about 100° C. See B. Beilenson and F. M. Hamer, *J. Chem. Soc.*, 98–102 (1942).

Where an appropriate 2-aminobenzyl halide 2 is not readily available, thio compounds 3 may also be prepared by an acid-catalyzed reaction of the 2-mercaptoheterocycle 1 with compounds 2. Preferred conditions include heating a mixture of compounds 1 and 2 in glacial acetic acid containing excess (relative to 1 and 2)sulfuric acid. After quenching the reaction by pouring the mixture over ice, the thio compounds 3 are isolated by methods known in the art, including extraction, recrystallization and chromatography. Where an initially required 2-aminobenzyl alcohol 2 is not commercially available, corresponding 2-aminobenzoic acids or 2-aminobenzaldehydes may be reduced using methods known in the art, such as hydrogenation, reaction with lithium aluminum hydride, and the like. Various methods for preparing appropriate aminobenzoic acids are known. See, e.g., Baker et al., *J. Org. Chem.*, 17, 141–148, 149–156 (1952). Corresponding 2-nitrobenzyl alcohols or 2-nitrobenzaldehydes may also be reduced using methods known in the art, such as catalytic hydrogenation, to provide the 2-aminobenzyl alcohols.

The sulfoxide compounds 4 of this invention are prepared by oxidation of compounds 3 using methods known to those skilled in the art. Commonly used oxidizing agents include, for example, peracids, such as m-chloroperoxybenzoic acid; magnesium monoperoxyphthalate; peresters; peroxides, such as hydrogen peroxide; sodium metaperiodate; selenium dioxide; manganese dioxide; iodosobenzene; and the like. Preferred conditions for preparing sulfoxides 4 include oxidizing compounds 3 with an approximately equimolar quantity of m-chloroperoxybenzoic acid in an organic solvent, such as dichloromethane, at temperatures between about 0° C. and about room temperature. Oxidization may be terminated by adding dimethylsulfide.

Scheme II illustrates the preparation of sulfur-containing compounds 7 of Formula II.

SCHEME II

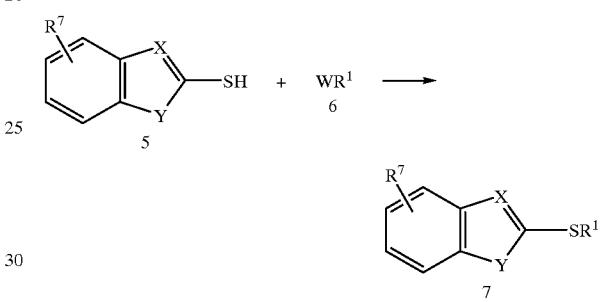

Benzimidazole compounds 7 of Formula II are prepared by at least two routes, similar to that of Scheme I, above, each using a 2-mercaptobenzimidazole 5. In the preferred route, the 2-mercaptobenzimidazole 5 reacts with starting material 6, such as 2-aminobenzyl halide in which W is a halogen, and preferably chlorine or bromine. Typical conditions include reaction at room temperature in an organic solvent such as absolute ethanol or DMF. For those compounds which form hydrohalide salts, the corresponding neutral compounds 7 of Formula II are readily obtained by methods known to those skilled in the art. For example, treating such a salt with base (such as aqueous potassium carbonate or sodium hydroxide), followed by extraction into a non-protic organic solvent (such as dichloromethane or chloroform), gives the free base form of 7.

The 2-aminobenzyl halides of 6, in which W is halogen, are obtained commercially or are prepared from corresponding 2-aminobenzyl alcohols, in which W is OH, or 2-methylsulfinylmethylanilines, in which W is CH$_3$SO, by synthetic methods well known in the art and described above in Scheme I.

Where an appropriate 2-aminobenzyl alcohol starting material 6 is not readily available, compounds of Formula II may also be prepared by an acid-catalyzed reaction of the 2-mercaptobenzimidazole 5 with 2-aminobenzyl alcohols as described above in Scheme I.

Scheme III illustrates the preparation of sulfoxide- and sulfonyl-containing compounds of Formula II.

Scheme III

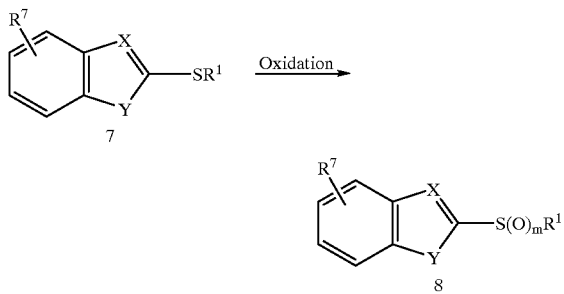

The sulfoxide and sulfonyl containing compounds of this invention are prepared by oxidation of benzimidazoles 7 of Formula II using methods known to those skilled in the art. Commonly used oxidizing agents include, for example, peracids, such as m-chloroperoxybenzoic acid; peresters; peroxides, such as hydrogen peroxide; sodium metaperiodate; selenium dioxide; manganese dioxide; iodosobenzene; and the like. Preferred conditions for preparing sulfoxides 8 include oxidizing benzimidazoles 7 of Formula II with an approximately equimolar quantity of m-chloroperoxybenzoic acid in an organic solvent, such as dichloromethane, at temperatures between about 0° C. and about room temperature. Oxidization may be terminated by adding dimethylsulfide.

Scheme IV illustrates the preparation of sulfoxide- and sulfonyl-containing compounds of Formula II.

Scheme IV

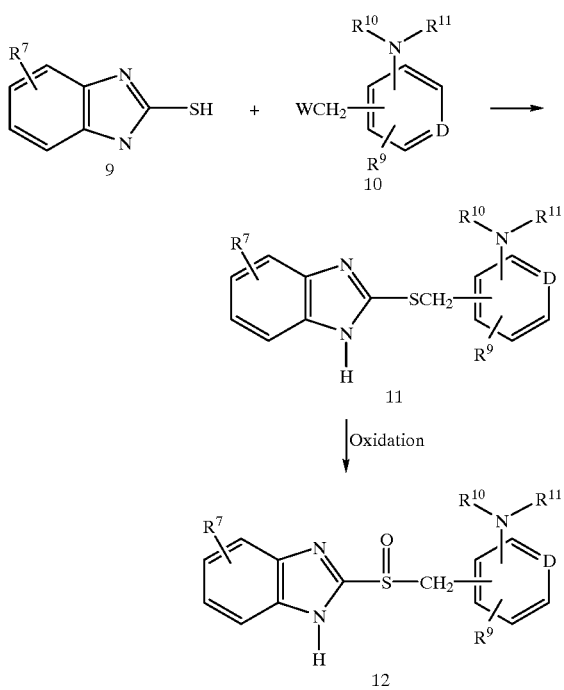

Thio compounds 11 are prepared by a route which uses 2-mercaptobenzimidazole 9. The 2-mercaptobenzimidazole 9 reacts with a 2-aminobenzyl halide or aminopyridyl halide 10 in which W is a halogen, preferably chlorine or bromine. Typical conditions include reaction at room temperature in an organic solvent such as absolute ethanol or isopropyl alcohol. For those compounds which form hydrohalide salts, the corresponding neutral compounds of 11 are readily obtained by methods known to those skilled in the art. For example, treating such a salt with base (such as aqueous potassium carbonate or preferably sodium hydroxide), followed by extraction into a non-protic organic solvent (such as dichloromethane or chloroform), gives the free base form of 11. The sulfoxide and sulfonyl containing compounds 12 of this invention are prepared by oxidation of 11 using methods as disclosed above in Scheme III.

Certain of the 2-amino compounds 9 are more conveniently prepared as phthalimide derivatives (that is, where $NR^{10}R^{11}$ is the phthalimide group) and used to prepare corresponding phthalimide derivatives of intermediates 10, as illustrated in the Examples.

Although treatment of such phthalimide derivatives with hydrazine in an alcohol would yield corresponding anilines (that is, intermediates 10 where $R^{10}$ and $R^{11}$ are both hydrogen), the preferred next step is oxidation (as described above) to corresponding phthalimide derivatives of sulfoxides 12. Treatment of the phthalimide derivatives of such sulfoxides with hydrazine hydrate in an alcohol, preferably methanol or ethanol, yields compounds 12 in which $R^{10}$ and $R^{11}$ are both hydrogen.

Although some of the 2-mercaptobenzimidazoles 9 are commercially available, others may be prepared by synthetic methods known to those skilled in the art. For example, Scheme V illustrates the preparation of 2-mercaptobenzimidazoles from substituted diaminobenzenes of 13.

Scheme V

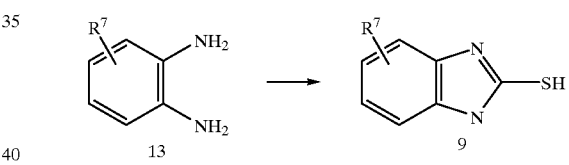

A preferred cyclization method employs an alkali metal alkylxanthate salt of the formula alkyl-O(C=O)S$^-$ M$^+$, where M$^+$ represents an alkali metal ion. Such an alkylxanthate salt may be preformed by methods known in the art or may be formed in situ by mixing an alkali metal hydroxide (preferably sodium hydroxide) and carbon disulfide in an alcohol (preferably ethanol). Preferred cyclization conditions include heating an aqueous or alcoholic mixture of a diaminobenzene 13 with sodium or potassium ethylxanthate at reflux under an inert atmosphere, such as argon.

Some of the derivatives of Formula I, to be used according to this invention, are the subject matter of the following patents and publications and can be obtained according to the preparation methods described therein.

The alkoxycarbonylalkylsulfinylthiazolo (5,4-b) pyridines of the Formula I can be prepared with the aid of the methods described in U.S. Pat. No. 5,079,255.

The alkoxyalkylsulfinylbenzothiazoles of the Formula I can be prepared with the aid of the methods described in EP 370,436.

The aminoethylthio-(1H)-benzimidazoles of Formula I can be prepared with the aid of the methods described in JP 3,014,566.

The imidazopyridinylalkylthio-1H-benzimidazoles and imidazopyridinylalkylsulfinyl-1H-benzimidazoles of the Formula I can be prepared with the aid of the methods described in U.S. Pat. Nos. 4,687,775 and 4,721,718 and WO 8,705,021.

The pyridylalkylthio-1H-benzimidazoles and pyridylalkylsulfinyl-1H-benzimidazoles of the Formula I can be prepared with the aid of the methods described in U.S. Pat. Nos. 5,049,674, 4,772,619, 5,019,584, 5,008,278, 5,045,552, 5,075,323, 5,124,158, 5,250,527, 4,753,955, 4,738,975, 4,727,150, 4,873,337, 4,758,579, 4,619,997, 4,555,518, 4,359,465, 4,255,431, 4,045,563, 4,818,760, WO 9,006,925, WO 9,119,711, WO 9,119,712, WO 8,903830, WO 8,900,566, DE 4,035,455, DE 3,415,971, EP 481,764, EP 475,456, EP 446,961, EP 298,440, EP 295,603, EP 184,322, EP 178,438, EP 167,943, JP 2,049,774, JP 3,052, 887, JP 3,048,680, JP 62,026,275, JP 63,183,577, JP 62,061, 978, JP 61,178,919, JP 61,085,383 and JP 5,117,268.

The benzylthio-1H-benzimidazoles, benzylthio-tetrahydro-1H-benzimidazoles and benzylsulfinyl-1H-benzimidazoles of the Formula I can be prepared with the aid of the methods described in U.S. Pat. No. 5,082,943, WO 8,701,114, EP 526,033, EP 251,536, EP 213,474, GB 2,161, 160, GB 2,163,747, JP 63,230,633, JP 63,208,579, JP 62,145,069, JP 62,185,078, JP 62,192,366, JP 62,207,261 and JP 1,230,560.

The pyrimidinylalkylthio-1H-benzimidazoles, pyrimidinylalkylsulfinyl-1H-benzimidazoles and pyrimidinylalkylsulfonyl-1H-benzimidazoles of Formula I can be prepared with the aid of that described in U.S. Pat. Nos. 4,791,114, 4,777,172, JP 1,132,581, JP 3,038,523, JP 5,262,763 and JP 5,112,559.

The pyridylalkylthio-dioxolobenzimidazoles and pyridylalkylthio-dioxolobenzimidazoles of the Formula I can be prepared with the aid of the methods described in U.S. Pat. Nos. 4,758,579 and 4,560,693 and WO 8,905,299.

The benzylsulfinylimidazylpyridines of Formula I can be prepared with the aid of the methods described in U.S. Pat. No. 4,933,458.

The pyridylalkylsulfinylquinoxalines of Formula I can be prepared with the aid of the methods described in U.S. Pat. No. 4,933,458 and JP 62,161,769.

The pyridylalkylsulfinylpyridopyrazines of Formula I can be prepared with the aid of the methods described in U.S. Pat. No. 4,933,458.

The benzimidazolyl-sulfinyl cycloalkylpyridines of Formula I can be prepared with the aid of the methods described in JP 4,364,127.

The azachromanylalkylsulfinylbenzimidazoles of Formula I can be prepared with the aid of the methods described in U.S. Pat. No. 5,077,407.

The benzimidazolylsulfinylalkyl-3,4-dihydrobenzoxazines can be prepared with the aid of the methods described in JO 1,022,873.

The pyrazolylalkylthiobenzimidazoles can be prepared with the aid of the methods described in JP 63,313,784.

The thienopyridinylalkylsulfinyl benzimidazoles can be prepared with the aid of the methods described in U.S. Pat. No. 4,839,365 and EP 176,308.

The benzimidazolylthioalkylcarbostyrils can be prepared with the aid of the methods described in JP 62,240,677.

The isoquinolinylalkylsulfinylbenzimidazoles of Formula I can be prepared with the aid of the methods described in U.S. Pat. No. 4,882,338.

The imidazolylalkylthiobenzimidazoles can be prepared with the aid of the methods described in JP 63,091,385.

The benzimidazolylsulfinylalkyl-1,2,3,4-tetrahydroquinolines of Formula I can be prepared with the aid of the methods described in U.S. Pat. Nos. 4,738,970 and 4,963,566.

The morpholinoalkylsulfinylbenzimidazoles of Formula I can be prepared with the aid of the methods described in U.S. Pat. No. 4,013,776.

The pyridyl-dihydro-thiazolobenzimidazoles of Formula I can be prepared with the aid of the methods described in U.S. Pat. No. 4,873,237.

The pyridylalkylthio-naphtho-imidazoles of Formula I can be prepared with the aid of the methods described in U.S. Pat. Nos. 4,182,766 and 4,435,406.

The pyridylalkylthio-tetrahydro-indeno imidazoles of Formula I can be prepared with the aid of the methods described in U.S. Pat. No. 4,435,406.

The benzylthio-imidazoquinolines, benzylsulfinyl-imidazoquinolines, pyridylalkylthio-imidazoquinolines and pyridylalkylsulfinyl-imidazoquinolines can be prepared with the aid of the methods described in U.S. Pat. Nos. 4,609,655 and 4,703,044 and JP 3,161,440.

The pyridylalkylthio-dihydro-indenoimidazolones and pyridylalkylsulfinyl-dihydro-indenoimidazolones of Formula I can be prepared with the aid of the methods described in U.S. Pat. No. 4,634,710.

The pyridylalkylthiocycloalkylimidazoles of Formula I can be prepared with the aid of the methods described in U.S. Pat. No. 4,735,955.

The aralkylalkylthiocycloalkylimidazoles of Formula I can be prepared with the aid of the methods described in JP 1,121,274 and JP 1,121,271.

The pyridylalkylsulfinylbenzoxazoles of Formula I can be prepared with the aid of the methods described in JP 61,140,582.

The pyridylalkylthioindoles of Formula I can be prepared with the aid of the methods described in U.S. Pat. No. 4,743,609.

The pyridylalkylthio-thienoimidazoles and pyridylalkylsulfinyl-thienoimidazoles of Formula I can be prepared with the aid of the methods described in U.S. Pat. Nos. 4,845,118, 5,049,566, WO 8,705,296, JP 1,040,468, EP 304,732 and EP 201,094.

Pyrimidinylalkylthio-thienoimidazoles of Formula I can be prepared with the aid of the methods described in U.S. Pat. No. 4,956,366.

Pyridylalkylsulfinylimidazopyridines and pyridylalkylthio-imidazopyridines of Formula I can be prepared with the aid of the methods described in U.S. Pat. Nos. 4,808,596 and 5,049,566, JP 1,190,682, JP 63,146,883 and JP 62,145,084.

Pyridylalkylthiobenzothiazoles of Formula I can be prepared with the aid of the methods described in JP 62,207, 271.

Pyridylalkylthioquinolines of Formula I can be prepared with the aid of the methods described in JP 62,209,062.

Pyrimidinylsulfinyl-quinolines of Formula I can be prepared with the aid of the methods described in U.S. Pat. No. 4,808,591.

Pyridylalkylsulfinyl-quinazolinones of Formula I can be prepared with the aid of the methods described in U.S. Pat. No. 4,833,144.

Pyridylalkylthioquinazolines of Formula I can be prepared with the aid of the methods described in JP 63,284, 172.

Pyridylalkylthio-thiadiazoles of Formula I can be prepared with the aid of the methods described in JP 1,233,282.

Alkenylthio-benzimidazoles of Formula I can be prepared with the aid of the methods described in U.S. Pat. No. 5,106,863.

Pyridylalkylsulfinyl-pyranobenzimidazoles of Formula I can be prepared with the aid of the methods described in JP 62,145,083.

Alkoxyalkylsulfinyl-thiazoles of Formula I can be prepared with the aid of the methods described in U.S. Pat. No. 5,171,746.

Benzylsulfinylimidazoles, pyridylsulfinyl imidazoles, benzylthioimidazoles and pyridylthio imidazoles of Formula I can be prepared with the aid of the methods described in U.S. Pat. Nos. 5,091,403, 3,905,985 and 4,528,298, EP 584588, DT 2,357,277, JP 62,187,469, JP 1,040,467, JP 2,049,727 and JP 3,148,262.

Pyrimidinylthioalkylimidazoles of Formula I can be prepared with the aid of the methods described in DT 2,403, 340.

Pyridinylthioalkyl-dihydro-1H-imidazoles of Formula I can be prepared with the aid of the methods described in U.S. Pat. No. 4,506,074.

Pyridylalkylthioheteraryls and pyridylalkylsulfinylheteroaryls of Formula I can be prepared with the aid of the methods described in JP 62,207,270.

Acid addition salts of this invention may be prepared during the course of the reactions (as described above), by ion exchange from those or other such salts using methods known in the art, or by acidification of free bases of the compounds. Base addition salts of this invention by methods known in the art, including those methods disclosed in British Pat. No. 2,137,616.

The following examples contain detailed descriptions of the methods of preparation of compounds of Formula I-III. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in degrees Centigrade unless otherwise indicated. Omeprazole can be made as described in U.S. Pat. No. 4,255,431.

EXAMPLE 1

2-[(1H-Benzimidazol-2-ylthio)methyl]-N,N-dimethylbenzenamine

A mixture of 2.20 g (14.6 mmole) of 2-mercaptobenzimidazole and 3.0 g (14.6 mmole) of 2-(chloromethyl)-N,N-dimethylaniline in 120 ml of absolute ethanol were stirred under nitrogen for about two hours. A solid (4.8 g) was collected by filtration, washed with ethanol, and air-dried. The solid was dissolved in water and made basic with potassium carbonate, then extracted into dichloromethane. The organic phase was dried over sodium sulfate, filtered, and concentrated in vacuo to dryness. Recrystallization from acetonitrile gave 2.3 g of a white solid (first crop). Concentration of the acetonitrile liquors gave 0.7 g of a second crop. The two crops were combined and recrystallized from isopropyl alcohol, giving the title compound as an analytically pure solid, m.p. 167–170° C. Analysis. Calc'd. for $C_{16}H_{17}N_3S$: C, 67.81; H, 6.05; N, 14.83; S, 11.31. Found: C, 67.84; H, 6.19; N, 14.73; S, 11.50.

EXAMPLE 2

2-[(1H-Benzimidazol-2-ylthio)methyl]benzenamine

A mixture of 9.0 g (60 mmole) of 2-mercaptobenzimidazole and 4.9 g (40 mmole) of 2-aminobenzyl alcohol were heated at 84° C. in a mixture of 45 ml of glacial acetic acid and 12.0 g (120 mmole) of sulfuric acid. After two hours an additional 1 g (8 mmole) of 2-aminobenzyl alcohol and 1 g of sulfuric acid were added. After one hour the reaction mixture was cooled and poured into cold benzenamine hemihydrate.

EXAMPLE 3

2-[(1H-Benzimidazol-2-ylsulfinyl)methyl]benzenamine

The title product of Example 2 (830 mg, 3.25 mmole) was dissolved in about 200 ml of boiling chloroform and then cooled to about −10° C. A solution of 662 mg (ca. 3.25 mmole) of ca. 85% m-chloroperoxybenzoic acid in 10 ml of chloroform was then added with stirring over about ten minutes. After another thirty minutes, the reaction was quenched with 4 drops of dimethylsulfide and a white solid was collected by filtration. The solid was washed sequentially with chloroform and diethyl ether, then air dried, giving 550 mg of the title compound: m.p. 164–165° C. Analysis. Calc'd. for $C_{14}H_{13}N_3OS*½$ H2O: C,59.98; H,5.03; N, 15.00; S, 11.44. Found: C, 60.11; H, 4.82; N, 14.93; S, 11.44.

EXAMPLE 4

2-[(1H-Benzimidazol-2-ylsulfinyl)methyl]N,N-dimethylbenzenamine

The title compound was prepared by the method of Example 3 using 1.5 g of the title product of Example 1 instead of the title product of Example 2. Recrystallization from diethyl ether gave 786 mg of the title compound: m.p. 107–109° C. Analysis. Calc'd. for $C_{16}H_{17}N_3OS$: C, 64.19; H, 5.72; N,14.04; S, 10.71. Found: C, 64.44; H, 5.83; N, 14.12; S, 11.06.

EXAMPLE 5

N-[(2-[(1H-Benzimidazol-2-ylthio)methyl]phenyl]acetamide

A solution of 10 g (81.3 mmole) of 2-aminobenzyl alcohol and 50 ml (ca. 530 mmole) of acetic anhydride was allowed to stand in 200 ml of pyridine for 20 hours. The solution was concentrated in vacuo and the resultant solid was washed with diethyl ether. The resultant diacetyl intermediate was collected as white needles. A mixture of 7.30 g (35.3 mmole) of the intermediate and 7.30 g (52.9 mmole) of potassium carbonate was stirred for 30 minutes in 300 ml of methanol. After removing insolubles by filtration, the filtrate was concentrated to give the N-acetyl intermediate. The material was suspended in 1 liter of dichloromethane to which was added 10 ml (ca. 137 mmole) of thionyl chloride. After 19 hours the reaction mixture was concentrated to dryness. Chloroform was added to the residue and then removed in vacuo to give crude N-(2-chloromethylphenyl)acetamide, which was used in the subsequent reaction without further purification. Using the method described in Example 1 with N-(2-chloromethylphenyl) acetamide instead of 2-(chloromethyl)-N,N-dimethylaniline produced 3.9 g of the title compound: m.p. 218–222° C. Analysis. Calc'd. for $C_{16}H_{15}N_3OS$: C, 64.62; H, 5.08; N,14.13; S, 10.78. Found: C, 64.20; H, 5.20; N, 14.02; S, 11.06.

EXAMPLE 6

N-[2-[(1H-Benzimidazol-2-ylsulfinyl)methyl]phenyl]acetamide

The title compound was prepared by the method of Example 3 using 1.80 g of the title product of Example 5 instead of the title product of Example 2. Trituration with diethylether gave 1.52 g of the title compound: m.p. 201–202.5° C. Analysis. Calc'd. for $C_{16}H_{15}N_3O_2S$: C, 61.32; H, 4.82; N, 13.41; S, 10.23. Found: C, 61.00; H, 4.90; N, 13.28; S, 10.50.

EXAMPLE 7

2-[[(4-Methyl-1H-benzimidazol-2-yl)thio]methyl]benzenamine

The title compound was prepared by the method of Example 1 using 3.52 g of 2-mercapto-4-methylbenzimidazole instead of 2-mercaptobenzimidazole and 3.52 g of 2-(chloromethyl) aniline hydrochloride instead of 2-(chloromethyl)-N,N-dimethylaniline. Recrystallization from diethyl ether gave 1.23 g of the title compound: m.p. 125–127° C. Analysis. Calc'd. for $C_{15}H_{15}N_3S$: C, 66.89; H, 5.61; N,15.60; S, 11.90. Found: C, 66.76; H, 5.62; N, 15.41; S, 11.87.

EXAMPLE 8

2-[[(4-Methyl-1H-benzimidazol-2-yl)sulfinyl]methyl]benzenamine hemihydrate

The title compound (740 mg) was prepared by the method of Example 3 using 900 mg of the title product of Example 7 instead of the title product of Example 2. Analysis. Calc'd. for $C_{15}H_{15}N_3OS \cdot \frac{1}{2} H_2O$: C, 61.20; H,5.48; N, 14.27; S, 10.89. Found: C, 61.21; H, 5.05; N, 13.88; S, 11.12.

EXAMPLE 9

2-[[(5,6-Dimethyl-1H-benzimidazol-2-yl)thio]methyl]benzenamine

The title compound was prepared by the method of Example 1 using 2.56 g of 5,6-dimethyl-2-mercaptobenzimidazole instead of 2-mercaptobenzimidazole and 2.56 g of 2-(chloromethyl) aniline hydrochloride instead of 2-(chloromethyl)-N,N-dimethylaniline. Instead of using sodium carbonate in an extraction, the crude precipitate was neutralized with triethylamine in methanol. Trituration of the resultant crude title compound with methanol and diethyl ether gave 2.0 g of analytically pure title compound. Analysis. Calc'd. for $C_{15}H_{15}N_3S$: C, 67.81; H, 6.05; N,14.83; S, 11.31. Found: C, 67.21; H, 6.16; N, 14.50; S, 11.06.

EXAMPLE 10

2-[[(5,6-Dimethyl-1H-benzimidazol-2-yl)sulfinyl]methyl]benzenamine ¼ hydrate The title compound, m.p. 179–181° C., was prepared by the method of Example 3 using 1.52 g of the title product of Example 9 instead of the title product of Example 2. Analysis. Calc'd. for $C_{16}H_{17}N_3OS \cdot \frac{1}{4} H_2O$: C, 63.24; H,5.80; N, 13.83; S, 10.55. Found: C, 62.80; H, 5.49; N, 13.53; S, 10.76.

EXAMPLE 11

2-[[(5-methoxy-1H-benzimidazol-2-yl)thio]methyl]benzenamine

The title compound was prepared by the method of Example 1 using 1.68 g (9.33 mmole) of 2-mercapto-5-methoxybenzimidazole instead of 2-mercaptobenzimidazole and 1.99 g (11.2 mmole) of 2-(chloromethyl)aniline hydrochloride instead of 2-(chloromethyl)-N,N-dimethylaniline in 250 ml of isopropyl alcohol. The basic extraction used 5% sodium hydroxide instead of sodium carbonate. Chromatography on silica gel, followed by crystallization from diethylether, gave 520 mg of pure title compound: m.p. 140–142° C. Analysis. Calc'd. for $C_{15}H_{15}N_3OS$: C, 63.14; H, 5.30; N,14.73; S, 11.23. Found: C, 63.44; H, 5.42; N, 14.43; S, 11.07.

EXAMPLE 12

2-[[(5-Methoxy-1H-benzimidazol-2-yl)sulfinyl]methyl]benzenamine

The title compound was prepared by the method of Example 3 using 1.20 g of the title product of Example 11 instead of the title product of Example 2. Trituration with diethylether gave 1.04 g of the title compound: m.p. 147–148° C. Analysis. Calc'd. for $C_{15}H_{15}N_3O_2S$: C, 59.78; H, 5.02; N,13.94; S, 10.64. Found: C, 59.30; H, 4.95; N, 13.55; S, 10.73.

EXAMPLE 13

Methyl 2-[[(2-aminophenyl)methyl]thio]-5-methoxy-1H-benzimidazole-6-carboxylate, dihydrochloride To a mixture of 29.0 g (0.16 mole) of methyl-4-amino-2-methoxybenzoate, 0.5 g of 4-dimethylaminopyridine, and 16.0 gm (0.16 mole) of triethylamine in 500 ml of dichloromethane was added in batches 22 ml (ca. 0.23 mole) of acetic acid. After two hours the reaction mixture was neutralized with sodium bicarbonate (in solution and as a solid). The organic phase was washed successively with aqueous sodium bicarbonate. The organic phase was washed successively with aqueous sodium bicarbonate and brine, dried over magnesium sulfate, filtered, and concentrated in vacuo. Recrystallization from toluene gave 30 g of methyl-4-acetamido-2-methoxybenzoate. To 100 ml of fuming nitric acid, stirred at −40° C., was slowly added 22.3 g (0.10 mole)of the acetylated intermediate. After about twenty minutes the mixture was warmed to 0° C. and stirred for another twenty minutes. The mixture was poured onto one liter of ice and the resultant precipitate was collected. Recrystallization from toluene/ethanol gave 14.2 g of the nitrated and deacetylated compound, methyl-4-amino-2-methoxy-5-nitrobenzoate. (Under similar conditions in which the acetyl group is not removed, saponification with methanolic sodium hydroxide gives the same product.) Hydrogenation of the nitro intermediate in tetrahydrofuran using Raney nickel as catalyst gave methyl-4,5-diamino-2-methoxybenzoate. A mixture of 4.83 g (24.6 mmole) of the diamine and 7.08 g (49.2 mmole) of potassium ethylxanthate was heated at reflux under argon in 40 ml of water. The resultant product mixture was chromatographed on silica gel to give 1.5 g of methyl-2-mercapto-5-methoxy-1H-benzimidazole-6-carboxylate. (Analysis. Calc'd. for $C_{10}H_{10}N_2O_3S$: C, 50.41; H, 4.23; N, 11.76; S, 13.46. Found: C, 50.30; H, 4.19; N, 11.71; S, 13.12.) The title compound was then prepared by the method of Example 1 using 1.19 g (5.0 mmole) of methyl-2-mercapto-5-methoxy-1H-benzimidazole-6-carboxylate instead of 2-mercaptobenzimidazole and 0.97 g (5.5 mmole) of 2-(chloromethyl)aniline hydrochloride instead of 2-(chloromethyl)-N,N-dimethylaniline. Analysis. Calc'd. for $C_{17}H_{17}N_3O_3S*2HCl$: C, 49.05; H, 4.60; N, 10.09; S, 7.70; Cl, 17.03. Found: C, 49.37; H, 4.77; N, 9.72; S, 7.43; Cl, 16.77.

EXAMPLE 14

Methyl 2-[[(2-aminophenyl)methyl]sulfinyl]-5-methoxy-1H-benzimidazole-6-carboxylate The title compound is prepared by the method of Example 3 using the title product of Example 11 instead of the title product of Example 2.

EXAMPLE 15

2-[(1H-Benzimidazol-2-ylthio)methyl]-4-chlorobenzenamine

The title compound was prepared by the method of Example 1 using 6.0 g of 2-(bromomethyl)-4-chloroaniline hydrobromide instead of 2-(chloromethyl)-N,N-dimethylaniline and isopropyl alcohol instead of ethanol. Concentration to dryness, chromatography on silica gel, and crystallization from methanol to which was added water, gave 343 mg of the title compound: m.p. 114–118° C. Analysis. Calc'd. for $C_{14}H_{12}N_3ClS$: C, 58.02; H, 4.17; N, 14.50; Cl, 12.23; S, 11.06. Found: C, 58.16; H, 4.24; N, 14.44; Cl, 12.35; S, 11.35.

EXAMPLE 16

2-[(1H-Benzimidazol-2-ylsulfinyl)methyl]-4-chlorobenzenamine

The title compound was prepared by the method of Example 3 using 1.36 g of the title product of Example 15 instead of the title product of Example 2 and dichloromethane instead of chloroform. After the initial trituration, purification was effected using chromatography on silica gel. Trituration with methanol/dichloromethane gave 316 mg of the title compound: m.p. 210–211° C. Analysis. Calc'd. for $C_{14}H_{13}N_3OClS$: C, 54.99; H, 3.96; N, 13.74; Cl, 11.59; S, 10.48. Found: C, 54.87; H, 3.91; N, 13.55; Cl, 12.26; S, 10.61.

EXAMPLE 17

2-[(1H-Benzimidazol-2-ylthio)methyl]-5-chlorobenzenamine

The title compound was prepared by the method of Example 1 using 5.40 g of 2-(bromomethyl)-5-chloroaniline hydrobromide instead of 2-(chloromethyl)-N,N-dimethylaniline in 100 ml of isopropyl alcohol. Chromatography on silica gel and recrystallization from acetonitrile gave 160 mg of the title compound: m.p. 158–160.5° C. Analysis. Calc'd. for $C_{14}H_{12}N_3ClS$: C, 58.03; H, 4.17; N, 12.23; S, 11.06. Found: C, 57.95; H, 4.22; N, 14.41; Cl, 12.54; S, 10.96.

EXAMPLE 18

2-[(1H-Benzimidazol-2-ylsulfinyl)methyl]-5-chlorobenzenamine

The title compound was prepared by the method of Example 3 using 1.13 g of the title product of Example 17 instead of the title product of Example 2. Trituration with chloroform gave 1.04 g of the title compound: m.p. 173.5–175.5° C. Analysis. Calc'd. for $C_{14}H_{12}N_3ClOS$: C, 54.99; H, 3.96; N, 13.74; Cl, 11.59; S, 10.48. Found: C, 54.37; H, 3.99; N, 13.43; Cl, 11.52; S, 10.21.

EXAMPLE 19

2-[(1H-Benzimidazol-2-ylthio)methyl]-4-methoxybenzenamine dihydrochloride

The title compound was prepared by the method of Example 1 using 2.85 g of 2-(chloromethyl)-4-methoxyaniline hydrochloride instead of 2-(chloromethyl)-N,N-dimethylaniline. The precipitate was not neutralized with base but was instead washed sequentially with ethanol and diethyl ether, giving 2.56 g of the title compound as the dihydrochloride, m.p. 206–208° C. Analysis. Calc'd. for $C_{15}H_{15}N_3OS*2HCl$: C, 50.29; H, 4.78; N, 11.73; S, 8.95; Cl, 19.79. Found: C, 49.95; H, 4.57; N, 11.55; S, 9.07; Cl, 19.09.

EXAMPLE 20

2-[(1H-Benzimidazol-2-ylsulfinyl)methyl]-4-methoxybenzenamine

The title compound was prepared by the method of Example 3 using 2.20 g of the free base of the title product of Example 19 instead of the title product of Example 2. Trituration with diethyl ether gave 900 mg of the title compound: m.p. 152–153° C. Calc'd. for $C_{15}H_{15}N_3O_2S$: C, 59.78; H, 5.02; N, 13.94; S, 10.64. Found: C, 59.01; H, 4.97; N, 13.65; S, 10.65.

EXAMPLE 21

2-[(1H-Benzimidazol-2-ylthio)methyl]-6-methoxybenzenamine hemihydrate

The title compound was prepared by the method of Example 1 using 4.16 g of 2-(chloromethyl)-6-methoxyaniline hydrochloride instead of 2-(chloromethyl)-N,N-dimethylaniline. Trituration with diethyl ether gave 2.40 g of the title compound. Analysis. Calc'd. for $C_{15}H_{15}N_3OS*½ H_2O$: C, 61.20; H, 5.48; N, 14.27; S, 10.89. Found: C, 61.79; H, 5.10; N, 14.72; S, 11.10.

EXAMPLE 22

2-((1H-Benzimidazol-2-ylsulfinyl)methyl]-6-methoxybenzenamine hemihydrate

The title compound was prepared by the method of Example 3 using 1.50 g of the title product of Example 21 instead of the title product of Example 2. The reaction mixture was concentrated in vacuo and triturated with diethyl ether. After filtration, the filtrate deposited 202 mg of the title compound: m.p. 141–143° C. Analysis. Calc'd. for $C_{15}H_{15}N_3O_2S*½ H_2O$: C, 58.05; H, 5.20; N, 13.54; S, 10.33. Found: C, 57.65; H, 5.17; N, 13.19; S, 10.50.

EXAMPLE 23

2-[(1H-Benzimidazol-2-ylthio)methyl]-3-methylbenzenamine

The title compound was prepared by the method of Example 1 using 3.55 g of 2-(chloromethyl)-3-methylaniline hydrochloride instead of 2-(chloromethyl)-N,N- dimethylaniline. Trituration with diethyl ether gave 2.31 g of the title compound. Analysis. Calc'd. for $C_{15}H_{15}N_3S$: C, 66.89; H, 5.61; N, 15.60; S, 11.90. Found: C, 66.61; H, 5.53; N, 15.52; S, 11.80.

EXAMPLE 24

2-[(1H-Benzimidazol-2-ylsulfinyl)methyl]-3-methylbenzenamine ¼ hydrate

The title compound was prepared by the method of Example 3 using 1.07 g of the title product of Example 23 instead of the title product of Example 2. Trituration with dichloromethane gave 327 mg of the title compound: m.p. 152–153° C. Analysis. Calc'd. for $C_{15}H_{15}N_3OS*¼ H_2O$: C, 62.21; H, 5.31; N, 14.51; S, 11.07. Found: C, 62.28; H, 5.05; N, 14.46; S, 11.22.

EXAMPLE 25

2-[(1H-Benzimidazol-2-ylthio)methyl]-4-methylbenzenamine

The title compound was prepared by the method of Example 1 using 2-(chloromethyl)-4-methylaniline hydrochloride instead of 2-(chloromethyl)-N,N-dimethylaniline. Chromatography on silica gel gave 650 mg of the title compound. Analysis. Calc'd. for $C_{15}H_{15}N_3S$: C, 66.89; H, 5.61; N, 15.60; S, 11.90. Found: C, 66.70; H, 5.65; N, 15.50; S, 11.85.

EXAMPLE 26

2-[(1H-Benzimidazol-2-ylsulfinyl)methyl]-4-methylbenzenamine

The title compound was prepared by the method of Example 3 using 2.63 g of the title product of Example 25 instead of the title product of Example 2 and using 1,2-dichloroethane as solvent instead of chloroform. Trituration with diethyl ether gave 3.0 g of the title compound. Analysis. Calc'd. for $C_{15}H_{15}N_3OS$: C, 63.14; H, 5.30; N, 14.73; S, 11.23. Found: C, 61.44; H, 4.98; N, 14.35; S, 11.10.

EXAMPLE 27

2-[(1H-Benzimidazol-2-ylthio)methyl]-6-methylbenzenamine

The title compound was prepared by the method of Example 1 using 5.00 g of 2-(chloromethyl)-6-methylaniline hydrochloride instead of 2-(chloromethyl)-N,N-dimethylaniline. Trituration with hexane gave 3.33 g of the title compound: m.p. 130–134° C. Analysis. Calc'd. for $C_{15}H_{15}N_3S$: C, 66.89; H, 5.61; N, 15.60; S, 11.90. Found: C, 66.85; H, 5.61; N, 15.20; S, 11.50.

EXAMPLE 28

2-[(1H-Benzimidazol-2-ylsulfinyl)methyl]-6-methylbenzenamine

The title compound was prepared by the method of Example 3 using 1.68 g of the title product of Example 27 instead of the title product of Example 2. Trituration with acetonitrile gave 948 mg of the title compound: m.p. 156–157° C. Analysis. Calc'd. for $C_{15}H_{15}N_3OS$: C, 63.14; H, 5.30; N, 14.73; S, 11.23. Found: C, 62.91; H, 5.13; N, 14.33; S, 11.08.

EXAMPLE 29

2-[(1H-Benzimidazol-2-ylthio)methyl]-4,6-dimethylbenzenamine

The title compound was prepared by the method of Example 1 using 1.68 g of 2-(chloromethyl)-4,6-dimethylaniline hydrochloride instead of 2-(chloromethyl)-N,N-dimethylaniline. Crystallization from diethyl ether gave 788 mg of the title compound: m.p. 139–141° C. Analysis. Calc'd. for $C_{16}H_{17}N_3S$: C, 67.81; H, 6.05; N, 14.83; S, 11.31. Found: C, 67.30; H, 5.93; N, 14.66; S, 11.29.

EXAMPLE 30

2-[(1H-Benzimidazol-2-ylsulfinyl)methyl]-4,6-dimethylbenzenamine hemihydrate

The title compound was prepared by the method of Example 3 using 950 mg of the title product of Example 29 instead of the title product of Example 2. Trituration with diethylether gave 434 mg of the title compound. Analysis. Calc'd. for $C_{16}H_{17}N_3OS*½ H_2O$: C, 62.23; H, 5.88; N, 13.63; S, 10.40. Found: C, 62.39; H, 5.72; N, 13.50; S, 10.65.

EXAMPLE 31

2-[(1H-Benzimidazol-2-ylthio)methyl]-N-methylbenzenamine

The title compound was prepared by the method of Example 1 using 28.8 g of 2-(chloromethyl)-N-methylaniline hydrochloride instead of 2-(chloromethyl)-N,N-dimethylaniline. Trituration with diethyl ether gave 22.5 g of the title compound: m.p. 109–112° C. Analysis. Calc'd. for $C_{15}H_{15}N_3S$: C, 66.89; H, 5.61; N, 15.60; S, 11.90. Found: C, 66.76; H, 5.72; N, 15.47; S, 11.98.

EXAMPLE 32

2-[(1H-Benzimidazol-2-ylsulfinyl)methyl]-N-methylbenzenamine monohydrate

The title compound was prepared by the method of Example 3 using 10.0 g of the title product of Example 31 instead of the title product of Example 2. Trituration with diethylether, filtration, and concentration of the filtrate gave 4.33 g of the title compound: m.p. 117–120° C. Analysis. Calc'd. for $C_{15}H_{15}N_3OS*H_2O$: C, 59.39; H, 5.65; N, 13.85; S, 10.57. Found: C, 59.10; H, 5.57; N, 13.92; S, 10.47.

EXAMPLE 33

2-[[(5-Methoxy-1H-benzimidazol-2-yl)thio]methyl]-4-methylbenzenamine

The title compound (1.95 g) was prepared by the method of Example 1 using 2.81 g of 2-mercapto-5-methoxybenzimidazole instead of 2-mercaptobenzimidazole and 3.00 g of 2-(chloromethyl)-4-methylaniline hydrochloride instead of 2-(chloromethyl)-N,N-dimethylaniline. Analysis. Calc'd. for $C_{16}H_{17}N_3OS$: C, 64.19; H, 5.72; N, 14.04; S, 10.71. Found: C, 63.71; H, 5.80; N, 13.86; S, 10.60.

EXAMPLE 34

2-[[(5-Methoxy-1H-benzimidazol-2-yl)sulfinyl]methyl]-4-methylbenzenamine

The title compound was prepared by the method of Example 3 using 1.50 g of the title product of Example 33 instead of the title product of Example 2. Concentration to dryness and trituration with diethyl ether gave 1.10 g of the title compound: m.p. 148–149° C. Analysis. Calc'd. for $C_{16}H_{17}N_3O_2S$: C, 60.93; H, 5.43; N, 13.32; S, 10.17. Found: C, 60.67; H, 5.38; N. 13.20; S, 9.95.

EXAMPLE 35

2-[[(5-methoxy-1H-benzimidazol-2-yl)thio]methyl]-6-methylbenzenamine

The title compound was prepared by the method of Example 1 using 3.75 g of 2-mercapto-5-methoxybenzimidazole instead of 2-mercaptobenzimidazole and 4.00 g of 2-(chloromethyl)-6-methylaniline hydrochloride instead of 2-(chloromethyl)-N,N-dimethylaniline. Trituration with hexane gave 3.02 g of the title compound: m.p. 132–134° C. Analysis. Calc'd. for $C_{16}H_{17}N_3OS$: C, 64.19; H, 5.72; N, 14.04; S, 10.71. Found: C, 64.21; H, 5.77; N, 14.00; S, 10.38.

EXAMPLE 36

2-[[(5-Methoxy-1H-benzimidazol-2-yl)sulfinyl]methyl]-6-methylbenzenamine

The title compound was prepared by the method of Example 3 using 2.00 g of the title product of Example 35 instead of the title product of Example 2. Trituration with diethylether gave 1.58 g of the title compound: m.p. 142–144° C. Analysis. Calc'd. for $C_{16}H_{17}N_3O_2S$: C, 60.93; H, 5.43; N, 13.32; S, 10.17. Found: C, 60.60; H, 5.42; N, 12.83; S, 9.86.

EXAMPLE 37

2-[(1H-Benzimidazol-2-ylsulfinyl)methyl]-4-ethylbenzenamine

The title compound, m.p. 155–156° C., was prepared by the methods of Examples 1 and 3 using 2-(chloromethyl)-4-ethylaniline hydrochloride instead of 2-(chloromethyl)-N,N-dimethylaniline. Analysis. Calc'd. for $C_{16}H_{17}N_3OS$: C, 64.19; H, 5.72; N, 14.04; S, 10.71. Found: C, 63.86; H, 5.67; N, 14.01; S, 10.68.

EXAMPLE 38

2-[(1H-Benzimidazol-2-ylsulfinyl)methyl]-6-ethylbenzenamine

The title compound was prepared by the methods of Examples 1 and 3 using 2-(chloromethyl)-6-ethylaniline hydrochloride instead of 2-(chloromethyl)-N,N-dimethylaniline. Analysis. Calc'd. for $C_{16}H_{17}N_3OS$: C, 64.19; H, 5.73; N, 14.04; S, 10.71. Found: C, 63.88; H, 5.55; N, 13.87, S, 10.57.

EXAMPLE 39

2-[(1H-Benzimidazol-2-ylsulfinyl)methyl]-4-methoxy-3,5-dimethylbenzenamine

A mixture of 10 g (66.2 mmole) of 4-methoxy-3,5-dimethylaniline and 10 g (67.6 mmole) of phthalic anhydride was heated at 170° C. for 30 minutes, then allowed to cool overnight to room temperature. Recrystallization from aqueous ethanol gave 16.4 g (58.4 mmole) of the phthalimide derivative. Paraformaldehyde (3 g, 100 mmole) was dissolved in 100 ml of concentrated sulfuric acid and the mixture was cooled to 0° C. Hydrogen chloride gas was introduced over a five-minute period, after which the phthalimide derivative was added in small batches. After additional hydrogen chloride gas was introduced for five minutes, the mixture was stirred at 0° C. for 45 minutes. The mixture was poured over ice, filtered, and washed with water, giving 5.34 g of the phthalimide derivative (m.p. 267–271° C.) of 2-hydroxymethyl-4-methoxy-3,5-dimethylaniline. Using the general method of Example 2 with this phthalimide derivative instead of 2-aminobenzyl alcohol and concentrated hydrochloric acid instead of sulfuric acid produced the phthalimide derivative of 2-[(1H-benzimidazol-2-ylthio)methyl]-4-methoxy-3,5-dimethylbenzenamine. Trituration with diethyl ether gave 3.4 g of the analytically pure compound, m.p. 240–244° C. [Analysis. Calc'd. for $C_{25}H_{21}N_3O_3S$: C, 67.70; H, 4.77; N, 9.47; S, 7.23. Found: C, 67.57; H, 4.84; N, 9.53; S, 7.31.] Using the method of Example 3 with 3.0 g (6.8 mmole) of this phthalimide derivative instead of the title product of Example 2 produced the corresponding sulfoxide. Trituration with diethyl ether gave 2.81 g of the analytically pure sulfoxide as the ¼ hydrate: m.p. 198.5–201° C. [Analysis. Calc'd. for $C_{25}H_{21}N_3O_4S*¼ H_2O$: C, 64.71; H, 4.67; N, 9.06; S, 6.91. Found: C, 64.82; H, 4.63; N, 9.07; S, 6.96.] The sulfoxide (1.0 g, 2.2 mmole) was dissolved in 50 ml of methanol by warming to 50–60° C. and then allowed to cool to room temperature. Hydrazine hydrate (1 ml, ca. 20 mmole) was added and the mixture was stirred for about 5 hours. The resultant suspension was concentrated in vacuo, suspended in water, and treated with about 50 drops of aqueous ammonium hydroxide. The precipitate was collected and washed with dilute ammonium hydroxide to give 0.47 g of the title compound: m.p. 150–155° C. Analysis. Calc'd. for $C_{17}H_{19}N_3O_2S$: C, 61.98; H, 5.81; N, 12.76; S, 9.73. Found: C, 61.66; H, 5.85; N, 12.61; S, 9.34.

EXAMPLE 40

2-[[(5-Methyl-1H-benzimidazol-2-yl)thio]methyl]benzenamine

The title compound was prepared by the method of Example 1 using 2.50 g of 2-mercapto-5-methylbenzimidazole instead of 2-mercaptobenzimidazole and 2.71 g of 2-(chloromethyl)aniline hydrochloride instead of 2-(chloromethyl)-N,N-dimethylaniline in isopropyl alcohol. The basic extraction used 5% sodium hydroxide instead of sodium carbonate. Washing the solid residue from the dichloromethane extract with additional dichloromethane gave 1.65 g of the title compound. Analysis. Calc'd. for $C_{15}H_{15}N_3S$: C, 66.89; H, 5.61; N, 15.60; S, 11.90. Found: C, 65.78; H, 5.48; N, 15.54; S, 11.94.

EXAMPLE 41

2-[[(5-Methyl-1H-benzimidazol-2-yl)sulfinyl]-methyl]benzenamine

The title compound was prepared by the method of Example 3 using 1.46 g of the title product of Example 40 instead of the title product of Example 2. Trituration with 2.5% aqueous potassium carbonate and with water gave 1.02 g of the title compound: m.p. 170–171° C. Analysis. Calc'd. for $C_{15}H_{15}N_3OS$: C, 63.14; H, 5.30; N, 14.73; S, 11.23. Found: C, 62.76, H, 5.30; N, 14.86; S, 11.25.

EXAMPLE 42

2-[[(5-Chloro-1H-benzimidazol-2-yl)thio]-methyl)benzenamine

The title compound was prepared by the method of Example 1 using 2.50 g of 2-mercapto-5- chlorobenzimidazole instead of 2-mercaptobenzimidazole and 2.42 g of 2-(chloromethyl)aniline hydrochloride instead of 2-(chloromethyl)-N,N-dimethylaniline. The basic extraction used 5% sodium hydroxide instead of sodium carbonate. Washing the solid residue from the dichloromethane extract with additional dichloromethane gave 2.47 g of the title compound. Analysis. Calc'd. for $C_{14}H_{12}N_3ClS$: C, 58.03; H, 4.17; N, 14.10; S, 11.06; Cl, 12.23. Found: C, 57.33; H, 4.06; N, 14.27; S, 10.99; Cl, 12.74.

EXAMPLE 43

2-[[(5-Chloro-1H-benzimidazol-2-yl)sulfinyl]-methyl]benzenamine

The title compound (1.41 g), m.p. 165–166° C., was prepared by the method of Example 3 using 2.00 g of the title product of Example 42 instead of the title product of Example 2. Analysis. Calc'd. for $C_{14}H_{12}N_3ClOS$: C, 54,99; H, 3.96; N, 13.74; S, 10.48; Cl, 11.59. Found: C, 54.40; H, 3.86; N, 13.47; S, 10.83; Cl, 12.05.

EXAMPLE 44

2-[[(5-Ethoxy-1H-benzimidazol-2-yl)thio)-methyl]benzenamine monohydrate

The title compound was prepared by the method of Example 1 using 3.00 g of 2-mercapto-5-ethoxybenzimidazole instead of 2-mercaptobenzimidazole and 2.76 g of 2-(chloromethyl)aniline hydrochloride instead of 2-(chloromethyl)-N,N-dimethylaniline in 250 ml of isopropyl alcohol. The basic extraction used 5% sodium hydroxide instead of sodium carbonate. Crystallization during concentration of the dichloromethane extract gave 2.60 g of the title compound as the monohydrate: m.p. 87–89° C. Analysis. Calc'd. for $C_{16}H_{17}N_3OS*H_2O$: C, 63.76; H, 5.68; N, 13.94; S, 10.64. Found: C, 63,65; H, 5.74; N, 13.89; S, 10.89.

EXAMPLE 45

2-[[(5-Ethoxy-1H-benzimidazol-2-yl)sulfinyl]-methyl]benzenamine

The title compound was prepared by the method of Example 3 using 2.30 g of the title product of Example 44 instead of the title product of Example 2. The reaction mixture was washed with 10% aqueous potassium carbonate, dried over sodium sulfate, filtered, and concentrated in vacuo to dryness. Trituration with diethyl ether gave 1.95 g of the title compound: m.p. 154–155° C. Analysis. Calc'd. for $C_{16}H_{17}N_3O_2S$: C, 60.93; H, 5.43; N, 13.32; S, 10.17. Found: C, 60.59; H, 5.36; N, 13.23; S, 10.27.

EXAMPLE 46

2-[[[(5-(Trifluoromethyl)-1H-benzimidazol-2-yl]thio]methyl]benzenamine

The title compound was prepared by the method of Example 1 using 4.36 g of 2-mercapto-5-(trifluoromethyl)benzimidazole instead of 2-mercaptobenzimidazole and 3.56 g of 2-(chloromethyl)aniline hydrochloride instead of 2-(chloromethyl)-N,N-dimethylaniline in isopropyl alcohol. The basic extraction used 5% sodium hydroxide instead of sodium carbonate. Washing the solid residue from the dichloromethane extract with additional dichloromethane gave 2.40 g of the title compound: m.p. ca. 155° C. Analysis. Calc'd. for $C_{15}H_{12}N_3F_3S$: C, 55.72; H, 3.74; N, 13.00; S, 9.92; F, 17.63. Found: C, 55.55; H, 3.68; N, 13.10; S, 10.12; F, 17.38.

EXAMPLE 47

2-[[[(5-(Trifluoromethyl)-1H-benzimidazol-2-yl]sulfinyl]methyl]benzenamine

The title compound was prepared by the method of Example 3 using 2.00 g of the title product of Example 46 instead of the title product of Example 2. The reaction mixture, which contained no precipitate, was concentrated in vacuo. Crystallization during the concentration gave 568 mg (in three crops) of the title compound: m.p. 152–152.5° C. Analysis. Calc'd. for $C_{15}H_{12}N_3F_3OS$: C, 53.09; H, 3.56; N, 12.38; S, 9.45; F, 16.80. Found: C, 53.23; H, 3.61; N, 12.48; S, 9.64; F, 16.89.

EXAMPLE 48

2-[(1H-Benzimidazol-2-ylthio)methyl]-4-(trifluoromethyl)benzenamine

To a cold (ca. 0° C.) solution of 10.0 g (62 mmole) of 4-(trifluoromethyl)aniline and 6.6 g (65 mmole) of triethylamine in 100 ml of dichloromethane was added dropwise 7.9 g (65 mmole) of pivaloyl chloride. After stirring overnight, the mixture was poured into water. The aqueous layer was washed with additional dichloromethane and the organic layers were combined. The organic extracts were washed with three portions of water, dried over magnesium sulfate, filtered, and concentrated in vacuo to dryness. The residue was recrystallized from hexane, giving 14.2 g of the N-acylated aniline derivative. A mixture of 17.2 g of the N-acylated aniline derivative and 24 ml or redistilled tetramethylethylenediamine was stirred in diethyl ether cooled to about −5° C. in an ice-methanol bath. As the temperature was maintained at or below 5° C., 100 ml of 1.55 M butyllithium in hexane was added to form the aromatic carbanion. After being allowed to warm to room temperature, the mixture was stirred for about four hours. Formulation of the carbanion was effected by adding 15 ml of dimethylformamide dropwise at −5° C. The reaction mixture was partitioned between water and diethylether. The water layer was separated and washed with additional diethyl ether. The ether layers were combined, dried over magnesium sulfate, filtered, and concentrated in vacuo to an oil. Column chromatography on silica gel gave 12.9 g of N-acylated 2-amino-5-trifluoromethyl)benzaldehyde as a solid. The benzaldehyde derivative (6.3 g) was converted to the corresponding benzyl alcohol derivative by reaction in 60 ml of ethanol with 1.05 g of sodium borohydride, added as a solution in 10 ml of aqueous 0.6 N sodium hydroxide. The borohydride solution was acidified with dilute hydrochloric and concentrated in vacuo to dryness. The residual solid was washed thoroughly with water and air-dried, giving 6.2 g of the benzyl alcohol derivative. A solution of 3 g of the benzyl alcohol derivative in 30 ml of dioxane was heated at about 80° C. for about four hours with 40 ml of concentration aqueous hydrochloric acid. Upon cooling, the reaction mixture was concentrated to dryness under a stream of nitrogen. The residue was washed thoroughly with diethyl ether, giving 2-(chloromethyl)-4-(trifluoromethyl)aniline hydrochloride. Using-the general method of Example 1 with 1.56 g of 2-(chloromethyl)-4-(trifluoromethyl) hydrochloride instead of 2-(chloromethyl)-N,N-dimethylaniline produced the title compound. The reaction mixture, which contained no precipitate, was concentrated in vacuo to dryness. The residue was partitioned between dichloromethane and 5% aqueous sodium hydroxide instead of sodium carbonate. The dichloromethane extract was dried over sodium sulfate, filtered, and concentrated in vacuo to a gum. Recrystallization from dichloromethane gave 290 mg of the title compound: m.p. 130–137° C. Analysis. Calc'd. for $C_{15}H_{12}N_3F_3S$: C, 55.72; H, 3.74; N, 13.00; S, 9.92; F, 17.63. Found: C, 55.62; H, 3.59; N, 13.02; S, 10.25; F, 17.27.

EXAMPLE 49

2-[(1H-Benzimidazol-2-ylsulfinyl)methyl]-4-(trifluoromethyl)benzenamine

The title compound was prepared by the method of Example 3 using 530 mg of the title product of Example 48 instead of the title product of Example 2. Washing the precipitate from the reaction mixture with chloroform gave 465 mg of the title compound: m.p. 185–187° C. Analysis. Calc'd. for $C_{15}H_{12}N_3F_3OS$: C, 53,09; H, 3.56; N, 12.38; S, 9.45; F, 16.80. Found: C, 52.39; H, 3.41; N, 12.17; S, 9.66; F, 16.52.

EXAMPLE 50

2-[(1H-Benzimidazol-2-ylthio)methyl]-4-butylbenzenamine

The title compound was prepared by the method of Example 1 using 1.08 g of 4-butyl-2-(chloromethyl)aniline hydrochloride instead of 2-(chloromethyl)-N,N-dimethylaniline. The reaction mixture was concentrated in vacuo to dryness. The residue was partitioned between dichloromethane and 5% aqueous sodium hydroxide instead of sodium carbonate. The dichloromethane extract was dried over sodium sulfate, filtered, and concentrated in vacuo to an oil. Trituration with hexane gave a solid that was recrystallized from diethyl ether-hexane to give the title compound: m.p. 108–109.5° C. The compound was used in subsequent reactions without further purification.

EXAMPLE 51

2-[(1H-Benzimidazol-2-ylsulfinyl)methyl]-4-butylbenzenamine

The title compound was prepared by the method of Example 3 using 487 mg of the title product of Example 50 instead of the title product of Example 2. The precipitate from the reaction mixture was collected, giving 351 mg of the title compound: m.p. 146–148° C. Analysis. Calc'd. for $C_{18}H_{21}N_3OS$: C, 66.03; H, 6.46; N, 12.83; S, 9.79. Found: C, 65.69; H, 6.50; N, 12.85; S. 9.79.

EXAMPLE 52

2-[(1H-Benzimidazol-2-ylthio)methyl]-5,6-dimethylbenzenamine

The title compound was prepared by the method of Example 1 using 3.00 g of 2-(chloromethyl)-5,6-dimethylaniline hydrochloride instead of 2-(chloromethyl)-N,N-dimethylaniline in isopropyl alcohol. The basic extraction used 5% sodium hydroxide instead of sodium carbonate. The solid residue from the dichloromethane extract gave, without further purification, 3.09 g of the title compound. Analysis. Calc'd. for $C_{16}H_{17}N_3S$: C, 67.81; H, 6.05; N, 14.83; S, 11.31. Found: C, 67.46; H, 6.36; N, 14.40; S, 10.90.

EXAMPLE 53

2-[(1H-Benzimidazol-2-ylsulfinyl)methyl]-5,6-dimethylbenzenamine ¼ hydrate

The title compound was prepared by the method of Example 3 using 2.97 g of the title product of Example 52 instead of the title product of Example 2. The reaction mixture was concentrated in vacuo to dryness. The residue was washed with diethyl ether and redissolved in 400 ml of 15% (by volume) of methanol in dichloromethane. The organic solution was washed with 5% aqueous potassium carbonate, dried over sodium sulfate, filtered, and concentrated in vacuo. Crystallization during the concentration gave 1.36 g of the title compound: m.p. 160° C. (decomp). Analysis. Calc'd. for $C_{16}H_{17}N_3OS*¼ H2O$: C, 63.24; H, 5.80; N, 13.85; S, 10.55. Found: C, 62.72; H, 5.65; N, 13.58; S, 10.50

EXAMPLE 54

2-[(1H-Benzimidazol-2-ylthio)methyl]-3,6-dimethylbenzenamine

The title compound was prepared by the method of Example 1 using 2.00 g of 2-(chloromethyl)-3,6-dimethylaniline hydrochloride instead of 2-(chloromethyl)-N,N-dimethylaniline in isopropyl alcohol. The basic extraction used 10% sodium hydroxide instead of sodium carbonate. Crystallization during concentration of the dichloromethane extract gave 1.60 g of the title compound. analysis. Calc'd. for $C_{16}H_{17}N_3S$: C, 67.81; H, 6.05; N, 14.83; S, 11.31. Found: C, 67.20; H, 6.03; N, 14.82; S, 11.29.

EXAMPLE 55

2-[(1H-Benzimidazol-2-ylsulfinyl)methyl]-3,6-dimethylbenzenamine monohydrate

The title compound was prepared by the method of Example 3 using the title product of Example 54 instead of the title product of Example 2. The reaction mixture was concentrated in vacuo to dryness. The residue was washed with diethyl ether and redissolved in 400 ml of 10% (by volume) of methanol in dichloromethane. The organic solution was washed with 10% aqueous potassium carbonate, dried over sodium sulfate, filtered, and concentrated in vacuo. The resultant residue was washed with diethylether to give 621 mg of the title compound: m.p. 144–145° C. Analysis. Calc'd. for $C_{16}H_{17}N_3OS*H_2O$: C, 60.55; H, 6.03; N, 13.24; S, 10.10. Found: C, 60.40; H, 5.69; N, 13.05; S, 9.98.

EXAMPLE 56

2-[(1H-Benzimidazol-2-ylthio)methyl]-4-chloro-6-methylbenzenamine

The title compound was prepared by the method of Example 1 using 4.3 g. of 2-(chloromethyl)-4-chloro-6-methylaniline hydrochloride instead of 2-(chloromethyl)-N,N-dimethylaniline in isopropyl alcohol. The basic extraction used 10% sodium hydroxide instead of sodium carbonate. The solid residue from the dichloromethane extract was redissolved in diethyl ether and again concentrated in vacuo to dryness to give, without further purification, the title compound. Analysis. Calc'd. for $C_{15}H_{14}N_3ClS$: C, 59.30; H, 4.65; N, 13.83; S, 11.67. Found: C, 58.98; H, 4.76; N, 13.47; S, 11.61.

EXAMPLE 57

2-[(1H-Benzimidazol-2-ylsulfinyl)methyl]-4-chloro-6-methylbenzenamine hemihydrate The title compound was prepared by the method of Example 3 using 3.12 g. of the title product of Example 56 instead of the title product of Example 2. The reaction mixture was concentrated in vacuo to dryness. The residue was dissolved in 400 ml of 5% (by volume) of methanol in chloroform. The organic solution was washed with 10% aqueous potassium carbonate, which was then backwashed with dichloromethane. The organic layers were combined, dried over sodium sulfate, filtered, and concentrated in vacuo. Washing the residue with diethyl ether gave 674 mg of the title compound: m.p. 168–169° C. Analysis. Calc'd. for $C_{15}H_{14}N_3ClOS*½ H_2O$: C, 54.79; H, 4.29; N 12.78; S, 9.75. Found: C, 54.59; H, 4.43; N, 12.64; S, 9.88.

EXAMPLE 58

2-[(1H-Benzimidazol-2-ylthio)methyl]-4-chloro-6-methoxy-3-methylbenzenamine

The title compound was prepared by the method of Example 1 using 2.50 g of 2-(chloromethyl)-4-chloro-6-methoxy-3-methylaniline hydrochloride instead of 2-(chloromethyl)-N,N-dimethylaniline in isopropyl alcohol. The precipitate from the reaction mixture was partitioned between dichloromethane and 5% aqueous sodium hydroxide instead of sodium carbonate. The dichloromethane extract was dried over sodium sulfate, filtered, and concentrated in vacuo to a solid. Trituration with hexane gave 2.23 g of the title compound: m.p. 146–148° C. (partial melting at ca. 100° C. with solidification). Analysis. Calc'd. for $C_{16}H_{16}N_3ClOS$: C, 57.57; H, 4.83; N, 12.59; S, 9.60; Cl, 10.62. Found: C, 57.49; H, 4.83; N. 12.40; S, 9.55; Cl, 10.80.

EXAMPLE 59

2-[(1H-Benzimidazol-2-ylsulfinyl)methyl]-4-chloro-6-methoxy-3-methylbenzenamine

The title compound was prepared by the method of Example 3 using 2.00 g of the title product of Example 58 instead of the title product of Example 2. The reaction mixture, after clarification by filtration, was washed with 10% aqueous potassium carbonate, dried over sodium sulfate, filtered, and concentrated in vacuo. Washing the residue with diethyl ether gave 1.19 g of the title compound: m.p. 163–164° C. Analysis. Calc'd. for $C_{16}H_{16}N_3ClO2S$: C, 54.93; H, 4.61; N, 12.01; S, 9.16; Cl, 10.13. Found: C, 54.68; H, 4.54; N, 11.56; S, 8.89; Cl, 10.29.

EXAMPLE 60

2-[[(5-Ethoxy-1H-benzimidazol-2-yl)thio]-methyl]-4-methylbenzenamine

The title compound was prepared by the method of Example 1 using 3.00 g of 2-mercapto-5-tethoxybenzimidazole instead of 2-mercaptobenzimidazole and 3.71 g of 2-(chloromethyl)-4-methylaniline hydrochloride instead of 2-(chloromethyl)-N,N-dimethylaniline in isopropyl alcohol. The basic extraction used 10% sodium hydroxide instead of sodium carbonate. Crystallization during concentration of the dichloromethane extract gave 2.13 g of the title compound, which was used in subsequent reactions without further purification.

EXAMPLE 61

2-[[(5-Ethoxy-1H-benzimidazol-2-yl)sulfinyl]-methyl]-4-methylbenzenamine

The title compound was prepared by the method of Example 3 using 1.90 g of the title product of Example 60 instead of the title product of Example 2. The reaction mixture, which contained no precipitate, was concentrated in vacuo to dryness. Trituration with diethyl ether gave 1.19 g of the title compound: m.p. 144–145° C. Analysis. Calc'd. for $C_{17}H_{19}N_3O_2S$: C, 61.98; H, 5.81; N, 12.76; S, 9.73. Found: C, 61.38; H, 5.80; N, 12.57; S, 9.85.

EXAMPLE 62

2-[[(5-Methyl-1H-benzimidazol-2-yl)thio]methyl]-5,6-dimethylbenzenamine

The title compound was prepared by the method of Example 1 using 207 mg of 2-mercapto-5-methylbenzimidazole instead of 2-mercaptobenzimidazole and 260 mg of 2-(chloromethyl)-5,6-dimethylaniline hydrochloride instead of 2-(chloromethyl)-N,N-dimethylaniline in isopropyl alcohol. The basic extraction used 10% sodium hydroxide instead of sodium carbonate. The dichloromethane extract was dried over sodium sulfate, filtered, and concentrated in vacuo to 274 mg of the title compound as a gum. The compound was used in subsequent reactions without further purification.

EXAMPLE 63

2-[[(5-Methyl-1H-benzimidazol-2-yl)sulfinyl]-methyl]-5,6-dimethylbenzenamine hemihydrate The title compound (45 mg), m.p. 141–143° C., was prepared by the method of Example 3 using 254 mg of the title product of Example 62 instead of the title product of Example 2. Analysis. Calc'd. for $C_{17}H_{19}N_3OS*H_2O$: C, 63.33; H, 5.94; N, 13.03; S, 9.94. Found: C, 63.74; H, 5.91; N, 12.54; S, 9.73.

EXAMPLE 64

2-[[[(5-(Trifluoromethyl)1-1H-benzimidazol-2-yl]thio]methyl]-3,6-dimethylbenzenamine The title compound was prepared by the method of Example 1 using 529 mg of 2-mercapto-5-(trifluoromethyl)benzimidazole instead of 2-mercaptobenzimidazole and 500 mg of 2-(chloromethyl)-3,6-dimethylaniline hydrochloride instead of 2-(chloromethyl)-N,N-dimethylaniline in isopropyl alcohol. The basic extraction used 10% sodium hydroxide instead of sodium carbonate. The dichloromethane extract was dried over sodium sulfate, filtered, and concentrated in vacuo to 590 mg of the title compound as a gum. The compound was used in subsequent reactions without further purification.

EXAMPLE 65

2-[[[(5-(Trifluoromethyl)1-1H-benzimidazol-2-yl]sulfinyl]-3,6-dimethylbenzenamine The title compound was prepared by the method of Example 3 using 578 mg of the title product of Example 64 instead of the title product of Example 2. The reaction mixture, which contained no precipitate, was washed with 5% aqueous potassium carbonate, dried over sodium sulfate, filtered, and concentrated in vacuo to a gum. Crystallization from acetonitrile gave 126 mg of the title compound. Analysis. Calc'd. for $C_{17}H_{16}N_3FOS$: C, 55.58; H, 4.39; N, 11.44; S, 8.73; F, 15.51. Found: C, 55.43; H, 4.32; N, 11.48; S, 8.92; F, 15.31.

EXAMPLE 66

2-[[(5-(Trifluoromethyl)1-1H-benzimidazol-2-yl]thio]methyl]-6-methoxybenzenamine The title compound was prepared by the method of Example 1 using 1.09 g of 2-mercapto-5-(trifluoromethyl)benzimidazole instead of 2-mercaptobenzimidazole and 1.04 g of 2-(chloromethyl)-6-methoxyaniline hydrochloride instead of 2-(chloromethyl)-N,N-dimethylaniline in isopropyl alcohol. The basic extraction used 10% sodium hydroxide instead of sodium carbonate. The dichloromethane extract was dried over sodium sulfate, filtered, and concentrated in vacuo to an oil. Trituration with 1:1 (by volume) diethyl ether-hexane gave 1.16 g of the title compound as a solid: m.p. ca. 130–148° C. The compound was used in subsequent reactions without further purification.

EXAMPLE 67

2-[[[(5-(Trifluoromethyl)1-1H-benzimidazol-2-yl]sulfinyl]methyl]-6-methoxybenzenamine The title product of Example 66 (945 mg, 2.68 mmole) was dissolved in about 1 liter of warmed chloroform, filtered, and cooled to about −5° C. A solution of 600 mg (ca. 2.95 mmole) of ca. 85% M-chloroperbenzoic acid in 20 ml of chloroform was added and the mixture stirred for about one hour. Fine granular potassium carbonate (5 g) was added and the mixture was stirred for 20 hours, after which the insolubles were removed by filtration. The filtrate was passed through a pad of granular potassium carbonate and concentrated in vacuo to a gum. The gum was triturated with diethyl ether. The ether supernatant was removed by decanting and allowed to stand, giving 219 mg of a solid. The remaining gum was again triturated with diethyl ether, giving 227 mg additional solid. The solids were combined and dissolved in chloroform containing a small amount of methanol. The solution was washed with 5% aqueous potassium carbonate, dried over sodium sulfate, filtered, and concentrated in vacuo to dryness. Chromatography on silica gel gave, after washing the residue with hexane, 60 mg of the title compound. Analysis. Calc'd. for $C_{16}H_{14}N_3F_3O_2S$: C, 52.03; H, 3.82; N, 11.38; S, 8.68; F, 15.43. Found: C, 52.01; H, 3.85; N, 11.24; S, 8.62; F, 15.05.

EXAMPLE 68

Methyl 2-amino-3-[(1H-benzimidazol-2-ylthio)methyl]benzoate

The title compound was prepared by the method of Example 1 using 1.27 g of methyl 2-amino-3-(chloromethyl)benzoate hydrochloride (prepared from methyl 2-amino-3-(methylsulfinylmethyl)benzoate as reported by J. P. Chupp et al., *J. Org. Chem.*, 49, 4711 (1984) instead of 2-(chloromethyl)-N,N-dimethylaniline in isopropyl alcohol. Recrystallization of the title compound from diethyl ether gave 1.72 g of the title compound in three crops. Analysis. Calc'd. for $C_{16}H_{15}N_3O_2S$: C, 61.32; H, 4.82; N,13.41; S, 10.23. Found: C, 60.73; H, 4.86; N, 12.87; S, 9.67.

EXAMPLE 69

Methyl 2-amino-3-[(1H-benzimidazol-2-ylsulfinyl)methyl]benzoate hydrate

The title compound was prepared by the method of Example 3 using 1.55 g of the title product of Example 68 instead of the title product of Example 2. The precipitate from the reaction mixture was collected and redissolved in 10% (by volume) of methanol in diethyl ether. The organic solution was washed with 5% aqueous potassium carbonate, dried over sodium sulfate, filtered, and concentrated in vacuo. The resultant residue was washed with diethyl ether to give 496 mg of the title compound. Analysis. Calc'd. for $C_{16}H_{15}N_3O_3S*H_2O$: C, 55.32; H,4.35; N, 12.10; S, 9.23. Found: C, 55.01; H, 4.78; N, 11.86; S, 9.04.

EXAMPLE 70

Ethyl 4-amino-3-[(1H-benzimidazol-2-ylthio)methyl]benzoate

Ethyl 4-amino-3-(chloromethyl)benzoate hydrochloride was prepared from 20.0 g of ethyl 4-aminobenzoate using the method reported by J. P. Chupp et al., *J. Org. Chem.*, 49, 4711 (1984). The title compound was then prepared by the method of Example 1 using 1.75 g of ethyl 4-amino-3-(chloromethyl)benzoate hydrochloride instead of 2-(chloromethyl)-N,N-dimethylaniline in isopropyl alcohol. The basic extraction used 10% sodium hydroxide instead of sodium carbonate. Washing to solid residue from the dichloromethane extract with diethyl ether gave 865 mg of the title compound: m.p. 174–176° C. Analysis. Calc'd. for $C_{17}H_{17}N_3O_2S$: C, 62.37; H, 5.23; N, 12.83; S, 9.79. Found: C, 61.52; H, 5.31; N, 12.54; S, 9.72.

EXAMPLE 71

Ethyl 4-amino-3-[(1H-benzimidazol-2-ylsulfinyl)methyl]benzoate hemihydrate

The title compound (528 mg), m.p. 192–194° C., was prepared by the method of Example 3 using 781 mg of the title product of Example 70 instead of the title product of Example 2. Analysis. Calc'd. for $C_{17}H_{17}N_3O_3S*½H_2O$: C, 57.93; H, 4.86; N, 11.92; S, 9.10. Found: C, 57.75; H, 4.73; N, 11.96; S, 9.36.

EXAMPLE 72

Ethyl 4-amino-3-[[(5-methoxy-1H-benzimidazol-2-yl)thio]methyl]benzoate

The title compound was prepared by the method of Example 1 using 1.30 g of 2-mercapto-5-methoxybenzimidazole instead of 2-mercaptobenzimidazole and 1.80 g of ethyl 4-amino-3-(chloromethyl)benzoate hydrochloride (prepared as for Example 70) instead of 2-(chloromethyl)-N,N-dimethylaniline in isopropyl alcohol. The basic extraction used 10% sodium hydroxide instead of sodium carbonate and 1,2-dichloroethane instead of dichloromethane. The 1,2-dichloroethane extract was dried over sodium sulfate, filtered, and concentrated in vacuo to a gum. Recrystallization from diethyl ether-hexane gave 650 mg of the title compound: m.p. 140–146° C. Analysis. Calc'd. for $C_{18}H_{19}N_3O_3S$: C, 60.49; H, 5.36; N, 11.76; S, 8.90. Found: C, 60.27; H, 5.44; N, 11.39; S, 8.70.

EXAMPLE 73

Ethyl 4-amino-3-[[(S-methoxy-1H-benzimidazol-2-yl)sulfinyl]methyl]benzoate

The title compound was prepared by the method of Example 3 using 557 mg of the title product of Example 72 instead of the title product of Example 2. The reaction mixture was passed three times through a column of potassium carbonate powder and concentrated in vacuo to dryness. Crystallization for acetonitrile gave 257 mg of the title compound. Analysis. Calc'd. for $C_{18}H_{19}N_3O_4S$: C, 57.90; H, 5.13; N, 11.25; S, 8.59. Found: C, 57.63; H, 5.15; N, 11.32; S, 8.65.

EXAMPLE 74

2-[[5,6-Dimethoxy-1H-benzimidazol-2-yl)thio]methyl]benzenamine

The title compound was prepared by the method of Example 1 using 1.5 g of 2-mercapto-5,6-dimethoxybenzimidazole instead of 2-mercaptobenzimidazole and 1.3 g of 2-(chloromethyl)aniline hydrochloride instead of 2-(chloromethyl)-N,N-dimethylaniline in isopropyl alcohol. The precipitate from the reaction mixture was triturated with aqueous potassium carbonate, collected by filtration, and dried to give 1.9 g of the title compound, which was used in subsequent reactions without further purification.

EXAMPLE 75

2-[[5,6-Dimethoxy-1H-benzimidazol-2-yl)sulfinyl]methyl]-4-methylbenzenamine

The title compound was prepared by the method of Example 3 using 1.9 g of the title product of Example 74 instead of the title product of Example 2. The reaction mixture was concentrated in vacuo to dryness. The residue was triturated sequentially with diethyl ether, aqueous sodium carbonate, and diethyl ether. Column chromatography on silica gel gave 50 mg of the title compound. Analysis. Calc'd. for $C_{16}H_{17}N_3O_3S$: C, 57.99; H, 5.17; N, 12.68; S, 9.67. Found: C, 57.44; H, 5.19; N, 12.50; S, 9.80.

EXAMPLE 76

2-[(1H-Benzimidazol-2-ylsulfinyl)methyl]-4-fluorobenzenamine

A solution of 9.0 g (58 mmole) of 3-fluoro-6-nitrotoluene in 200 ml of ethyl acetate was hydrogenated at room temperature with 60 psi of hydrogen gas using 0.9 g of 5% palladium on charcoal as catalyst. The solution was filtered and concentrated to give 6.7 g of 4-fluoro-2-methylaniline as an oil. A mixture of 1.33 g of the oil and 1.57 of phthalic anhydride was heated at 160° C. for 30 minutes and cooled. The resultant solid was washed with methanol and air dried to give 1.96 of the phthalimide derivative of 4-fluoro-2-methylaniline, m.p. 189.5–190.5° C. [Analysis. Calc'd. for $C_{15}H_{10}NFO_2$: C,70.58; H, 3.95; N, 5.49; S, 7.44. Found: C, 70.68; H,3.95; N, 5.42; F, 7.39.] Bromination of the methyl group was effected by heating at reflux under an incandescent light source a mixture of 567 mg (2.22 mmole) of the phthalimide derivative, 435 mg of N-bromosuccinimide, and 59 mg of benzoyl peroxide in 25 ml of carbon tetrachloride. After one hour the mixture was cooled to room temperature, filtered, and concentrated in vacuo to give 720 mg of the crude bromomethyl phthalimide derivative. Using the general method of Example 1 with 284 mg of this bromomethyl phthalimide derivative instead of 2-(chloromethyl)-N,N-dimethylaniline in isopropyl alcohol produced the phthalimide derivative of 2-[(1H-benzimidazol-2-ylthio)methyl]-4-fluorobenzenamine. The residue from the dichloromethane extraction (as in Example 1) was washed with diethyl ether and purified by column chromatography, giving 190 mg of the phthalimide derivative as a white solid. Using the method of Example 3 with 104 mg (0.248 mmole) of this phthalimide derivative of 2-[(1H-benzimidazol-2-ylthio)methyl]-4-fluorobenzenamine instead of the title product of Example 2 produced the corresponding sulfoxide. The reaction mixture was diluted with dichloromethane, washed with aqueous sodium bicarbonate, dried over sodium sulfate, filtered, and concentrated in vacuo to give 119 mg of the sulfoxide as an oil. The sulfoxide was stirred in a solution of 0.14 ml of hydrazine hydrate in 5 ml of ethanol for two hours to remove the phthalimide group. The mixture was concentrated in vacuo to a solid, which was washed sequentially with 3% aqueous ammonium hydroxide and water, and air-dried to give 50 mg of the title compound: m.p. 184–185° C. Analysis. Calc'd. for $C_{14}H_{12}N_3FOS$: C, 58.12; H, 4.18; N, 14.52; F, 6.57. Found: C, 58.11; H, 4.21; N, 14.54; F,6.34.

EXAMPLE 77

2-[(1H-Benzimidazol-2-ylsulfinyl)methyl]-3,4,5-trimethylbenzenamine hemihydrate

The title compound, m.p. 145° C. (softening) with decomp. at 235° C., was prepared by the method of Example 39 using 3,4,5-trimethylaniline instead of 4-methoxy-3,5-dimethylaniline and using sulfuric acid instead of hydrochloric acid during the reaction according to Example 2. Analysis. Calc'd. for $C_{17}H_{19}N_3OS*H_2O$: C, 63.33; H, 6.25; N, 13.03; F, 9.95. Found: C, 63.53; H, 5.92; N, 13.16; F, 9.60.

EXAMPLE 78

2-[[(5-Methoxy-1H-benzimidazol-2-yl)sulfinyl]methyl]-4-methoxy-3,5-dimethylbenzenamine The title compound, m.p. 149–155° C., was prepared by the method of Example 39 using 2-mercapto-5-methoxybenzimidazole instead of 2-mercaptobenzimidazole. Analysis. Calc'd. for $C_{18}H_{21}N_3O_3S$: C, 60.15; H, 5.89; N, 11.69; F, 8.92. Found: C, 59.71; H, 5.83; N, 11.56; F, 8.64.

EXAMPLE 79

3-[(1H-Benzimidazol-2-ylthio)methyl]-2-pyridinamine hemihydrate

A mixture of 9.6 g (63 mmole) of 2-mercaptobenzimidazole and 7.7 g (62 mmole) of 3-hydroxymethyl-2-pyridinamine was dissolved in 60 ml of 48% aqueous hydrobromic acid and 60 ml of acetic acid and heated to reflux. After being cooled to room temperature, the mixture was poured into water and made alkaline with potassium carbonate. The oil that separated solidified upon addition of diethyl ether to the aqueous mixture. The solid was collected by filtration, washed with portions of diethyl ether and water, and air dried to yield 12.4 g of the title compound as an analytically pure hemihydrate. Structure assignment was supported by the nmr and infrared spectra and by elemental analysis. Analysis. Calc'd. for $C_{13}H_{12}N_4S*½H_2O$: C,58.84; H, 4.93; N, 21.11; S, 12.08. Found: C, 59.06; H, 4.48; N, 20.82; S, 12.16.

EXAMPLE 80

3-[(1H-Benzimidazol-2-ylsulfonyl)methyl]-2-pyridinamine

A suspension of 4.0 g (15 mmole) of 3-[(1H-benzimidazol-2-ylthio)methyl]-2-pyridinamine hemihydrate (see Example 79) in 50 ml of dichloromethane was cooled in an ice bath. A solution of 3.0 g (15 mmole) of ca. 85% m-chloroperbenzoic acid in the minimum amount of dichloromethane needed to form a solution was then added dropwise with stirring. After addition was complete, another 3.0 g of ca. 85% m-chloroperbenzoic acid was added. The reaction was quenched with 10 drops of dimethylsulfide. The mixture was washed with saturated aqueous sodium bicarbonate. The organic phase was concentrated in vacuo and chromatographed on silica gel (using ethanol-dichloromethane-triethylamine as eluent). Initial fractions yielded 249 mg of the title sulfone. Structure assignment was supported by the nmr and infrared spectra and by elemental analysis. Analysis. Calc'd. for $C_{12}H_{12}N_4SO_2$: C, 54.15; H, 4.19; N, 19.43. Found: C, 53.79; H, 4.09; N, 19.29.

EXAMPLE 81

3-[(1H-Benzimidazol-2-ylsulfinyl)methyl]-2-pyridinamine hydrate

Later fractions from the chromatographic separation of Example 80 yielded 653 mg of the title sulfoxide. Structure assignment was supported by the nmr and infrared spectra and by elemental analysis. Analysis. Calc'd. for $C_{13}H_{12}N_4SO*H_2O$: C, 53.77; H, 4.16; N, 12.29; S, 11.04. Found: C, 53.59; H, 4.34; N, 18.93; S, 11.26.

EXAMPLE 82

3-[(1H-Benzimidazol-2-ylthio)methyl]-N,N-dimethyl-2-pyridinamine

To a cold (ca. −78° C.) solution of 2.9 g (21 mmole) of 3-methyl-2-(N,N-dimethylamino)pyridine in 35 ml of tetrahydrofuran was added dropwise 15 ml (23 mmole) of 1.55 M butyllithium in hexane. The mixture was stirred at 0° C. for four hours and then recooled to ca. −78° C. Trimethyl borate (2.65 ml, ca. 23 mmole) was added dropwise and the mixture was stirred at 0° C. After one hour 2.9 ml of 30% hydrogen peroxide was added and the mixture was stirred at 25° C. After another hour, the reaction mixture was poured into water and extracted with several portions of diethyl ether. The combined ether extracts were dried over magnesium sulfate, filtered, and concentrated in vacuo to an oil. Chromatography on silica gel (using ethanol-toluene as eluent) yielded 600 mg of 3-hydroxymethyl-2-(N,N-dimethylamino)pyridine, as confirmed by the nmr and infrared spectra. Using the method of Example 79 with 3-hydroxymethyl-2-(N,N-dimethylamino) pyridinamine instead of 3-hydroxymethyl-2-pyridinamine yielded the title compound, which was used in subsequent reactions without further purification. Structure assignment was supported by the nmr and infrared spectra.

EXAMPLE 83

3-[(1H-Benzimidazol-2-ylsulfinyl)methyl]-N,N-dimethyl-2-pyridinamine ⅓ hydrate The title compound was prepared by the method of Example 80 using 1.5 g of 3-[(1H-benzimidazol-2-ylsulfinyl)methyl]-N,N-dimethyl-2-pyridinamin (see Example 82) instead of 3-[(1H-benzimidazol-2-ylthio) methyl]-2-pyridinamine hemihydrate and using chloroform as solvent instead of dichloromethane. Structure assignment was supported by the nmr and infrared spectra and by elemental analysis. Analysis. Calc'd. for $C_{15}H_{16}N_4OS*⅓H_2O$: C, 58.84; H, 5.48; N, 18.29; S, 10.44. Found: C, 59.24; H, 5.31; N, 18.10; S, 10.05.

EXAMPLE 84

6-[(1H-benzimidazol-2-ylthio)methyl]-2-pyridinamine hemihydrate

To a cold (ca. 0° C.) solution of 86.4 g (0.88 mole) of 2-amino-6-methylpyridine and 101 g (0.96 mole) of triethylamine in 1.0 liter of dichloromethane was added dropwise a solution of 106.1 g (0.88 mole) of trimethylacetyl chloride in 100 ml of dichloromethane. After stirring an hour after addition was completed, the mixture was poured into water and the layers separated. The aqueous layer was extracted with dichloromethane. The organic layers were combined and washed with water, dried over magnesium sulfate, filtered, and concentrated in vacuo to an oil that crystallized upon standing. The solid was triturated with hexane and collected by filtration, giving 115 g of 2-(trimethylacetamido)-6-methylpyridine. A 22.6 g (0.12 mmole) portion of the amide derivative was suspended in 250 ml of carbon tetrachloride containing 22.9 g (0.12 mmole) of N-bromosuccinimide and 100 mg of 2,2'-azabisisobutyronitrile. The mixture was heated at reflux under a sun lamp for one hour, after which insolubles were removed by filtration. The filtrate was concentrated in vacuo to an oil consisting of a mixture of the 6-bromomethyl-2-(trimethylacetamido)pyridine and 6-dibromomethyl-2-(trimethylacetamido)pyridine derivatives. The crude mixture was heated at reflux for fifteen minutes with 11.7 g (78 mmole) of 2-mercaptobenzimidazole in 300 ml of isopropyl alcohol. Upon cooling, a precipitate formed and was collected and washed with portions of isopropyl alcohol and diethylether. The trimethylacetyl group was removed by heating at reflux for four hours in 300 ml of 10% aqueous hydrochloric acid. After cooling, the mixture was concentrated in vacuo to an oil. The oil was dissolved in water and made alkaline with aqueous potassium carbonate. The oil that separated solidified upon addition of dichloromethane to the aqueous mixture. The solid was collected by filtration, washed with portions of water and dichloromethane, and air dried to yield 9.6 g of the title compound as an analytically pure hemihydrate. (An additional 2.5 g of the title compound was isolated from the dichloromethane washes.) Structure assignment was supported by the nmr and infrared spectra and by elemental analysis. Analysis. Calc'd. for $C_{13}H_{12}N_4S*½H_2O$: C, 58.84; H,4.93; N, 21.11; S, 12.08. Found: C, 59.03; H, 4.40; N, 20.90; S, 12.30.

EXAMPLE 85

6-[(1H-Benzimidazol-2-ylsulfinyl)methyl]-2-pyridinamine

A suspension of 5.0 g (18.8 mmole) of 6-[(1H-benzimidazol-2- ylthio)methyl]-2-pyridinamine hemihydrate (see Example 84) in 250 ml of chloroform was cooled to −5° C. A solution of 4.2 g (20 mmole) of ca. 85% m-chloroperbenzoic acid in chloroform was added dropwise with stirring. After an additional fifteen minutes, the reaction was quenched with several drops of dimethylsulfide and concentrated in vacuo. The residue was triturated with diethyl ether, filtered, and washed with diethyl ether, yielding 2.6 g of the title compound. Structure assignment was supported by the nmr and infrared spectra and by elemental analysis. Analysis. Calc'd. for $C_{13}H_{12}N_4SO$: C, 57.33; H, 4.44; N, 20.57; S, 11.77. Found: C, 57.04; H, 4.42; N, 20.50; S, 11.87.

EXAMPLE 86

6-[[(4-Methyl-1H-benzimidazol-2-yl)-thio]methyl]-2-pyridinamine hemihydrate

A solution of 20 g (0.13 mole) of 2-methyl-6-nitroaniline in 22.9 ml of concentrated aqueous hydrochloric acid, 200 ml of tetrahydrofuran, and 350 ml of methanol was hydrogenated at room temperature using 25 psi. of hydrogen gas over 2.0 g of 5% palladium on carbon. The mixture was filtered and the filtrate was concentrated in vacuo. The residue was dissolved in 150 ml of ethanol and neutralized with 17.2 g (0.26 mole) of potassium hydroxide dissolved in 30 ml of water. Potassium ethylxanthate (23 g, 0.155 mole) was added and the mixture was heated at reflux for 18 hours. Upon cooling, a solid was collected, washed with water, and air dried to yield 6.2 g of 2-mercapto-4-methylbenzimidazole, as confirmed by the nmr and infrared spectra. The title compound (1.5 g) was prepared by the method of Example 84 using 1.6 g of 2-mercapto-4-methylbenzimidazole instead of 2-mercaptobenzimidazole. Structure assignment was supported by the nmr and infrared spectra and by elemental analysis. Analysis. Calc'd. for $C_{14}H_{14}N_4S*½H_2O$: C, 60.19; H, 5.01;N, 20.05; S, 11.45. Found: C, 60.49; H, 5.03; N, 20.41; S, 11.76.

EXAMPLE 87

6-[[(4-Methyl-1H-benzimidazol-2-yl)-sulfinyl]methyl]-2-pyridinamine

The title compound (450 mg) was prepared by the method of Example 85 using 600 mg (2.2 mmole) of 6-[[(4-methyl-1H-benzimidazol-2-yl)thio]methyl]-2-pyridinamine (see Example 8) instead of 6-[(1H-benzimidazol-2-ylthio)methyl]-2-pyridinamine. Structure assignment was supported by the nmr and infrared spectra and by elemental analysis. Analysis. Calc'd. for $C_{14}H_{14}N_4SO$: C, 58.72; H, 4.93; N, 19.57; S, 11.20. Found: C, 58.70; H, 4.86; N, 19.60; S, 10.88.

EXAMPLE 88

6-[[(5-Methyl-1H-benzimidazol-2-yl)thiol-methyl]-2-pyridinamine hemihydrate

A mixture of 12.2 g (0.1 mole) of 3,4-diaminotoluene, 35 ml of carbon disulfide, and 4.0 g (0.1 mole) of sodium hydroxide was heated at reflux in 350 ml of ethanol. After 2.5 hours the mixture was concentrated in vacuo. The residue was suspended in 200 ml of 4% aqueous hydrochloric acid, and the product was collected by filtration, washed sequentially with water and diethyl ether, and air dried to yield 12.2 g of 2-mercapto-5-methylbenzimidazole, as confirmed by the nmr and infrared spectra. The title compound (2.0 g) was prepared by the method of Example 84 using 1.6 g (9.7 mmole) of 2-mercapto-5-methylbenzimidazole instead of 2-mercaptobenzimidazole. Structure assignment was supported by the nmr and infrared spectra and by elemental analysis. Analysis. Calc'd. for $C_{14}H_{14}N_4S$: C, 60.19; H, 5.01; N,20.05; S, 11.47. Found: C, 59.80; H, 5.05; N, 20.00; S, 11.17.

EXAMPLE 89

6-[[(5-Methyl-1H-benzimidazol-2-yl)-sulfinyl]methyl]-2-pyridinamine

The title compound (240 mg) was prepared by the method of Example 85 using 1.0 g (3.7 mmole) of 6-[[(5-methyl-1H-benzimidazol-2-yl)thio]methyl]-2-pyridinamine (see Example 88) instead of 6-[(1H-benzimidazol-2-ylthio)methyl]-2-pyridinamine. Structure assignment was supported by the nmr and infrared spectra and by elemental analysis. Analysis. Calc'd. for $C_{14}H_{14}N_4SO$: C, 58.72; H, 4.93; N, 19.57; S, 11.20. Found: C, 58.62; H, 4.91; N, 19.60; S, 10.99.

EXAMPLE 90

6-[[(5-Methoxy-1H-benzimidazol-2-yl)-thio]methyl]-2-pyridinamine

The title compound was prepared by the method of Example 84 using 7.0 g of 2-mercapto-5-methoxybenzimidazole instead of 2-mercaptobenzimidazole. Structure assignment was supported by the nmr spectrum.

EXAMPLE 91

6-[[(5-Methoxy-1H-benzimidazol-2-yl)sulfinyl]methyl]-2-pyridinamine

The title compound (940 mg) was prepared by the method of Example 85 using 4.67 g (16.3 mmole) of 6-[[(5-methoxy-1H-benzimidazol-2-yl)thio]methyl]-2-pyridinamine (see Example 90) instead of 6-[(1H-benzimidazol-2-ylthio)methyl]-2-pyridinamine. Structure assignment was supported by the nmr and infrared spectra and by elemental analysis. Analysis. Calc'd. for $C_{14}H_{14}N_4SO_2$: C, 55.62; H, 4.67; N, 18.53; S, 10.60. Found: C, 55.52; H, 4.59; N, 17.86; S, 10.35.

EXAMPLE 92

6-[[(5-Chloro-1H-benzimidazol-2-yl)thio]-methyl]-2-pyridinamine

A solution of 20 g (0.12 mole) of 3-chloro-6-nitroaniline in 350 ml of methanol was hydrogenated over 5% palladium on carbon to yield 24.9 g of the corresponding diamino compound. Reaction of the diamino compound with potassium ethylxanthate using the method described in Example 86 yielded 19 g of 5-chloro-2-mercaptobenzimidazole, as confirmed by elemental analysis. The title compound (1.8 g) was prepared by the method of Example 84 using 3.6 g (19 mmole) of 5-chloro-2-mercaptobenzimidazole instead of 2-mercaptobenzimidazole. Structure assignment was supported by the nmr and infrared spectra.

EXAMPLE 93

6-[[(5-Chloro-1H-benzimidazol-2-yl)-sulfinyl]methyl]-2-pyridinamine

The title compound (250 mg) was prepared by the method of Example 85 using 1.5 g (5.2 mmole) of 6-[[(5-chloro-1H-benzimidazol-2- yl)thio]methyl]-2-pyridinamine (see Example 92) instead of 6-[(1H-benzimidazol-2-ylthio)-methyl]-2-pyridinamine. Structure assignment was supported by the nmr spectrum and by elemental analysis. Analysis. Calc'd. for $C_{13}H_{11}N_4ClSO$: C, 50.90; H, 3.61; N, 18.26; S, 10.45; Cl, 11.56. Found: C, 50.97; H, 3.60; N, 18.45; S, 10.47; Cl, 11.74.

EXAMPLE 94

6-[[[5-(Trifluoromethyl)-1H-benzimidazol-2-yl]thio]methyl]-2-pyridinamine

A solution of 50 g (0.24 mole) of 4-(trifluoromethyl)-2-nitroaniline in 500 ml of ethanol was hydrogenated over 10% palladium on carbon to yield 21.0 g of the corresponding diamino compound. Reaction of 20.0 g of the diamino compound with carbon disulfide using the method described in Example 88 yielded 22.9 g of 5-(trifluoromethyl)-2-mercaptobenzimidazole, as confirmed by elemental analysis. The title compound (1.5 g) was prepared by the method of Example 84 using 5.7 g (26 mmole) of 5-(trifluoromethyl)-2-mercaptobenzimidazole instead of 2-mercaptobenzimidazole. Structure assignment was supported by the nmr and infrared spectra.

EXAMPLE 95

6-[[[5-(Trifluoromethyl)-1H-benzimidazol-2-yl]sulfinyl]methyl]-2-pyridinamine

The title compound (900 mg) was prepared by the method of Example 85 using 1.5 g (4.6 mmole) of 6-[[[5-(trifluoromethyl)-1H-benzimidazol-2-yl]thio]methyl]-2-pyridinamine (see Example 94) instead of 6-[(1H-benzimidazol-2-ylthio)methyl]-2-pyridinamine. Structure assignment was supported by the nmr and infrared spectra and by elemental analysis. Analysis. Calc'd. for $C_{14}H_{11}N_4F_3SO$: C, 49.41; H, 3.26; N, 16.46; S, 9.42. Found: C, 49.42; H, 3.29; N, 16.30; S, 9.49.

EXAMPLE 96

6-[[(5-Ethoxy-1H-benzimidazol-2-yl)thio]-methyl]-2-pyridinamine

A solution of 51.3 g (0.28 mole) of 4-ethoxy-2-nitroaniline in methanol was hydrogenated over 5% palladium on carbon to yield 63.4 g of the corresponding diamino compound. Reaction of the diamino compound with potassium ethylxanthate using the method described in Example 86 yielded 43.4 g of 5-ethoxy-2-mercaptobenzimidazole, as confirmed by the nmr and infrared spectra. The title compound (1.0 g) was prepared by the method of Example 84 using 3.7 g of 5-ethoxy-2-mercaptobenzimidazole instead of 2-mercaptobenzimidazole. The title compound was used in subsequent reactions without further characterization.

EXAMPLE 97

6-[[(5-Ethoxy-1H-benzimidazol-2-yl)-sulfinyl]methyl]-2-pyridinamine

The title compound (700 mg) was prepared by the method of Example 85 using 900 mg (3.0 mmole) of 6-[[(5-ethoxy-1H-benzimidazol-2-yl)thio]methyl]-2-pyridinamine (see Example 96) instead of 6-[(1H-benzimidazol-2-ylthio)methyl]-2-pyridinamine. Structure assignment was supported by the nmr and infrared spectra and by elemental analysis. Analysis. Calc'd. for $C_{15}H_{16}N_4SO_2$: C, 56.95; H, 5.10; N, 17.71; S, 10.14. Found: C, 56.67; H, 4.99; N, 17.48; S, 10.27.

EXAMPLE 98

6-[[(5,6-Dimethoxy-1H-benzimidazol-2-yl)-thio]methyl]-2-pyridinamine ¾ hydrate

A solution of 62.2 g (0.31 mole) of 3,4-dimethoxy-6-nitroaniline in tetrahydrofuran was hydrogenated with Raney nickel to yield 52.7 g of the corresponding diamino compound. Reaction of the diamino compound with potassium ethylxanthate using the method described in Example 86 yielded 59 g of 5,6-dimethoxy-2-mercaptobenzimidazole as confirmed by the nmr and infrared spectra. The title compound (1.9 g) was prepared by the method of Example 84 using 4.3 g of 5,6-dimethoxy-2-mercaptobenzimidazole instead of 2-mercaptobenzimidazole. Structure assignment was supported by the nmr and infrared spectra and by elemental analysis. Analysis. Calc'd. for $C_{15}H_{16}N_4SO_2$*¾ $H_2O$: C, 54.61; H, 5.30; N, 16.98; S, 9.70. Found: C, 54.75; H, 5.13; N, 17.08; S, 9.72.

EXAMPLE 99

6-[[[(5,6-Dimethoxy-1H-benzimidazol-2-yl)-sulfinyl]methyl]-2-pyridinamine ¼ hydrate The title compound (600 mg) was prepared by the method of Example 85 using 1.6 g (5.0 mmole) of 6-[[(5,6-dimethoxy-1H-benzimidazol-2-yl)thio]methyl]-2-pyridinamine (see Example 98) instead of 6-[(1H-benzimidazol-2-ylthio)-methyl]-2-pyridinamine. Structure assignment was supported by the nmr spectrum and by elemental analysis. Analysis. Calc'd. for $C_{15}H_{16}N_4SO_3$*¼ $H_2O$: C, 53.48; H, 4.90; N, 16.63; S, 9.52. Found: C, 53.54; H, 4.57; N, 16.45; S, 9.79.

EXAMPLE 100

6-[[[(5,6-Dimethyl-1H-benzimidazol-2-yl)-thio]methyl]-2-pyridinamine

Reaction of 30 g (0.22 mole) of 4,5-dimethyl-1,2-phenylenediamine with potassium ethylxanthate using the method described in Example 86 yielded 19 g of 5,6-dimethyl-2-mercaptobenzimidazole, as confirmed by the nmr and infrared spectra and by elemental analysis. The title compound (3.0 g) was prepared by the method of Example 84 using 3.5 g of 5,6-dimethyl-2-mercaptobenzimidazole instead of 2-mercaptobenzimidazole. Structure assignment was supported by the nmr spectrum.

EXAMPLE 101

6-[[[(5,6-Dimethyl-1H-benzimidazol-2-yl)-sulfinyl]methyl]-2-pyridinamine

The title compound was prepared by the method of Example 85 using 1.5 g (5.3 mmole) of 6-[[(5,6-dimethyl-1H-benzimidazol-2-yl)thio]methyl]-2-pyridinamine (see Example 100) instead of 6-[(1H-benzimidazol-2-ylthio)-methyl]-2-pyridinamine. Structure assignment was supported by the nmr spectrum and by elemental analysis. Analysis. Calc'd. for $C_{15}H_{16}N_4SO$: C, 59.98; H, 5.37; N, 18.65; S, 10.67. Found: C, 59.67; H, 5.20; N, 18.83; S, 10.87.

EXAMPLE 102

6-[[[(4,6-Dimethyl-1H-benzimidazol-2-yl)-thio]methyl]-2-pyridinamine

A solution of 5 g (0.03 mole) of 2,4-dimethyl-6-nitroaniline in methanol was hydrogenated over 5% palladium on carbon to yield 4.0 g of the corresponding diamino compound. Reaction of the diamino compound with potassium ethylxanthate using the method described in Example 86 yielded 4.9 g of 4,6-dimethyl-2-mercaptobenzimidazole, as confirmed by the nmr and infrared spectra and by elemental analysis. The title compound (1.5 g) was prepared by the method of Example 84 using 3.5 g (20 mmole) of 4,6-dimethyl-2-mercaptobenzimidazole instead of 2-mercaptobenzimidazole. Structure assignment was supported by the nmr spectrum.

EXAMPLE 103

6-[[[(4,6-Dimethyl-1H-benzimidazol-2-yl)-sulfinyl]methyl]-2-pyridinamine

The title compound was prepared by the method of Example 85 using 1.0 g (3.5 mmole) of 6-[[(4,6-dimethyl- 1H- benzimidazol-2-yl)thio]methyl]-2-pyridinamine (see Example 102) instead of 6-[(1H-benzimidazol-2-ylthio)-methyl]-2-pyridinamine. Structure assignment was supported by the nmr and infrared spectra and by elemental analysis. Analysis. Calc'd. for $C_{15}H_{16}N_4SO$: C, 59.98; H, 5.37; N, 18.65; S, 10.67. Found: C, 59.60; H, 5.32; N, 18.47; S, 10.75.

EXAMPLE 104

6-[[[5-(Hydroxymethyl)-1H-benzimidazol-2-yl]thio]methyl]-2-pyridinamine

The title compound (600 mg) was prepared by the method of Example 84 using 2.7 g of 5-hydroxymethyl-2-mercaptobenzimidazole instead of 2-mercaptobenzimidazole. Structure assignment was supported by the nmr spectrum.

EXAMPLE 105

6-[[[5-(Hydroxymethyl)-1H-benzimidazol-2-yl]sulfinyl]methyl]-2-pyridinamine ¼ hydrate The title compound was prepared by the method of Example 85 using 350 mg of 6-[[[5-(hydroxymethyl)-1H-benzimidazol-2-yl]thio]methyl]-2-pyridinamine (see Example 104) instead of 6-[(1H-benzimidazol-2-ylthio)methyl]-2-pyridinamine. Structure assignment was supported by the nmr and infrared spectra and by elemental analysis. Analysis. Calc'd. for $C_{14}H_{14}N_4SO_2$*¼ H2O: C, 54.80; H,4.60; N, 18.25; S, 10.44. Found: C, 54.85; H, 4.70; N, 18.01; S, 10.26.

EXAMPLE 106

6-[(1H-Benzimidazol-2-ylthio)methyl]-N-(2,2-dimethylpropyl)-2-pyridinamine

A suspension of 40 g (0.21 mole) of 2-(trimethylacetamido)-6-methylpyridine (prepared as described in Example 84) in 500 ml of water was heated to 70° C. Potassium permanganate (65 g, 420 mmole) was added in eight portions over four hours and the mixture was then heated at 90° C. After 18 hours the mixture was filtered hot. The filtrate was concentrated in vacuo to about 50 ml and adjusted to about pH 3 with concentrated hydrochloric acid. The resultant precipitate was collected, washed with water, and dried in vacuo to yield 7.5 g of the 6-carboxylic acid derivative. To a suspension of 7.0 g of the carboxylic acid derivative in 50 ml of cold (ca. 0° C.) tetrahydrofuran was added dropwise 85 ml (ca. 85 mmole) of 1 M crane in tetrahydrofuran. The mixture was allowed to stir at room temperature for two hours and at 50° C. for another 18 hours. After the mixture was allowed to cool, the reaction was quenched with water. The mixture made basic with 10% aqueous sodium hydroxide and extracted with several portions of ethyl acetate. The combined organic layers were dried over magnesium sulfate, filtered, and concentrated in vacuo to an oil. Chromatography on silica gel (using ethanol-dichloromethane as eluent) yielded 1.3 g of 6-hydroxymethyl-N-(2,2-dimethylpropyl)-2-pyridinamine, as confirmed by the nmr and infrared spectra. The title compound (1.9 g) was prepared by the method of Example 79 using 1.3 g (6.7 mmole) of 6-hydroxymethyl-N-(2,2-dimethylpropyl)-2-pyridinamine instead of 3-hydroxymethyl-2-pyridinamine. Structure assignment was supported by the nmr spectrum.

EXAMPLE 107

6-[(1H-Benzimidazol-2-ylsulfinyl)methyl]-N-(2,2-dimethylpropyl)-2-pyridinamine ¼ hydrate The title compound (100 mg) was prepared by the method of Example 85 using 1.52 g (4.65 mmole) of 6-[(1H-benzimidazol-2-ylthio)methyl]-N-(2,2-dimethylpropyl)-2-pyridinamine (see Example 106) instead of 6-[(1H-benzimidazol-2-ylthio)methyl]-2-pyridinamine. Structure assignment was supported by the nmr and infrared spectra and by elemental analysis. Analysis. Calc'd. for $C_{18}H_{22}N_4SO$*¼ H2O: C, 62.31; H, 6.48; N, 16.15; S, 9.24. Found: C, 62.19; H, 6.47; N, 15.76; S, 9.09.

EXAMPLE 108

6-[(1H-Benzimidazol-2-ylthio)methyl]-N-ethyl-2-pyridinamine

The title compound (2.1 g) was prepared by the method of Example 106 using 45 g (0.30 mole) of 2-acetamido-6-methylpyridine (prepared from 2-amino-6-methylpyridine as described in Example 84 using acetyl chloride instead of trimethylacetyl chloride) instead of 2-(trimethylacetamido)-6-methylpyridine. Structure assignment was supported by the nmr and infrared spectra.

EXAMPLE 109

6-[(1H-Benzimidazol-2-ylsulfinyl)methyl]-N-ethyl-2-pyridinamine

The title compound was prepared by the method of Example 85 using 2.0 g (7.03 mmole) of 6-[(1H-benzimidazol-2-ylthio)methyl]-N-ethyl-2-pyridinamine (see Example 108) instead of 6-[(1H-benzimidazol-2-ylthio)methyl]-2-pyridinamine. Structure assignment was supported by the nmr and infrared spectra and by elemental analysis. Analysis. Calc'd. for $C_{15}H_{16}N_4SO$: C, 59.98; H, 5.37; N, 18.65; S, 10.67. found: C, 60.07; H, 5.37; N, 18.45; S, 10.61.

EXAMPLE 110

5-[(1H-Benzimidazol-2-ylthio)methyl]-2-pyridinamine ¼ hydrate

The title compound was prepared by the general method described in Example 84 using 2-amino-5-methylpyridine instead of 2-amino-6-methylpyridine. The crystalline solid was collected and washed with portions of water and diethyl ether to yield 1.8 g of the title compound. Structure assignment was supported by the nmr and infrared spectra and by elemental analysis. Analysis. Calc'd. for $C_{13}H_{12}N_4S$*¼ H2O: C, 59.86; H, 4.83; N, 21.48; S, 12.29. Found: C, 59.91; H, 4.67; N, 21.86; S, 12.45.

EXAMPLE 111

5-[(1H-Benzimidazol-2-ylsulfinyl)methyl]-2-pyridinamine ¼ hydrate

The title compound was prepared by the method of Example 85 using 1.0 g (3.9 mmole) of 5-[(1H-benzimidazol-2-ylthio)methyl]-2-pyridinamine (see Example 110) instead of 6-[(1H-benzimidazol-2-ylthio)methyl]-2-pyridinamine. Structure assignment was supported by the nmr and infrared spectra and by elemental analysis. Calc'd. for $C_{13}H_{12}N_4SO$*¼ H2O: C, 56.40; H, 4.55; N, 20.24; S, 11.58. Found: C, 56.35; H, 4.46; N, 20.25; S, 11.66.

BIOLOGICAL EVALUATION

The compounds of this invention exhibited gastric anti-secretory activity in canines, as indicated by inhibition in vitro of $(H^+/K^+)$-ATPase obtained from canine gastric mucosa and by inhibition in vivo of gastric acid secretion in dogs. The antisecretory activity of the compounds of this invention illustrated in the Examples was determined by the following methods.

Inhibition of $(H^+/K^+)$-ATPase from Canine Gastric Mucosa

Mongrel dogs weighing 15 to 25 kilograms were fasted for twenty-four hours, with water provided ad libitum. The animals were anesthetized with pentobarbital and the stomachs were removed. Subsequent tissue manipulations and subcellular fractionations were performed at 0° C. to 4° C. After the stomachs were cut open and rinsed with tap water, the antral and cardiac regions were removed and the remaining tissue was rinsed three times in saline. The glandular mucosa was removed mechanically, chopped finely in a medium containing 10 mM Tris hydrochloride (pH 7.4) and 250 mM sucrose, and homogenized. The homogenate was centrifuged at 20,000×g for twenty minutes and the pellet discarded. The supernatant was then centrifuged at 150,000×g for ninety minutes and the supernatant discarded. The pellet was resuspended in the Tris-HCl/sucrose medium by homogenization. Part (2 ml) of the resultant microsomal suspension was layered onto a step gradient consisting of 9 ml of 15% sucrose above 12 ml of 30% sucrose, each sucrose solution being buffered with 10 mM Tris hydrochloride (pH 7.4) containing 0.01% sodium azide. The microsomes retained at the 15%–30% sucrose interface, after centrifugation at 250,000×g for sixty minutes, were used as the source of $(H^+/K^+)$-ATPase. Microsomal preparations were lyophilized, a process that assured potassium ion permiability, and stored at −10° C. until used.

$(H^+/K^+)$-ATPase activity for each test compound was determined, in duplicate, by measuring the release of inorganic phosphate, which was assayed according to the method of J. ChandraRajan and L. Klein, Anal. Biochem., 72, 407 (1976). The $(H^+/K^+)$-ATPase assay medium consisted of 20 mm mes-Tris (pH 6.0), 5 mM magnesium chloride, 25 mM sucrose, and 4 mM Tris-ATP with or without 20 mM potassium chloride in a total volume of 2 ml. Microsomal suspensions (20 to 60 mcl, containing about 25 mcg protein) were added to the assay medium, without Tris-ATP, and then preincubated with a test compound for thirty minutes at 37° C. The assay was initiated by adding Tris-ATP and the mixture was incubated another thirty minutes at 37° C. A 200-mcl aliquot of the assay mixture was then added to 1.4 ml of a solution consisting of 0.1 M sodium acetate (pH 4.0) and 10% sodium dodecylsulfate, followed by the addition of 200 mcl each of 1% ammonium molybdate and 1% ascorbic acid. At least fifteen minutes later, the optical absorbance at 870 nm (which was proportional to inorganic phosphate concentration up to 100 nmoles per tube, as determined by a standard curve) was obtained. Enzyme activity was linear with incubation time.

$(H^+/K^+)$-ATPase activity is represented by the difference between the measured activities in the presence of potassium-ion ($K^+$-stimulated) and in the absence of potassium ion (basal). The concentration of a test compound required to inhibit 50% of the $(H^+/K^+)$-ATPase activity (i.e., the $IC_{50}$) was determined at least in duplicate using linear regression analysis of results obtained for three different compound concentrations ranging from 0.1 mcM to 0.2 mM. If the $IC_{50}$ for a test compound could not be determined for the concentration range tested, percent inhibition of $(H^+/K^+)$-ATPase was obtained for the compound at 0.1 mM.

Inhibition of Gastric Acid Secretion in Gastric Fistula Beagle Dogs

Adult female beagle dogs weighing 6 to 11 kilograms obtained from Laboratory Research Enterprises (Kalamazoo, Mich.) or from Hazelton Research Animals (Cumberland, Va.) were surgically implanted with a simple Thomas-type gastric cannula. After recovery from surgery, the dogs were trained to stand quietly, fully conscious, in Pavlov-type dog restraining slings and were acclimated to intravenous infusion of histamine dihydrochloride. During the course of these studies, no dog was used more than once a week. All dogs were deprived of food, but not water, for 18 hours prior to each assay. Each dog was initially infused with 0.15 M sodium chloride solution at a constant rate of 6.5 mg/hr. The volume of gastric secretions, collected in plastic bottles affixed to the cannula, were measured to the nearest 0.1 ml at 30 minute intervals. One of the following protocols was followed, depending on the route chosen for administration of test compound.

Intravenous dosing: Following a 30-minute basal secretion period, test compounds were administered intravenously (i.v.). At the end of an additional 30 minute period, the saline infusion was replaced with histamine dihydrochloride in saline administered at a rate 15 mcg per kilogram of body weight per hour. Histamine stimulation was maintained for a maximum of four hours during which time gastric secretions were collected every 30 minutes. The pH and titratable acidity were determined for samples from each collection period.

Intragastric dosing: Following a 30-minute basal secretion period, he collection bottles were removed, dosing plugs here inserted, and test compounds were administered intragastrically (i.g.) At the end of a 30-minute drug absorption period, the stomachs were emptied, the collection bottles were reattached, and collections were resumed at 30-minute intervals. Simultaneously, the saline infusion was replaced with a continuous intravenous infusion of histamine dihydrochloride in saline administered for four hours at a rate 15 mcg per kilogram of body weight per hour.

Intraduodenal dosing: Dogs were also equipped with duodenal cannulas for intraduodenal (i.d.) administration of test compounds. Dosing was otherwise performed as described for intragastric dosing.

Data from each protocol were analyzed for three gastric sample variables: volume of gastric juice, acid concentration, and total acid output. Percent inhibition for each four-hour experimental period was determined for each parameter by comparison with 3 to 4 controls in which only food was given. Estimates of $ED_{50}$'s were determined from dose response curves.

Inhibition of Gastric Acid Secretion in Meal-Stimulated Pavlov Pouch Dog

Adult female beagle dogs weighing 6 to 10 kilograms were obtained from Laboratory Research Enterprises (Kalamazoo, Mich.) or from Hazelton Research Animals (Cumberland, Va.). Surgical implantation of a Thomas-type gastric cannula into an innervated Pavlov pouch of each dog was performed by the method reported by L. Burrows et al., J. Surgical Res., 4, 147 (1964). After recovery from surgery, the dogs were trained to stand quietly, fully conscious, in Pavlov-type dog restraining slings. All dogs were deprived of food, but not water, for 24 hours prior to each assay. Basal acid secretion was measured by collecting from the cannulas for 30 minutes before dosing with a test compound. Solutions of the test compounds in iso-osmotic phosphate buffer (pH 7.4) were given either intravenously or directly into the Pavlov pouch. After 30 minutes the pouch was drained. The dogs were then fed 320 grams of dog food and gastric acid secretions were collected each half hour for four hours.

Controls were determined in the same way except that only food (i.e., no test compound) was administered.

Data were analyzed for three different variables: volume of gastric juice, acid concentration, and total acid output. Percent inhibition for the four-hour experimental period was determined for each parameter by comparison with 3 to 4 controls. Estimates of $ED_{50}$ were determined from dose response curves. Results are shown in Table 1.

TABLE 1

Pharmacological Test Results.

| Compound [Product of Example No.] | $(H^+/K^+)$-ATPase IC50 (mcM) | Gastric-Fistula Beagle % Inhibition (3 mg/kg dose) | Pavlov-Pouch Dog % Inhibition (dose (mg/kg)) |
|---|---|---|---|
| 3 | 4.3 | 59 i.v. | 87 (10 mg/kg) |
|  |  | 53 i.d. | 20 (1 mg/kg) |
| 4 | 0.7 | 14 i.v. | 3 (3 mg/kg) |
| 6 | >100 | 37 i.v. |  |
| 8 | 7.4 | 60 i.v. |  |
| 10 | 13.5 | 44 i.v. |  |
| 12 | 11.0 | 90 i.d. | 54 (10 mg/kg) |
|  |  |  | 19 (3 mg/kg) |
| 16 | 130.0 | 24 i.v. |  |
| 18 | 24.0 | 13 i.v. |  |
| 20 | 1.6 | 37 i.v. | 22 (3 mg/kg) |
| 22 | 9.3 | 70 i.v. |  |
| 24 | 0.66 | 73 i.v. |  |
| 26 | 2.1 | 67 i.v. |  |
| 28 | 3.2 | 93 i.v. | 43 (3 mg/kg) |
|  |  | 44 i.d. |  |
| 30 | 0.85 |  |  |
| 32 | 0.64 | 21 i.d. |  |
| 34 | 4.2 | 91 i.v. | 79 (3 mg/kg) |
|  |  | 66 i.d. |  |
|  |  | 43 i.g. |  |
| 36 | 5.4 | 96 i.v. |  |
|  |  | 72 i.d. |  |
| 37 | 2.0 | 62 i.d. |  |
| 38 | 3.9 | 21 i.d. |  |
| 39 | 0.2 | 53 i.d. |  |
| 41 | 7.9 |  |  |
| 43 | 12.0 |  |  |
| 45 | 24.0 |  |  |
| 47 | 4.4 | 37 i.d. |  |
| 49 | >100 | 16 i.d. |  |
| 51 | 2.6 | 19 i.d. |  |
| 53 | 0.6 | 79 i.d. |  |
| 55 | 0.82 |  |  |
| 57 | 60.0 |  |  |
| 59 | 2.7 |  |  |
| 61 | 5.3 |  |  |
| 63 | 0.71 |  |  |
| 65 | 1.5 |  |  |
| 67 | 8.5 |  |  |
| 69 | 153.0 | 28 i.d. |  |
| 71 | >100 | 7 i.d. |  |
| 73 | >100 |  |  |
| 75 | 120.0 |  |  |
| 76 | 24.9 |  |  |
| 77 | 16.0 |  |  |
| 78 | 2.1 | 31 i.d. |  |
| 81 | 100 | 41 i.v. |  |
| 83 | 8.6 | 15 i.v. |  |
| 85 | 2.5 | 59 i.v. |  |
| 87 | 2.2 |  |  |
| 89 | 1.68 |  |  |
| 91 | 4.5 | 46 i.v. |  |
| 93 | 6.9 |  |  |
| 95 | 6.95 |  |  |
| 97 | 3.1 |  |  |
| 99 | 23.7 |  |  |
| 101 | 0.72 |  |  |
| 103 | 1.8 |  |  |
| 105 | 9.5 |  |  |
| 107 | 9.1 |  |  |
| 109 | 20.0 | 58 i.d. |  |
| 111 | 34.8 |  |  |
| omeprazole | 1.9 |  |  |

Enzymatic Assay for HCMV Protease (Assemblin) Inhibitors

The compounds of this invention exhibited antiviral activity as indicated by inhibition in vito of herpesvirus protease and by inhibition in vivo of HCMV infectivity. The antiviral activity of the compounds of this invention illustrated in the Examples was determined by the following methods.

The enzymatic assay for assemblin inhibitors compared the rate of product appearance between a control reaction containing no inhibitor and one that contained a known concentration of a potential inhibitor. There were two phases to the enzyme reaction. The first was a period of incubation of enzyme in the presence of inhibitor, but in the absence of the substrate. This incubation allowed for the inhibitor to bind and potentially block the enzyme from hydrolyzing the substrate. The second phase was started by adding the substrate and measuring the rate of product production.

Assay Components:

Recombinant HCMV protease:

HCMV protease was purified from *E. coli* expressing a DNA construction encoding the protease domain of the $U_L 80$ open reading frame of human cytomegalovirus strain AD169. The construction also encoded six additional histidine residues at the amino terminus of the protease. These additional histidine residues provided an affinity ligand by which it was purified using nickel-nitriloacetic acid-agarose (Qiagen).

The purified protease was stored as a 1–3 mg/ml stock solution in 50 mM sodium phosphate buffer, pH 7.4; 300 mM sodium chloride; 100 mM imidazole; 50% (v/v) glycerol. This stock was diluted with assay buffer to 4.8 $\mu$g/ml. A 100 $\mu$L aliquot of this solution was used in the enzyme reaction.

A specific substrate was synthesized based on the cleavage specificity of HCMV protease at the "maturation site" of the assembly protein (F. Liu and B. Roizman, *J. Virol.* 65, 5149 (1991), and A. R. Welch, et al, *J. Virol.*, 65 4091 (1991)). The assembly protein maturation site has the sequence . . . AGVVNA*SCRLATA . . . (SEQ ID NO. 1); the substrate used was dabcycl-Abu-GVVNASARLA-edans (SEQ ID NO. 2) (DE2). Upon excitation at 360 nm the edans chromophore emitted light (fluoresces) at 490 nm that was absorbed by the dabcyl chromophore (Emax=460 nm). However, when the two chromophores are separated because of hydrolysis of the peptide moiety by HCMV protease the edans fluorescence was no longer quenched and an increase in fluorescence was realized. DE2 was stored as a stock solution at 160 $\mu$g/ml in dimethyl sulfoxide. This was diluted 10-fold with assay buffer to give a concentration of 16 $\mu$g/ml just before use. An aliquot of 50 $\mu$L was used in the reaction.

An assay Buffer (10 mM sodium phosphate buffer, pH 7.4; 150 mM sodium acetate; 0.1% CHAPS; and 20% (v/v) glycerol) was used to dilute stock solutions of enzyme and substrate.

Inhibitors were dissolved in dimethyl sulfoxide at 16-times the final assay concentration. A 10 µL aliquot of this inhibitor solution was used in the reaction.

A 100 µL aliquot of enzyme solution (4.8 µg/ml) was mixed with 10 µL of inhibitor solution in a 96-well plate cell and incubated at 22° C. for 30 minutes. Control reactions contained 10 µL of dimethylsulfoxide instead of inhibitor solution. After the preincubation was completed, 50 µL of substrate solution was added and the fluorescence recorded every 5 minutes for a period of 30 minutes. All reactions were run in triplicate with the exception of the uninhibited control reaction which was replicated 6-fold. The change in fluorescence was recorded over time and an average rate for each set of 3 reactions was calculated. Fluorescence assays were subject to spurious various due to factors such as dust in the 96-well plate; such results were omitted from the calculation of relative rates.

ANTIVIRAL ASSAYS

These complimentary assays tested the ability of a compound to inhibit the production of new virus and the toxicity of the compound to the host cells. It was important that both assays be performed simultaneously in order to compare the results directly since, toxicity may indirectly reduce viral yield.
Abbreviations:
DMEM—Dulbecco's Modified Eagle Medium; commercially available.
FES—fetal bovine serum; commercially available and contains unknown factors necessary for growth of cells in culture.
PBS—phosphate buffered saline: 10 mM sodium phosphate buffer, pH 7.4, 120 mM sodium chloride, 2.7 mM potassium chloride.

Antiviral Assay

Viral yield was estimated by measuring the amount of a viral antigen produced 4 days post infection with a monoclonal antibody to an abundant "immediate early" viral protein. An enzyme-linked (horseradish peroxidase) secondary antibody specific to the primary (mouse) antibody was used to measure the amount of viral antigen. Test compounds were diluted to 2-times the desired final concentration in DMEM+5% FBS. One hundred microliters of this solution was placed in each well of a 96-well plate. This was performed once for the antiviral 96-well plate and again for a cytotoxicity plate. Two controls were also included for both plates; a no drug control and a ganciclovir control. Ganciclovir was included because it has known antiviral activity for HCMV. All cells were prepared by harvesting human foreskin fibroblasts, MRHF, with trypsin and re-suspending at a concentration of $5 \times 10^5$ cells per ml in DMEM. Infected cells were prepared by infecting these with HCMV (strain AD169) at a multiplicity of infection=0.2. One hundred microliters of uninfected cells ($5 \times 10^4$ cells) were added to the appropriate wells of the cytotoxicity plate. In a similar manner 100 µl of infected cells ($5 \times 10^4$ cells) were added to the appropriate wells of the antiviral plate. Additionally, uninfected cells not treated with test compound were included as controls on the antiviral plate. Plates were incubated for 96 hours at 37° C. in 5% $CO_2$ atmosphere and processed to measure the amount of viral antigen and toxicity.

Enzyme Linked ImmunoSorbant Assay (ELISA) for HCMV Antigens

The following was performed on the antiviral plate only. Media was removed and cells were fixed with 1:1 acetone:methanol for 15 minutes at −20° C. Fixative was removed and cells were washed once with PBS containing 0.05% Tween20. In order to block nonspecific binding of antibodies each well was incubated with PBS containing 3% (w/v) bovine serum albumin (BSA) for 1 hour at 22° C. The blocking solution was removed and the cells were washed once with PBS containing 0.05% Tween20 before incubating with 1:100 dilution of primary antibody in PBS containing 3% BSA for 2 hours at 22° C. The primary antibody was a monoclonal antibody (mouse source) specific to the immediate early nuclear antigen of HCMV and was commercially available (Dupont). The 10 antibody solution was removed and the plate was rinsed 5 times with PBS containing 1% (v/v) Triton X-100 (PBST) before incubating with secondary antibody diluted 1:1000 in PBS containing 3% BSA for 2 hours at 22° C. The secondary antibody (goat source) recognized the murine-specific determinants of the 1° antibody and was covalently linked to horseradish peroxidase (Sigma). The plate was rinsed 5 times with PBST and once with deionized water before adding 100 µl TMB substrate solution and incubating 30 minutes at 22° C. The reaction was stopped by adding 100 µL of phosphoric acid and the OD at 450 nm recorded. TMB (3,3',5,5' tetramethylbenzidine) was the substrate for the horseradish peroxidase linked to the 2° antibody. It was made from a commercially available kit (Kirkegaard & Perry Laboratories, Inc.). Antiviral activity was calculated by comparing the amount of viral antigen produced in drug treated wells with that produced in wells absent of drug.

TABLE 2

| COMPOUND | Assemblin Inhibition % Inhibition at 100 µm | HCMV cell $EC_{50}$ (µm) |
|---|---|---|
| omeprazole | 0 | 93 |
| 10 | 43 | |
| 12 | 26 | |
| 20 | 60 | |
| 22 | 35 | |
| 32 | 52 | |
| 39 | 46 | |
| 41 | 67 | 59 |
| 43 | 74 | 23 |
| 45 | 51 | |
| 47 | 40 | |
| 53 | 85 | 13 |
| 57 | 66 | |
| 59 | 71 | |
| 71 | 44 | |
| 73 | 50 | |
| 78 | 82 | 22 |
| 83 | 83 | |

Regardless of the route of administration selected, the compounds of the present invention are formulated into pharmaceutically acceptable dosage forms by conventional methods known to those skilled in the art. The compounds may be formulated using pharmacologically acceptable acid addition or base addition salts. Moreover, the compounds or their salts may be used in a suitable hydrated form.

The compounds can be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating viral infections with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 1.0 mcg/kg to 500 mg/kg, preferably in the range of about 10 to 100 mg/kg orally or about 1.0 to 20 mg/kg intravenously.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Sweetening and flavoring agents and preservatives can also be included where appropriate.

Although this invention has been described with respect to specific embodiments, the details of these embodiments are not to be construed as limitations.

What is claimed is:

1. A method of treating a herpetoviridael infection in a subject in need of such treatment, said method comprising treating the subject with a therapeutically effective amount of a sulfur-containing benzimidazole compound, wherein the compound is an inhibitor of a ($H^+/K^+$) ATPase and an inhibitor of a herpetoviridae protease.

2. The method of claim 1 wherein the benzimidazole compound contains a sulfur radical selected from the group consisting of sulfoxide, alkylthio, and sulfone.

3. The method of claim 1 wherein the benzimidazole compound contains a divalent sulfur bridge.

4. The method of claim 2 wherein the benzimidazole compound contains a sulfone radical.

5. The method of claim 2 wherein the benzimidazole compound contains a sulfoxide radical.

6. The method of claim 4 wherein the herpetoviridae is selected from the group of viruses consisting of herpes simplex viruses, cytomegalovirus, herpes varicellazoster, Epstein-Barr, HHV6, HHV7, pseudorabies, and rhinotracheitis.

7. The method of claim 5 wherein the herpetoviridae is selected from the group of viruses consisting of herpes simplex viruses, cytomegalovirus, herpes varicellazoster, Epstein-Barr, HHV6, HHV7, pseudorabies, and rhinotracheitis.

8. The method of claim 4 wherein the herpetoviridae protease is a serine herpetoviridae protease.

9. The method of claim 8 wherein the herpetoviridae protease is a serine herpetoviridae protease.

10. The method of claim 8 wherein the serine herpetoviridae protease is assemblin.

* * * * *

UNITED STATES PATENT AND TRADEMARK OFFICE
CERTIFICATE OF CORRECTION

PATENT NO. : 6,906,078 B2
DATED : June 14, 2005
INVENTOR(S) : Moorman et al.

It is certified that error appears in the above-identified patent and that said Letters Patent is hereby corrected as shown below:

<u>Title page,</u>
Item [63], Related U.S. Application Data, "April 24, 1994, now abandoned" should read -- April 29, 1994, now abandoned --.

<u>Column 1,</u>
Lines 11-12, "Apr. 24, 1994" should read -- Apr. 29, 1994 --.

<u>Column 70,</u>
Line 63, "claim 8" should read -- claim 5 --.

Signed and Sealed this

Twenty-first Day of March, 2006

JON W. DUDAS
*Director of the United States Patent and Trademark Office*

SEQUENCE LISTING

<160> NUMBER OF SEQ ID NOS: 2

<210> SEQ ID NO 1
<211> LENGTH: 13
<212> TYPE: PRT
<213> ORGANISM: Human cytomegalovirus
<220> FEATURE:
<221> NAME/KEY: PEPTIDE
<222> LOCATION: (1)..(13)
<223> OTHER INFORMATION: assembly protein maturation site

<400> SEQUENCE: 1

Ala Gly Val Val Asn Ala Ser Cys Arg Leu Ala Thr Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: part of substrate for HCMV protease

<400> SEQUENCE: 2

Gly Val Val Asn Ala Ser Ala Arg Leu Ala
1               5                   10